(12) United States Patent
Christensen

(10) Patent No.: US 10,988,810 B2
(45) Date of Patent: Apr. 27, 2021

(54) METHODS AND MATERIALS FOR DETECTION OF MUTATIONS

(71) Applicant: PentaBase ApS, Odense C (DK)

(72) Inventor: Ulf Bech Christensen, Odense C (DK)

(73) Assignee: PentaBase ApS, Odense C (DK)

( * ) Notice: Subject to any disclaimer, the term of this patent is extended or adjusted under 35 U.S.C. 154(b) by 320 days.

(21) Appl. No.: 15/759,619

(22) PCT Filed: Sep. 14, 2016

(86) PCT No.: PCT/DK2016/050299
§ 371 (c)(1),
(2) Date: Mar. 13, 2018

(87) PCT Pub. No.: WO2017/045689
PCT Pub. Date: Mar. 23, 2017

(65) Prior Publication Data
US 2019/0085400 A1    Mar. 21, 2019

(30) Foreign Application Priority Data
Sep. 14, 2015   (DK) .............. PA 2015 70588

(51) Int. Cl.
C12Q 1/68      (2018.01)
C12N 15/00     (2006.01)
C12Q 1/6886    (2018.01)
C12Q 1/6858    (2018.01)

(52) U.S. Cl.
CPC ......... *C12Q 1/6886* (2013.01); *C12Q 1/6858* (2013.01); *C12N 15/00* (2013.01); *C12Q 2600/106* (2013.01)

(58) Field of Classification Search
None
See application file for complete search history.

(56) References Cited

U.S. PATENT DOCUMENTS

| 2005/0064463 A1 | 3/2005 | Hedgpeth et al. |
| 2013/0177918 A1 | 7/2013 | Terasaki et al. |

FOREIGN PATENT DOCUMENTS

| WO | 2003043402 | 5/2003 |
| WO | 2003052134 | 6/2003 |
| WO | 2003072051 | 9/2003 |
| WO | 2007104318 | 9/2007 |
| WO | 2007106534 | 9/2007 |
| WO | 2012075231 | 6/2012 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
U. B. Christensen and Erik B. Pedersen, "Intercalating Nucleic Acids Containing Insertions of 1-0-(1-pyrenylmethyl)glycerol: Stabilization of dsDNA and Discrimination of DNA over RNA"; Nucleic Acids Research, Information Retrieval Ltd., vol. 30, No. 22, 2002, pp. 4918-4925.
Minakshi Guha et al, "Dissect Method Using PNA-LNA Clamp Improves Detection of EGFR T790m Mutation"; PLOS ONE, vol. 8, No. 6. Jun. 21, 2013, p. e67782, XP055322590.
B. Sobrino et al, "SNPs in Forensic Genetics: A Review on SNP Typing Methodologies"; Forensic Science International, Elsevier Scientific Publishers, Ireland, Ltd., vol. 154, No. 2-3, Nov. 25, 2005, pp. 181-194.

* cited by examiner

*Primary Examiner* — James Martinell

(74) *Attorney, Agent, or Firm* — Dinsmore & Shohl LLP; Weston R. Gould

(57) ABSTRACT

Provided herein are specially modified blocking nucleotides allowing for the sensitive detection of low copies of variant sequences, while significantly reducing signals from non-variant sequences that are similar but not identical to the variant sequence. These nucleotides can be used to detect rare variants in a sample mixture, as described in the present methods.

20 Claims, 13 Drawing Sheets
Specification includes a Sequence Listing.

A)

B)

| Examples of Primer 1 and Blocking Oligonucleotide Sequences | | | | |
|---|---|---|---|---|
| Assay No. | Gene | Oligo | SEQ ID NO | Oligo sequence |
| 1 | KRAS G12A | Primer 1 | 16 | ZGCACTCTTGCCTACGCGAT |
| | | Primer 2 | 28 | ZACCTTATGTGTGACATGTTCTAATATAGT |
| | | Blocking oligonucleotide | 17 | ZCCTACZGCCZACCAGCZT |
| 2 | KRAS A146T | Primer 1 | 18 | TTACTTACCTGTCTTGTCTTCGT |
| | | Primer 2 | 29 | TGCCTTCTAGAACAGTAGACAC |
| | | Blocking oligonucleotide | 19 | ZCTGTCTTZGTCTTTZGCTGZATGTZT |
| 3 | NRAS Q61R | Primer 1 | 20 | CTCATGGCACTGTACTCTTATC |
| | | Primer 2 | 30 | CCAGGATTCTTACAGAAAACAAG |
| | | Blocking oligonucleotide | 21 | ZCTCZTTCTTZGTCCZAGCTZ |
| 4 | NRAS Q61K | Primer 1 | 22 | CTCATGGCACTGTACTCTTCGTT |
| | | Primer 2 | 30 | CCAGGATTCTTACAGAAAACAAG |
| | | Blocking oligonucleotide | 23 | ZTACTCZTTCTTZGTCCZAGCTZG |
| 5 | NRAS Q61L | Primer 1 | 24 | CTCATGGCACTGTACTCTTGTA |
| | | Primer 2 | 30 | CCAGGATTCTTACAGAAAACAAG |
| | | Blocking oligonucleotide | 25 | ZTACTCZTTCTTGTCCZAGCTZG |
| 6 | NRAS K117N1 | Primer 1 | 26 | GTCCTTGTTGGCAAATCAAAG |
| | | Primer 2 | 31 | TGTACCCAGCCTAATCTTGT |
| | | Blocking oligonucleotide | 27 | ZGGCAAZATCACZACTTZGTTTCCZ |

| NRAS Simplex ||||
| --- | --- | --- | --- |
| Oligo | 5' – sequence | SEQ ID NO | Final concentration (nM) |
| NRAS A59D primer 1 | TTGTTGGACATACTGGATACCGA | 6 | 450 |
| NRAS 59 primer 2 | TGCTATTATTGATGGCAAATACAC | 7 | 450 |
| NRAS 59 probe | CAATACATGAGGACAGGC | 8 | 200 |
| NRAS 59 BaseBlocker blocking oligo-nucleotide | ZCAGCTZGGACAAGAZAGAGTZ | 9 | 500 |
| | Quantification cycle (Cq) |||
| Template | Without blocker || With blocker |
| Wild type | 37.7 || n.d. |
| Wild type + A59D | 33.51 || 33.67 |

| KRAS Multiplex | | | |
|---|---|---|---|
| Oligo | 5' – sequence | SEQ ID NO | Final concentration (nM) |
| KRAS 59/61 primer 2 | CCTTCTCAGGATTCCTACAGG | 10 | 900 |
| KRAS Q61K primer 1 | CCTCATTGCACTGTACTCCTCCTT | 11 | 450 |
| KRAS Q61L primer 1 | CCTCATTGCACTGTACTCCTTTA | 12 | 450 |
| KRAS A59G primer 1 | CACTGTACTCCTCTTGACATC | 13 | 450 |
| KRAS 61 probe | ACAGGTTTCTCCATCAATTACTA | 14 | 200 |
| KRAS 59/61 BaseBlocker blocking oligonucleotide | ZCCTCZTTGACZCTGCTZGTGTZ | 15 | 5000 |
| | Quantification cycle (Cq) | | |
| Template | Without blocker | With blocker | |
| Wild type | 31.0 | n.d. | |
| Wild type+Q61K | 28.4 | 30.3 | |
| Wild type+Q61L | 27.5 | 29.9 | |
| Wild type+A59G | 29.0 | 31.6 | |

| KRAS mutations detected by SensiScreen® |||
| --- | --- | --- | --- |
| Assay | CDS mutation | Amino acid mutation | Cosmic ID |
| KRAS exon 2 | c.35G>C | Gly12Ala (G12A) | COSM522 |
| | c.35G>A | Gly12Asp (G12D) | COSM521 |
| | c.34G>C | Gly12Arg (G12R) | COSM518 |
| | c.34G>T | Gly12Cys (G12C) | COSM516 |
| | c.34G>A | Gly12Ser (G12S) | COSM517 |
| | c.35G>T | Gly12Val (G12V) | COSM520 |
| | c.38G>A | Gly13Asp (G13D) | COSM532 |
| | c.34_35GG>TT | Gly12Phe (G12F) | COSM512 |
| | c.34_35GG>AT | Gly12Ile (G12I) | COSM34144 |

B)

| Comparison of SensiScreen® to competitors' methods for KRAS exon 2 mutation testing |||||
| --- | --- | --- | --- | --- |
| Assay | Competitor's method | Total patient samples | Mutated cases identified Competitor SensiScreen® | Additional cases identified by SensiScreen® |
| KRAS exon 2 multiplex | cobas® | 307 | 84        88 | 4 (5%) |
| KRAS exon 2 simplex | Direct sequencing | 180 | 46        65 | 19 (41%) |
| | therascreen | 80 | 19        20 | 1 (5%) |
| | Mutant-enriched PCR | 100 | 43        45 | 2 (5%) |

Fig. 10

SEQUENCE LISTING

```
<160> NUMBER OF SEQ ID NOS: 31

<210> SEQ ID NO 1
<211> LENGTH: 766
<212> TYPE: PRT
<213> ORGANISM: homo sapiens

<400> SEQUENCE: 1

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300
```

-continued

```
Ala Ser Leu Ala Glu Thr Ala Leu Thr Ser Gly Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700

Pro Leu Phe Pro Gln Ile Leu Ala Ser Ile Glu Leu Leu Ala Arg Ser
705                 710                 715                 720
```

```
Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 2
<211> LENGTH: 1210
<212> TYPE: PRT
<213> ORGANISM: homo sapiens

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335
```

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

```
Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
1010                1015                1020

Phe Ser  Ser Pro Ser Thr Ser  Arg Thr Pro Leu Leu  Ser Ser Leu
1025                1030                1035

Ser Ala  Thr Ser Asn Asn Ser  Thr Val Ala Cys Ile  Asp Arg Asn
1040                1045                1050

Gly Leu  Gln Ser Cys Pro Ile  Lys Glu Asp Ser Phe  Leu Gln Arg
1055                1060                1065

Tyr Ser  Ser Asp Pro Thr Gly  Ala Leu Thr Glu Asp  Ser Ile Asp
1070                1075                1080

Asp Thr  Phe Leu Pro Val Pro  Glu Tyr Ile Asn Gln  Ser Val Pro
1085                1090                1095

Lys Arg  Pro Ala Gly Ser Val  Gln Asn Pro Val Tyr  His Asn Gln
1100                1105                1110

Pro Leu  Asn Pro Ala Pro Ser  Arg Asp Pro His Tyr  Gln Asp Pro
1115                1120                1125

His Ser  Thr Ala Val Gly Asn  Pro Glu Tyr Leu Asn  Thr Val Gln
1130                1135                1140

Pro Thr  Cys Val Asn Ser Thr  Phe Asp Ser Pro Ala  His Trp Ala
1145                1150                1155

Gln Lys  Gly Ser His Gln Ile  Ser Leu Asp Asn Pro  Asp Tyr Gln
```

```
            1160                1165                1170

Gln Asp Phe Phe Pro Lys Glu Ala Lys Pro Asn Gly Ile Phe Lys
            1175                1180                1185

Gly Ser Thr Ala Glu Asn Ala Glu Tyr Leu Arg Val Ala Pro Gln
            1190                1195                1200

Ser Ser Glu Phe Ile Gly Ala
            1205            1210

<210> SEQ ID NO 3
<211> LENGTH: 189
<212> TYPE: PRT
<213> ORGANISM: homo sapiens

<400> SEQUENCE: 3

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 4
<211> LENGTH: 189
<212> TYPE: PRT
<213> ORGANISM: homo sapiens

<400> SEQUENCE: 4

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
```

```
                            85                  90                  95
Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
                180                 185

<210> SEQ ID NO 5
<211> LENGTH: 1068
<212> TYPE: PRT
<213> ORGANISM: homo sapiens

<400> SEQUENCE: 5

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
                100                 105                 110

Leu Asn Arg Glu Ile Gly Phe Ala Ile Gly Met Pro Val Cys Glu Phe
            115                 120                 125

Asp Met Val Lys Asp Pro Glu Val Gln Asp Phe Arg Arg Asn Ile Leu
        130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
225                 230                 235                 240

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
                260                 265                 270
```

-continued

```
Ile Arg Ser Cys Ile Met Leu Gly Arg Met Pro Asn Leu Met Leu Met
            275                 280                 285

Ala Lys Glu Ser Leu Tyr Ser Gln Leu Pro Met Asp Cys Phe Thr Met
        290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
```

```
                690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
                740                 745                 750

Ser Pro Leu Asn Pro Ala His Gln Leu Gly Asn Leu Arg Leu Glu Glu
                755                 760                 765

Cys Arg Ile Met Ser Ser Ala Lys Arg Pro Leu Trp Leu Asn Trp Glu
                770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
                820                 825                 830

Met Leu Pro Tyr Gly Cys Leu Ser Ile Gly Asp Cys Val Gly Leu Ile
                835                 840                 845

Glu Val Val Arg Asn Ser His Thr Ile Met Gln Ile Gln Cys Lys Gly
850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
                900                 905                 910

Ile Gly Asp Arg His Asn Ser Asn Ile Met Val Lys Asp Asp Gly Gln
                915                 920                 925

Leu Phe His Ile Asp Phe Gly His Phe Leu Asp His Lys Lys Lys Lys
                930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
                980                 985                 990

Gln His Ala Asn Leu Phe Ile Asn Leu Phe Ser Met Met Leu Gly Ser
                995                 1000                1005

Gly Met Pro Glu Leu Gln Ser Phe Asp Asp Ile Ala Tyr Ile Arg
        1010                1015                1020

Lys Thr Leu Ala Leu Asp Lys Thr Glu Gln Glu Ala Leu Glu Tyr
        1025                1030                1035

Phe Met Lys Gln Met Asn Asp Ala His His Gly Gly Trp Thr Thr
        1040                1045                1050

Lys Met Asp Trp Ile Phe His Thr Ile Lys Gln His Ala Leu Asn
        1055                1060                1065

<210> SEQ ID NO 6
<211> LENGTH: 23
<212> TYPE: DNA
<213> ORGANISM: Artificial sequence
<220> FEATURE:
<223> OTHER INFORMATION: Primer
```

<400> SEQUENCE: 6
ttgttggaca tactggatac cga                                     23

<210> SEQ ID NO 7
<211> LENGTH: 24
<212> TYPE: DNA
<213> ORGANISM: Artificial sequence
<220> FEATURE:
<223> OTHER INFORMATION: Primer

<400> SEQUENCE: 7
tgctattatt gatggcaaat acac                                    24

<210> SEQ ID NO 8
<211> LENGTH: 18
<212> TYPE: DNA
<213> ORGANISM: Artificial sequence
<220> FEATURE:
<223> OTHER INFORMATION: Primer

<400> SEQUENCE: 8
caatacatga ggacaggc                                           18

<210> SEQ ID NO 9
<211> LENGTH: 22
<212> TYPE: DNA
<213> ORGANISM: Artificial sequence
<220> FEATURE:
<223> OTHER INFORMATION: Blocking oligonucleotide
<220> FEATURE:
<221> NAME/KEY: misc_feature
<222> LOCATION: (1)..(1)
<223> OTHER INFORMATION: n is hydrophobic nucleotide
<220> FEATURE:
<221> NAME/KEY: misc_feature
<222> LOCATION: (7)..(7)
<223> OTHER INFORMATION: n is hydrophobic nucleotide
<220> FEATURE:
<221> NAME/KEY: misc_feature
<222> LOCATION: (16)..(16)
<223> OTHER INFORMATION: n is hydrophobic nucleotide
<220> FEATURE:
<221> NAME/KEY: misc_feature
<222> LOCATION: (22)..(22)
<223> OTHER INFORMATION: n is hydrophobic nucleotide

<400> SEQUENCE: 9
ncagctngga caaganagag tn                                      22

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
ccttctcagg attcctacag g                                       21

<210> SEQ ID NO 11
<211> LENGTH: 24
<212> TYPE: DNA
<213> ORGANISM: Artificial sequence
<220> FEATURE:
<223> OTHER INFORMATION: Primer

<400> SEQUENCE: 11
cctcattgca ctgtactcct cctt                                    24

```
<210> SEQ ID NO 12
<211> LENGTH: 23
<212> TYPE: DNA
<213> ORGANISM: Artificial sequence
<220> FEATURE:
<223> OTHER INFORMATION: Primer

<400> SEQUENCE: 12
cctcattgca ctgtactcct tta                                                   23

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
cactgtactc ctcttgacat c                                                     21

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
acaggtttct ccatcaatta cta                                                   23

<210> SEQ ID NO 15
<211> LENGTH: 23
<212> TYPE: DNA
<213> ORGANISM: Artificial sequence
<220> FEATURE:
<223> OTHER INFORMATION: Blocking oligonucleotide
<220> FEATURE:
<221> NAME/KEY: misc_feature
<222> LOCATION: (1)..(1)
<223> OTHER INFORMATION: n is a hydrophobic nucleotide
<220> FEATURE:
<221> NAME/KEY: misc_feature
<222> LOCATION: (6)..(6)
<223> OTHER INFORMATION: n is a hydrophobic nucleotide
<220> FEATURE:
<221> NAME/KEY: misc_feature
<222> LOCATION: (12)..(12)
<223> OTHER INFORMATION: n is a hydrophobic nucleotide
<220> FEATURE:
<221> NAME/KEY: misc_feature
<222> LOCATION: (18)..(18)
<223> OTHER INFORMATION: n is a hydrophobic nucleotide
<220> FEATURE:
<221> NAME/KEY: misc_feature
<222> LOCATION: (23)..(23)
<223> OTHER INFORMATION: n is a hydrophobic nucleotide

<400> SEQUENCE: 15
ncctcnttga cnctgctngt gtn                                                   23

<210> SEQ ID NO 16
<211> LENGTH: 20
<212> TYPE: DNA
<213> ORGANISM: Artificial sequence
<220> FEATURE:
<223> OTHER INFORMATION: Primer 1
<220> FEATURE:
<221> NAME/KEY: misc_feature
<222> LOCATION: (1)..(1)
```

<223> OTHER INFORMATION: n is a hydrophobic nucleotide

<400> SEQUENCE: 16
ngcactcttg cctacgcgat                                                    20

<210> SEQ ID NO 17
<211> LENGTH: 19
<212> TYPE: DNA
<213> ORGANISM: Artificial sequence
<220> FEATURE:
<223> OTHER INFORMATION: Blocking nucleotide
<220> FEATURE:
<221> NAME/KEY: misc_feature
<222> LOCATION: (1)..(1)
<223> OTHER INFORMATION: n is a hydrophobic nucleotide
<220> FEATURE:
<221> NAME/KEY: misc_feature
<222> LOCATION: (7)..(7)
<223> OTHER INFORMATION: n is a hydrophobic nucleotide
<220> FEATURE:
<221> NAME/KEY: misc_feature
<222> LOCATION: (11)..(11)
<223> OTHER INFORMATION: n is a hydrophobic nucleotide
<220> FEATURE:
<221> NAME/KEY: misc_feature
<222> LOCATION: (18)..(18)
<223> OTHER INFORMATION: n is a hydrophobic nucleotide

<400> SEQUENCE: 17
ncctacngcc naccagcnt                                                     19

<210> SEQ ID NO 18
<211> LENGTH: 23
<212> TYPE: DNA
<213> ORGANISM: Artificial sequence
<220> FEATURE:
<223> OTHER INFORMATION: Primer 1

<400> SEQUENCE: 18
ttacttacct gtcttgtctt cgt                                                23

<210> SEQ ID NO 19
<211> LENGTH: 27
<212> TYPE: DNA
<213> ORGANISM: Artificial sequence
<220> FEATURE:
<223> OTHER INFORMATION: Blocking oligonucleotide
<220> FEATURE:
<221> NAME/KEY: misc_feature
<222> LOCATION: (1)..(1)
<223> OTHER INFORMATION: n is a hydrophobic nucleotide
<220> FEATURE:
<221> NAME/KEY: misc_feature
<222> LOCATION: (9)..(9)
<223> OTHER INFORMATION: n is a hydrophobic nucleotide
<220> FEATURE:
<221> NAME/KEY: misc_feature
<222> LOCATION: (16)..(16)
<223> OTHER INFORMATION: n is a hydrophobic nucleotide
<220> FEATURE:
<221> NAME/KEY: misc_feature
<222> LOCATION: (21)..(21)
<223> OTHER INFORMATION: n is a hydrophobic nucleotide
<220> FEATURE:
<221> NAME/KEY: misc_feature
<222> LOCATION: (26)..(26)
<223> OTHER INFORMATION: n is a hydrophobic nucleotide

<400> SEQUENCE: 19
nctgtcttng tctttngctg natgtnt                                            27

```
<210> SEQ ID NO 20
<211> LENGTH: 22
<212> TYPE: DNA
<213> ORGANISM: Artificial sequence
<220> FEATURE:
<223> OTHER INFORMATION: Primer 1

<400> SEQUENCE: 20
ctcatggcac tgtactctta tc                                            22

<210> SEQ ID NO 21
<211> LENGTH: 21
<212> TYPE: DNA
<213> ORGANISM: Artificial sequence
<220> FEATURE:
<223> OTHER INFORMATION: blocking oligonucleotide
<220> FEATURE:
<221> NAME/KEY: misc_feature
<222> LOCATION: (1)..(1)
<223> OTHER INFORMATION: n is a hydrophobic nucleotide
<220> FEATURE:
<221> NAME/KEY: misc_feature
<222> LOCATION: (5)..(5)
<223> OTHER INFORMATION: n is a hydrophobic nucleotide
<220> FEATURE:
<221> NAME/KEY: misc_feature
<222> LOCATION: (11)..(11)
<223> OTHER INFORMATION: n is a hydrophobic nucleotide
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (21)..(21)
<223> OTHER INFORMATION: n is a hydrophobic nucleotide

<400> SEQUENCE: 21
nctcnttctt ngtccnagct n                                             21

<210> SEQ ID NO 22
<211> LENGTH: 23
<212> TYPE: DNA
<213> ORGANISM: Artificial sequence
<220> FEATURE:
<223> OTHER INFORMATION: Primer 1

<400> SEQUENCE: 22
ctcatggcac tgtactcttc gtt                                           23

<210> SEQ ID NO 23
<211> LENGTH: 24
<212> TYPE: DNA
<213> ORGANISM: Artificial sequence
<220> FEATURE:
<223> OTHER INFORMATION: Blocking oligonucleotide
<220> FEATURE:
<221> NAME/KEY: misc_feature
<222> LOCATION: (1)..(1)
<223> OTHER INFORMATION: n is a hydrophobic nucleotide
<220> FEATURE:
<221> NAME/KEY: misc_feature
<222> LOCATION: (7)..(7)
<223> OTHER INFORMATION: n is a hydrophobic nucleotide
<220> FEATURE:
<221> NAME/KEY: misc_feature
<222> LOCATION: (13)..(13)
<223> OTHER INFORMATION: n is a hydrophobic nucleotide
<220> FEATURE:
<221> NAME/KEY: misc_feature
<222> LOCATION: (18)..(18)
<223> OTHER INFORMATION: n is a hydrophobic nucleotide
<220> FEATURE:
```

```
<221> NAME/KEY: misc_feature
<222> LOCATION: (23)..(23)
<223> OTHER INFORMATION: n is a hydrophobic nucleotide

<400> SEQUENCE: 23
ntactcnttc ttngtccnag ctng                                              24

<210> SEQ ID NO 24
<211> LENGTH: 22
<212> TYPE: DNA
<213> ORGANISM: Artificial sequence
<220> FEATURE:
<223> OTHER INFORMATION: Primer

<400> SEQUENCE: 24
ctcatggcac tgtactcttg ta                                                22

<210> SEQ ID NO 25
<211> LENGTH: 23
<212> TYPE: DNA
<213> ORGANISM: Artificial sequence
<220> FEATURE:
<223> OTHER INFORMATION: Blocking oligonucleotide
<220> FEATURE:
<221> NAME/KEY: misc_feature
<222> LOCATION: (1)..(1)
<223> OTHER INFORMATION: n is a hydrophobic nucleotide
<220> FEATURE:
<221> NAME/KEY: misc_feature
<222> LOCATION: (7)..(7)
<223> OTHER INFORMATION: n is a hydrophobic nucleotide
<220> FEATURE:
<221> NAME/KEY: misc_feature
<222> LOCATION: (17)..(17)
<223> OTHER INFORMATION: n is a hydrophobic nucleotide
<220> FEATURE:
<221> NAME/KEY: misc_feature
<222> LOCATION: (22)..(22)
<223> OTHER INFORMATION: n is a hydrophobic nucleotide

<400> SEQUENCE: 25
ntactcnttc ttgtccnagc tng                                               23

<210> SEQ ID NO 26
<211> LENGTH: 21
<212> TYPE: DNA
<213> ORGANISM: Artificial sequence
<220> FEATURE:
<223> OTHER INFORMATION: Primer 1

<400> SEQUENCE: 26
gtccttgttg gcaaatcaaa g                                                 21

<210> SEQ ID NO 27
<211> LENGTH: 25
<212> TYPE: DNA
<213> ORGANISM: Artificial sequence
<220> FEATURE:
<223> OTHER INFORMATION: Blocking oligonucleotide
<220> FEATURE:
<221> NAME/KEY: misc_feature
<222> LOCATION: (1)..(1)
<223> OTHER INFORMATION: n is a hydrophobic nucleotide
<220> FEATURE:
<221> NAME/KEY: misc_feature
<222> LOCATION: (7)..(7)
<223> OTHER INFORMATION: n is a hydrophobic nucleotide
<220> FEATURE:
<221> NAME/KEY: misc_feature
<222> LOCATION: (13)..(13)
<223> OTHER INFORMATION: n is a hydrophobic nucleotide
```

```
<220> FEATURE:
<221> NAME/KEY: misc_feature
<222> LOCATION: (18)..(18)
<223> OTHER INFORMATION: n is a hydrophobic nucleotide
<220> FEATURE:
<221> NAME/KEY: misc_feature
<222> LOCATION: (25)..(25)
<223> OTHER INFORMATION: n is a hydrophobic nucleotide

<400> SEQUENCE: 27
nggcaanatc acnacttngt ttccn                                            25

<210> SEQ ID NO 28
<211> LENGTH: 30
<212> TYPE: DNA
<213> ORGANISM: Artificial sequence
<220> FEATURE:
<223> OTHER INFORMATION: Primer 2
<220> FEATURE:
<221> NAME/KEY: misc_feature
<222> LOCATION: (1)..(1)
<223> OTHER INFORMATION: n is a hydrophobic nucleotide

<400> SEQUENCE: 28
naccttatgt gtgacatgtt ctaatatagt                                       30

<210> SEQ ID NO 29
<211> LENGTH: 22
<212> TYPE: DNA
<213> ORGANISM: Artificial sequence
<220> FEATURE:
<223> OTHER INFORMATION: Primer 2

<400> SEQUENCE: 29
tgccttctag aacagtagac ac                                               22

<210> SEQ ID NO 30
<211> LENGTH: 23
<212> TYPE: DNA
<213> ORGANISM: Artificial sequence
<220> FEATURE:
<223> OTHER INFORMATION: Primer 2

<400> SEQUENCE: 30
ccaggattct tacagaaaac aag                                              23

<210> SEQ ID NO 31
<211> LENGTH: 20
<212> TYPE: DNA
<213> ORGANISM: Artificial sequence
<220> FEATURE:
<223> OTHER INFORMATION: Primer 2

<400> SEQUENCE: 31
tgtacccagc ctaatcttgt                                                  20
```

METHODS AND MATERIALS FOR DETECTION OF MUTATIONS

BACKGROUND

In 2013 there were at least 387 targeted drugs marketed or in the pipeline for oncology. Common for all these drugs are that they only work on people/diseases with a certain genetic composition. Hence, treatment of disease is linked to genetics and is moving away from the one-size fits all concept and into a more personalized approach. Drugs for oncology are the front runners in this new treatment paradigm, but other areas are expected to follow. In personalized medicine the patient is matched with the drug(s) by using what is called companion diagnostic, giving the patient a significantly higher chance of positively responding to the treatment, than if the drug was given randomly to patients with that disease. For example, metastatic colorectal cancer (mCRC) is one of the most commonly diagnosed cancers and one of the most common causes of cancer-related deaths in the world. Approximately one million new cases are diagnosed each year and the incidence of new cases of CRC is predicted to be 9.7% of the global cancer cases by 2020. Therapeutics (like Cetuximab and Panitumumab) targeting the Epidermal Growth Factor Receptor (EGFR) are effective for treatment of a subgroup of mCRC patients, but unfortunately, approximately 70% of mCRC patients do not respond to these expensive drugs. It is now clear that the main reason for the lack of response is the development of somatic mutations (SMs) at specific positions in certain genes of the primary tumour and metastases of the patient. In particular, it has been widely demonstrated that mutations in the oncogene KRAS exon 2, codons 12/13 correlate with lack of response to and with inferior overall survival (OS) when treating with anti-EGFR drugs alone or in combination with chemotherapy (like FOLFOX4 or FOLFIRI schemes). Consequently, an analysis on biopsies for the seven most common mutations in KRAS codon 12/13 (exon 2) mutations has been required since 2009 before administration of these drugs. In January 2014 the list of mandatory SMs to test for were expanded to more than 30 SMs in the KRAS and NRAS genes in total, in order to identify even more non-responders of anti-EGFR drugs. Approximately 40% of all mCRC patients are found to have mutations in exon 2 of KRAS (KRAS codon 12/13) with current assays. With the extended version looking at more RAS mutations, approximately 50% are now found to harbour a RAS mutation rendering them resistant to anti-EGFR drugs. Despite this stratification based on the connection between mutations in all RAS genes and anti-EGFR resistance, 40-60% of patients found to carry wild type RAS tumours do still not respond to treatment with anti-EGFR therapies.

This means that these patients are either falsely diagnosed as RAS wild type (false negatives) or that the presence of other genetic variations may confer resistance to the treatment.

One of the challenges when detecting somatic mutations is that there is potentially a lot of wild type material present in the sample and/or often only a few copies of the mutated template in the mixture. The sensitivity and specificity of the method used for detecting somatic mutations is therefore important to reduce the number of false negatives and false positives.

Two additional types of cancers characterized by high incidence and mortality are Non Small Cell Lung Cancer (NSCLC) and Malignant Melanoma (MM). Both tumors are usually resistant to chemotherapies, while it has been demonstrated that a great benefit can be achieved for patients who can be treated with targeted therapies (EGFR-targeted therapies in NSCLC, BRAF-targeted therapies in MM). In NSCLC, however, there is a specific type of EGFR mutation (located in exon 20, the T790M change) which is linked with lack of efficacy of EGFR-targeted therapies. This type of mutation can occur in non-treated patients, but usually represents the main mechanism of acquired resistance to EGFR-targeted therapies. Therefore, a precise evaluation of EGFR T790M mutation is of primary importance in setting the appropriate treatment for NSCLC patients. For MM, a type of disease characterized, when at late stage, by a very severe prognosis, the possibility to receive BRAF-targeted therapies can significantly improve patients' follow-up. Overall, the use of high sensitive methodologies for RAS, EGFR and BRAF mutations in CRC, NSCLC and MM patients, respectively, lead to reduced spending on inefficient treatments and increasing progression free survival (PFS) and OS for patients.

Blood is usually the carrier allowing cancer to migrate into other organs and researchers have therefore been attracted by the analysis of this material. Furthermore, SMs can arise in a separate subset of cells in the often heterogeneous primary tumour or in one or more of the metastases and thereby escape detection when done on slices from biopsies. In the blood system, there are at least two types of cancer-associated materials: Circulating Tumour Cells (CTCs) and cell-free circulating DNA (cfDNA). During tumour expansion at local level, the tumoral mass requires an increased quantity of nutrients, and therefore cancer cells lead to the organization of new blood vessels, which are linked to the normal blood system. This process, named neo-angiogenesis, is required for a further expansion of tumour mass. Cancer cells close to the blood system may also acquire the capability to enter into blood vessels, and therefore their detection into blood directly represents the identification of an aggressive disease. In addition, due to apoptotic-necrotic processes not completely understood, cancer cells in the blood system or close to blood vessels may lysate, leading to the dispersion of genetic material like cfDNA into the blood. Also, in this case, the possibility to detect cfDNA may lead to an early identification of an aggressive disease (i.e. tumor relapse).

Somatic mutations are not only found in cancer related diseases but for example also in disorders of neuronal migration in the brain. Mutations in the gene lissencephaly-1 (LIS1) are typically associated with a "smooth brain" phenotype of lissencephaly. The mutations were detectable in mosaic form in leukocytes, suggesting that a relatively early postzygotic, somatic mutation occurred. Somatic mutations have also been described in cases without visible focal lesions, including in epilepsy. For example, severe myoclonic epilepsy of infancy (Dravet syndrome), typically caused by de novo mutations in the gene encoding the sodium channel alpha-1 subunit, SCN1A, has been described.

Non-invasive prenatal testing (NIPT) of fetal genetic material is another situation where rare variants in a mixed sample are analysed for. Fetal aneuploidy using cell-free fetal DNA is for example becoming part of routine clinical practice. The possibility to detect rare variants is important and can help change clinical practise in genetic analysis of fetal DNA.

SUMMARY OF THE INVENTION

The present invention addresses the challenge of detecting rare variants in a sample mixture. This could be somatic mutations where sometimes only a few copies of the mutated template are present in a sample, which potentially contains a lot of wild type material. The invention addresses this challenge by employing specially modified blocking nucleotides, that allow for the sensitive detection of low copies of variant sequences, while significantly reducing signals from non-variant sequences that are similar but not identical to the variant sequence.

Thus, the methods of the present invention are useful for distinguishing between a variant sequence and a very similar but not identical reference NOI sequence, even if the variant sequence is present at much lower levels than the reference NOI sequence. As explained in the background section, such methods are particularly useful in cancer diagnostics, and for example can be used for designing a personalised treatment regime for cancer patients. However, in addition to detecting the presence of somatic mutations, the present invention is also useful for many other applications. For example, in screenings like Non Invasive Prenatal Test (NIPT) where a foetus's DNA is studied from a blood sample from the mother, it is important to be able to analyze a few copies of target DNA in a large background of non-target DNA.

Accordingly, the methods of the invention can be applied in any setting where detection of a variant sequence is desirable.

Thus, the invention provides methods for detecting the presence of a variant sequence in a target nucleic acid sequence comprising nucleotide(s) of interest (NOI), wherein said NOI may consist of said variant sequence, of other variant sequences or of a reference NOI sequence, said method comprising the steps of
  a) Providing a sample comprising nucleic acids
  b) Providing a blocking oligonucleotide comprising a sequence of in the range of 10 to 50 nucleotides (referred to as "blocking sequence") into which in the range of 2 to 10 hydrophobic nucleotides have been inserted
    wherein
    at least one hydrophobic nucleotide is positioned at the 5' end of said sequence or within 4 nucleotides from the 5' end; and
    at least one hydrophobic nucleotide is positioned at the 3' end of said sequence or within 4 nucleotides from the 3' end; and
    wherein the hydrophobic nucleotide has the structure X—Y-Q
    wherein
    X is a nucleotide or nucleotide analogue or a backbone monomer unit capable of being incorporated into the backbone of a nucleic acid or nucleic acid analogue,
    Q is a intercalator which is not taking part in Watson-Crick hydrogen bonding; and
    Y is a linker moiety linking said nucleotide or nucleotide analogue or backbone monomer unit and said intercalator; and
    wherein the blocking sequence is identical to a consecutive stretch of the target nucleic acid sequence comprising the reference NOI sequence,
  c) Providing a set of primers consisting of primer 1 and primer 2, wherein the set of primers together are capable of amplification of the target nucleic acid sequence comprising the variant sequence, and wherein primer 1 comprises a sequence of at least 15 nucleotides positioned at the 3' end of said primer, which is identical to a consecutive stretch of the target nucleic acid sequence comprising the variant sequence expect for up to one mismatch;
  d) performing a polymerase chain reaction in the presence of said sample, said blocking oligonucleotide; said set of primers and PCR reagents;
  e) detecting a product of said polymerase chain reaction, wherein the presence of a product of said polymerase chain reaction indicates the presence of a target nucleic acid sequence comprising the variant sequence in said sample.

The invention also provides kits-of-parts comprising
  a) a blocking oligonucleotide consisting of a sequence of in the range of 10 to 50 nucleotides (referred to as "blocking sequence") into which in the range of 2 to 10 hydrophobic nucleotides have been inserted,
    wherein
    at least one hydrophobic nucleotide is positioned at the 5' end of said sequence or within 4 nucleotides from the 5' end; and
    at least one hydrophobic nucleotide is positioned at the 3' end of said sequence or within 4 nucleotides from the 3' end; and
    Z is a hydrophobic nucleotide of the structure X—Y-Q
    wherein
    X is a backbone monomer unit capable of being incorporated into the backbone of a nucleic acid or nucleic acid analogue,
    Q is an intercalator, which is not taking part in Watson-Crick hydrogen bonding; and
    Y is a linker moiety linking said nucleotide or nucleotide analogue or backbone monomer unit and said intercalator; and
    wherein the blocking sequence is identical to a consecutive stretch of a target nucleic acid sequence comprising a reference NOI sequence; and
  b) a set of primers consisting of primer 1 and primer 2, wherein the set of primers together are capable of amplification of the target nucleic acid sequence comprising a variant sequence, and wherein primer 1 contains a sequence of at least 15 nucleotides positioned at the 3' end of said primer, which is identical to a consecutive stretch of the target nucleic acid sequence comprising the variant sequence expect for up to one mismatch.

The invention also provides blocking oligonucleotides.

The invention also provides methods of predicting the efficacy of treatment of a clinical condition in an individual in need thereof with a predetermined drug, wherein the efficacy of treatment of said clinical condition with said drug is associated with the presence of a variant sequence, said method comprising the steps of
  a. providing a sample from said individual
  b. performing the methods according to the invention for determining the presence of said variant sequence;
  wherein the presence of said variant sequence is indicative of whether said drug is efficient in treating said clinical condition in said individual.

The invention also provides methods of predicting the presence of a clinical condition in an individual in need thereof, wherein said clinical condition is associated with a target nucleic acid sequence comprising a variant sequence, said method comprising the steps of c. providing a sample from said individual
d. performing the methods according to the invention to determine the presence of said variant sequence; wherein the presence of said variant sequence is indicative of said individual suffering from said clinical condition.

DESCRIPTION OF DRAWINGS

FIG. 6C shows sequences of the primers, probe and blocking oligonucleotides used.

FIG. 9A shows the PCR signal (fluorescence signal from a probe) in relation to the PCR cycle number of a KRAS G12S simplex assay. The horizontal line represents a signal of 1. FIG. 9B shows the PCR signal (fluorescence signal from a probe) in relation to the PCR cycle number of a KRAS multiplex assay using G12V variant sequence dilutions.

FIG. 10 shows the summary of three different clinical studies where SensiScreen®, which is the method of the present invention, was compared to 4 common methods for detection of KRAS exon 2 mutation. Formalin-fixed paraffin-embedded DNA from three different patient populations with histologically confirmed colorectal cancer was analysed for the presence of 7 clinically relevant mutations in KRAS exon 2 codons 12 and 13. A) Sequence information of the analysed KRAS exon 2 mutations. B) SensiScreen® identifies 4(5%), 19(41%), 1(5%), and 2(5%) additional mutation positive cases compared to cobas®, direct sequencing, therascreen® and mutant-enriched PCR, respectively.

DETAILED DESCRIPTION OF INVENTION

Definitions

Figure 1:
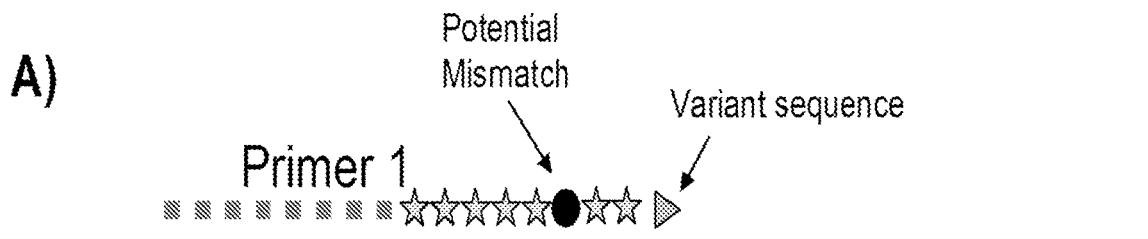
FIG. 1 illustrates an example of how primer 1 shown in A) and the blocking oligonucleotide shown in B) may be designed. In this example, there is a medium sized overlap between primer 1 and the blocking oligonucleotide.
Figure 1:
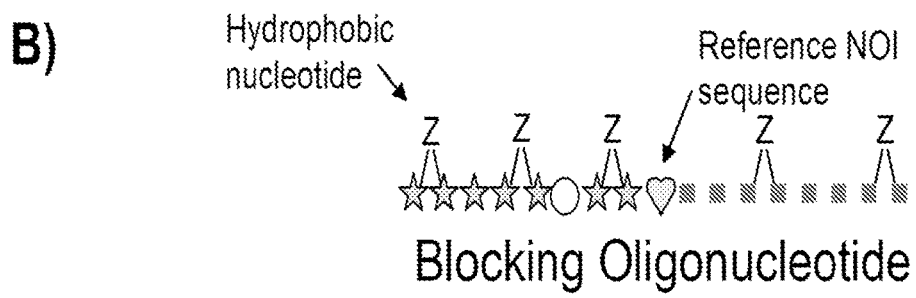

The term "nucleotide" as used herein refers to naturally occuring nucleotides, for example naturally occurring ribonucleotides or deoxyribonucleotides or naturally occurring derivatives of ribonucleotides or deoxyribonucleotides. Naturally occurring nucleotides include deoxyribonucleotides comprising one of the four nucleobases adenine (A), thymine (T), guanine (G) or cytosine (C), and ribonucleotides comprising one of the four nucleobases adenine (A), uracil (U), guanine (G) or cytosine (C).

The term "nucleotide analogue" comprises all nucleotide analogues capable of being incorporated into a nucleic acid backbone and capable of specific base-pairing, essentially like naturally occurring nucleotides. Nucleotide analogues according to the present invention include, but are not limited to the nucleotide analogues selected from the group consisting of PNA, HNA, MNA, ANA, LNA, INA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R$_1$-RNA, 2'-OR$_1$-RNA (R$_1$ being a substituent), α-L-RNA, α-D-RNA, and β-D-RNA.

The term "hydrophobic nucleotide" as used herein refers to the hydrophobic nucleotides described in detail herein below in the section "hydrophobic nucleotide". In particular, a hydrophobic nucleotide according to the invention contains an intercalator connected to a nucleotide/nucleotide analogue/backbone monomer unit via a linker.

The term "melting temperature" as used herein denotes the temperature in degrees centigrade at which 50% helical (hybridised) versus coil (unhybridised) forms are present. Melting temperature may also be referred to as ($T_m$). Melting of nucleic acids and nucleic acid analogues refers to thermal separation of the two strands of a double-stranded nucleic acid molecule.

The term "oligonucleotide" as used herein refers to oligomers of nucleotides and/or nucleotide analogous and/or hydrophobic nucleotides. Preferably, and oligonucleotide is an oligomer of nucleotides optionally comprising one or more hydrophobic nucleotides.

The term "target nucleic acid sequence" as used herein refers to a nucleic acid sequence comprising the nucleotide(s) of interest (NOI). The target nucleic acid sequence can be amplified using a set of primers.

The term "nucleotide(s) of interest" as used herein refers to nucleotide(s) within a target nucleic acid sequence, which may be present in two different variants. "Nucleotide(s) of interest" may also be referred to as "NOI" herein. Thus, the NOI may consist of a variant sequence or it may consist of a reference NOI sequence, also referred to as the "reference NOI sequence" herein. In some embodiments, the reference NOI sequence may be a wild type sequence.

The term "reference target sequence" refers to a stretch of the target nucleic acid sequence comprising the reference NOI sequence. In general, the reference target sequence is identical to the blocking sequence.

The term "variant sequence" as used herein refers to nucleotide(s) within a target nucleic acid sequence, which are different to a reference NOI sequence. Thus, the target nucleic acid sequence may contain a NOI, which is the variant sequence or the target nucleic acid sequence may contain NOI, which is the reference NOI sequence or the NOI may even be yet another variant sequence. The variant sequence may for example be a mutation, such as a single nucleotide mutation or it may be an insertion or deletion.

Methods for Detecting a Variant Sequence in a Target Nucleic Acid Sequence

The invention relates to methods for detection of a variant sequence in a target nucleic acid sequence. Thus, the methods are in particular useful for detecting the presence of a particular sequence in a target nucleic acid sequence, which may occur with two or more different sequences. Thus, the methods can for example be used for distinguishing between a wild type and a mutant sequence. The methods may also be useful for distinguishing between different polymorphic sequences.

Thus, when two or more different target nucleic acid sequences exist, the methods are useful for distinguishing between at least two different target nucleic acid sequences, i.e. the target nucleic acid sequence comprising the variant sequence, and the target nucleic acid sequence not comprising the variant sequence—the latter also being referred to as "reference NOI sequence" and optionally also between target nucleic acid sequences comprising other variant sequences.

In embodiments of the invention where the methods are used for distinguishing between a wild type and a mutant sequence, the mutant sequence may be the reference NOI sequence. However, frequently, the wild type sequence will be the reference NOI sequence. The methods of the invention may also be used for distinguishing between a wild type and several different mutant sequences, in which case the wild type sequence typically will be the reference NOI sequence and the several different mutant sequences will be variant sequences.

The variant sequence may in some embodiments be a mutation indicative of a disease state or it may be predictive for the efficacy of a given treatment.

The methods of the invention may in particular comprise the steps of:
  a) Providing a sample comprising nucleic acids, which may be any of the samples described herein below in the section "Sample";
  b) Providing a blocking oligonucleotide, which may be any of blocking oligonucleotides described herein below in the section "Blocking oligonucleotide"
  c) Providing a set of primers consisting of primer 1 and primer 2, wherein said primers may be any of the primers described herein below in the section "Set of primers";
  d) performing a polymerase chain reaction in the presence of said sample, said blocking oligonucleotide; said set of primers and PCR reagents, which may be any of the reagents described herein below in the section "PCR reagents";
  e) detecting a product of said polymerase chain reaction, wherein the presence of a product of said polymerase chain reaction indicates the presence of a target nucleic acid sequence comprising the variant sequence in said sample.

The blocking oligonucleotide is identical to the reference target sequence except that it contains at least 2 hydrophobic nucleotides inserted as bulge insertions. Because the blocking oligonucleotide is identical to the reference target sequence and contains the hydrophobic nucleotides, the blocking oligonucleotide will have a very high affinity for the complementary reference target sequence. Because the blocking oligonucleotide is not completely identical to the target nucleic acid sequence comprising the variant sequence, the blocking oligonucleotide will not bind the complementary target nucleic acid sequence comprising the variant sequence with similar high affinity. However, primer 1, which contains a sequence almost completely identical to a stretch of the target nucleic acid sequence containing the variant, will bind the complementary sequence with high affinity.

When performing a PCR with the set of primers, the blocking oligonucleotide will block or significantly impair amplification of the target nucleic acid sequence comprising the reference NOI sequence. However, the blocking oligonucleotide will not block or significantly impair amplification of the target nucleic acid sequence comprising the variant sequence. Thus, if a PCR product is generated by PCR with a predefined set of parameters, then the sample contained the variant sequence, whereas if no PCR product is generated by PCR with the predefined set of parameters, then the sample did not comprise the variant sequence. Similarly, if significantly less PCR product is generated compared to a control comprising the variant sequence, this may also be indicative of the sample not comprising the variant sequence. "Significantly less" may in this regard mean less than 50%, such as less less than 25%, for example less than 10%, such as less than 5%.

It is also within the scope of the invention to determine whether a PCR product is generated by the following method:

a) performing a PCR wherein generation of a PCR product may be followed in real time
b) determining the number of PCR cycles performed before a predetermined signal is achieved, wherein said number of PCR cycles are referred to as $C_T$
c) wherein a $C_T$ below a predetermined number is indicative of generation of a PCR product.

Thus, conversely, a $C_T$ above said number may be considered as no presence of a PCR product. The predetermined number could be the $C_T$ value of one PCR reaction relative to the $C_T$ value of another (called $\Delta C_T$), so that a $\Delta C_T$ below a set threshold is indicative of the presence of a variant sequence, whereas a $\Delta C_T$ above a set threshold is indicative of the absence of a variant sequence.

In addition to providing the blocking oligonucleotide with a high affinity for the complementary reference target sequence, the presence of the hydrophobic nucleotides also confers resistance to exonucleases. Thus, if a nucleic acid polymerase having exonuclease activity is used for PCR amplification, this will not degrade the blocking oligonucleotide. Furthermore the presence of the hydrophobic nucleotides ensures that the blocking oligonucleotide does not function well as a primer.

Whether or not a PCR product is generated may be determined in any conventional manner, for example as described herein below in the section "Detection". For example, generation of a PCR product may be followed in real time with the aid of a detection probe.

In one embodiment the methods of invention involves providing one blocking oligonucleotide and one set of primers. However, as described herein the methods may also comprise providing more than one different blocking oligonucleotides and/or more than one different set of primers and/or more than one different primer 1.

Thus, in one embodiment the invention relates to methods for detecting the presence of one specific variant sequence in a target nucleic acid sequence comprising nucleotide(s) of interest (NOI), wherein said NOI may consist of said variant sequence, other variant sequences or of a reference NOI sequence, said method comprising the steps of
a) Providing a sample comprising nucleic acids
b) Providing at least two different blocking oligonucleotides as defined herein, wherein at least one blocking oligonucleotide contains a blocking sequence identical to a consecutive stretch of the target nucleic acid sequence comprising the reference NOI sequence, and one or more blocking oligonucleotide(s) contain blocking sequence(s) identical to a consecutive stretch of the target nucleic acid sequence comprising said other variant sequence(s),
c) Providing a set of primers consisting of primer 1 and primer 2, wherein the set of primers together are capable of amplification of the target nucleic acid sequence comprising the variant sequence, and wherein primer 1 comprises a sequence of at least 15 nucleotides positioned at the 3' end of said primer, which is identical to a consecutive stretch of the target nucleic acid sequence comprising the variant sequence expect for up to one mismatch;
d) performing a polymerase chain reaction in the presence of said sample, said blocking oligonucleotides; said set of primers and PCR reagents;
e) detecting a product of said polymerase chain reaction, wherein the presence of a product of said polymerase chain reaction indicates the presence of a target nucleic acid sequence comprising the variant sequence in said sample.

Such a method may be useful for detection of the presence of one specific variant sequence in a sample, which potentially may comprise a reference NOI sequence as well as one or more "other variant sequences". For example, if the NOI may be present as a plurality of different variant sequences, such a method may be useful for detecting the presence of one specific variant sequence.

In another embodiment the invention relates to methods for detecting the presence of a plurality of variant sequence(s) in a target nucleic acid sequence comprising nucleotide(s) of interest (NOI), wherein said NOI may consist of said plurality of variant sequences or of a reference NOI sequence, said method comprising the steps of
a) Providing a sample comprising nucleic acids
b) Providing a blocking oligonucleotide as defined herein, wherein said blocking oligonucleotide contains a blocking sequence identical to a consecutive stretch of the target nucleic acid sequence comprising the reference NOI sequence,
c) Providing sets of primers comprising at least two different primer 1s and a primer 2, wherein a first primer 1 together with a primer 2 is capable of amplification of the target nucleic acid sequence comprising a first variant sequence, wherein said first primer 1 comprises a sequence of at least 15 nucleotides positioned at the 3' end of said primer, which is identical to a consecutive stretch of the target nucleic acid sequence comprising said first variant sequence expect for up to one mismatch, and a second primer 1 together with a primer 2 is capable of amplification of the target nucleic acid sequence comprising a second variant sequence, wherein said second primer 1 comprises a sequence of at least 15 nucleotides positioned at the 3' end of said primer, which is identical to a consecutive stretch of the target nucleic acid sequence comprising said second variant sequence expect for up to one mismatch; and optionally one or more further primer 1 together with a primer 2 are capable of amplification of the target nucleic acid sequence comprising one or more further variant sequence(s), wherein said further primer 1(s) comprise a sequence of at least 15 nucleotides positioned at the 3' end of said primer, which is identical to a consecutive stretch of the target nucleic acid sequence comprising said further variant sequence(s) expect for up to one mismatch;
d) performing a polymerase chain reaction in the presence of said sample, said blocking oligonucleotide; said sets of primers and PCR reagents;
e) detecting a product of said polymerase chain reaction, wherein the presence of a product of said polymerase chain reaction indicates the presence of a target nucleic acid sequence comprising the variant sequence in said sample.

The sets of primers may comprise only one kind of primer 2, but may also comprise a plurality of different primer 2s, which together with the various primer 1s are capable of amplification of the target nucleic acid sequence.

Such methods may in particular be useful for detecting the presence of at least one of a plurality of variant sequences. For example, if the NOI may be present as a plurality of different variant sequences, such a method may be useful for detecting the presence of at least one of these variant sequences. Frequently such methods do not allow to distinguish one variant sequence from another, but allows distinguishing between the reference NOI sequence and a plurality of variant sequences. This may for example be useful if the presence of any of a plurality of variant sequences may be indicative of a clinical condition or susceptibility to a given treatment regime.

A Kit-of-Parts

The invention also relates to a kit-of-parts a) a blocking oligonucleotide, which may be any of the blocking oligonucleotides described herein below in the section "Blocking oligonucleotide"

b) a set of primers consisting of primer 1 and primer 2, which may be any of the sets of primers described herein below in the section "Set of primers"

The kit-of-parts is in particular useful for performing the methods according to the invention.

In addition to said blocking oligonucleotide and said set of primers, the kit-of-parts may also comprise additional components. For example, the kit-of-parts may further comprise PCR reagents, such as any of the PCR reagents described herein below in the section "PCR reagents". The kit-of-parts may also comprise a detection probe, such as any of the detection probes described herein below in the section "Detection". The detection probe may in particular be a probe allowing for real time detection of the generation of a PCR product.

Blocking Oligonucleotide

The methods of the invention comprise the use of a blocking oligonucleotide. The kit-of-parts of the invention comprise a blocking oligonucleotide and in some embodiments the invention relates to a blocking oligonucleotide. Useful blocking oligonucleotides are described in this section.

In general, the blocking oligonucleotides useful for the present invention comprise a sequence of 10 to 50 nucleotides (referred to as "blocking sequence") into which 2 to 10 hydrophobic nucleotides have been inserted, wherein at least one hydrophobic nucleotide is positioned at the 5' end of said sequence or within 4 nucleotides from the 5' end; and at least one hydrophobic nucleotide is positioned at the 3' end of said sequence or within 4 nucleotides from the 3' end; and wherein the hydrophobic nucleotide is any of the hydrophobic nucleotides described herein below in the section "Hydrophobic nucleotide"; and wherein the blocking sequence is identical to a stretch of the target nucleic acid sequence comprising the reference NOI sequence.

Typically, the internal hydrophobic nucleotides are inserted into the blocking oligonucleotide as bulge insertions. This means that when the blocking oligonucleotide is hybridizing with the reference target sequence, then the two nucleotides positioned on either side of a hydrophobic nucleotide are hybridized to two neighboring nucleotides in the reference target sequence. Preferably, all internal hydrophobic nucleotides are positioned as bulk insertions. Accordingly, the blocking sequence is generally made up of all the nucleotides within the blocking oligonucleotide, which are not hydrophobic nucleotides. In addition, one or two hydrophobic nucleotides may be positioned at the end of the blocking oligonucleotide.

The blocking sequence may for example consist of in the range of 10 to 30 nucleotides, such as in the range of 15 to 25 nucleotides, for example in the range of 10 to 20 nucleotides identical to the reference target sequence.

Since the blocking oligonucleotide is identical to the reference target sequence, then the blocking oligonucleotide contains a sequence which is identical to the reference NOI sequence. This sequence is referred to as reference NOI sequence in the following regardless of whether it is contained in the blocking sequence or in the target nucleic acid sequence.

In one embodiment, the reference NOI sequence is positioned roughly in the middle of the blocking oligonucleotide. Thus, it may be preferred that the blocking oligonucleotide comprise at least 6 nucleotides positioned 5' of the reference NOI sequence. It may also be preferred that the blocking oligonucleotide comprise at least 6 nucleotides positioned 3' of the reference NOI sequence.

In one embodiment of the invention, the blocking oligonucleotide has the following general structure (I):

wherein

N is any nucleotide or nucleotide analogue; and

Z is any of the hydrophobic nucleotides described herein below in the section "hydrophobic nucleotide"; and $SEQ_1$ is a sequence of 4 to 20 nucleotides or nucleotide analogues into which up to 4 hydrophobic nucleotides (Z) may be inserted; and a and b individually are an integer in the range of 0 to 4; and the total number of nucleotides is at least 10; and $(N)_a$-$SEQ_1$-$(N)_b$ is identical to the reference target sequence.

In particular, $SEQ_1$ may be a sequence identical to a stretch of the target nucleic acid sequence comprising the reference NOI sequence.

In one embodiment, the blocking oligonucleotide has the following general structure (II)

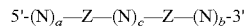

wherein

N is any nucleotide or nucleotide analogue; and

Z is a hydrophobic nucleotide as defined in claim 1; and a and b individually are integers in the range of 0 to 4; and c is an integer in the range of 4 to 20; and a+b+c is at least 10; and $(N)_a$—$(N)_c$—$(N)_b$ is identical to the reference target sequence.

$(N)_c$ may in one embodiment contain the sequence identical to the reference NOI sequence.

In one embodiment, the blocking nucleotide may be a blocking nucleotide of structure (II), wherein a+b+c may be in the range of 10 to 50, preferably in the range of 10 to 20. For example a may be 0 or 1, b may be 0 or 1 and c may an integer in the range of 8 to 20. For example, a may be 0, b may be 1 and c may be an integer in the range of 9 to 19.

In one embodiment of the invention, the blocking oligonucleotide may have the following general structure (III)

wherein

N is any nucleotide or nucleotide analogue; and

Z is a hydrophobic nucleotide as defined in claim 1; and the total number of nucleotides or nucleotide analogues is at least 10; and a and b individually are integers in the range of 0 to 4; and d and e individually are integers in the range of 1 to 19; and a+b+d+e at least 10; and $(N)_a$—$(N)_d$—$(N)_e$—$(N)_b$ is identical to the reference target sequence.

$(N)_d$ may in one embodiment contain the sequence identical to the reference NOI sequence. In other embodiments, $(N)_e$ may contain the sequence identical to the reference NOI sequence.

In one embodiment, the blocking nucleotide may be a blocking nucleotide of structure (III), wherein a+b+d+e is in the range of 10 to 50, preferably in the range of 10 to 20. For example, a may be 0 or 1, b may be 0 or 1, d may be an integer in the range of 4 to 10 and e may be an integer in the range of 4 to 10. For example, a may be 0, b may be 1, d may be an integer in the range of 4 to 10, and e is an integer in the range of 4 to 10. In addition it may be preferred that d and e are roughly the same size, thus d may be the same integer as e+/−2, for example d may be the same integer as e+/−1, for example d may be the same integer as e.

In one embodiment, the blocking oligonucleotide may have the following general structure (IV):

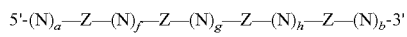

wherein
N is any nucleotide or nucleotide analogue; and
Z is a hydrophobic nucleotide as defined in claim 1; and
a and b individually are integers in the range of 0 to 4; and
f, g and h individually are integers in the range of 1 to 18; and
a+b+f+g+h is at least 10 and at the most 50; and
$(N)_a$—$(N)_f$—$(N)_g$—$(N)_h$—$(N)_b$ is identical to a reference target sequence.

$(N)_f$ may in one embodiment contain the sequence identical to the reference NOI sequence. In other embodiments, $(N)_h$ may contain the sequence identical to the reference NOI sequence. Preferably, however, $(N)_g$ may contain the sequence identical to the reference NOI sequence.

In one embodiment, the blocking nucleotide may be a blocking nucleotide of structure (IV), wherein a+b+f+g+h may be in the range of 10 to 50, preferably in the range of 10 to 20. For example, a may be 0 or 1, b may be 0 or 1, f may be an integer in the range of 3 to 7, g may be an integer in the range of 3 to 7 and h may be an integer in the range of 3 to 7. For example, a may be 0, b may be 1, f may be an integer in the range of 3 to 7, g may be an integer in the range of 3 to 7 and h may be an integer in the range of 3 to 7.

In addition, it may be preferred that f, g and h are roughly the same size, thus f and g may be the same integer as h+/−2, for example f and g may be the same integer as h+/−1, for example f and g may be the same integer as h.

A blocking oligonucleotide having the following general structure (V)

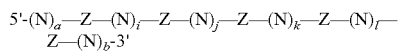

wherein
N is any nucleotide or nucleotide analogue; and
Z is a hydrophobic nucleotide as defined in claim 1; and
a and b individually are integers in the range from 0 to 4; and
j, k and l individually are integers in the range from 1 to 17; and
a+b+i+j+k+l is at least 10 and at the most 50; and
$(N)_a$—$(N)_i$—$(N)_j$—$(N)_k$—$(N)_l$—$(N)_b$ is identical to a reference target sequence.

$(N)_j$ oder $(N)_l$ may in one embodiment contain the sequence identical to the reference NOI sequence. Preferably however $(N)_j$ oder $(N)_k$ may contain the sequence identical to the reference NOI sequence.

In one embodiment, the blocking nucleotide may be a blocking nucleotide of structure (V), wherein a+b+i+j+k+l may be in the range of 10 to 50, preferably in the range of 10 to 20. For example, a may be 0 or 1, b may be 0 or 1, i may be an integer in the range of 2 to 5, j may be an integer in the range of 2 to 5, k may be an integer in the range of 2 to 5 and l may be an integer in the range of 2 to 5. For example, a may be 0, b may be 1, i may be an integer in the range of 2 to 5, j may be an integer in the range of 2 to 5, k may be an integer in the range of 2 to 5 and l may be an integer in the range of 2 to 5.

In addition, it may be preferred that i, j, k and l are roughly the same size, thus i, j and k may be the same integer as l+/−2, for example i, j and k may be the same integer as l+/−1, for example i, j and k may be the same integer as l.

In one embodiment, the blocking oligonucleotide may have the following general structure (VI)

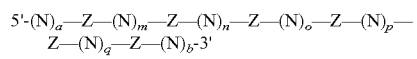

wherein
N is any nucleotide or nucleotide analogue; and
Z is a hydrophobic nucleotide as defined in claim 1; and
a and b individually are integers in the range of 0 to 4; and
m, n, o, p and q individually are integers in the range of 1 to 16; and
a+b+m+n+o+p+q is at least 10 and at the most 50; and
$(N)_a$—$(N)_m$—$(N)_n$—$(N)_o$—$(N)_p$—$Z$—$(N)_q$—$(N)_b$ is identical to a reference target sequence.

$(N)_m$, $(N)_n$, $(N)_p$ or $(N)_q$ may in one embodiment contain the sequence identical to the reference NOI sequence. Preferably, however, $(N)_o$ may contain the sequence identical to the reference NOI sequence.

In one embodiment, the blocking nucleotide may be a blocking nucleotide of structure (VI), wherein a+b+m+n+o+p+q may be in the range of 10 to 50, preferably in the range of 10 to 20. For example, a may be 0 or 1, b may be 0 or 1, m may be an integer in the range of 2 to 4, n may be an integer in the range of 2 to 4, o may be an integer in the range of 2 to 4, p may be an integer in the range of 2 to 4 and q may be an integer in the range of 2 to 4. For example, a may be 0, b may be 1, m may be an integer in the range of 2 to 4, n may be an integer in the range of 2 to 4, o may be an integer in the range of 2 to 4, p may be an integer in the range of 2 to 4 and q may be an integer in the range of 2 to 4.

In addition, it may be preferred that m, n, o, p and q are roughly the same size, thus m, n, o and p may be the same integer as q+/−1, for example m, n, o and p may be the same integer as q.

In relation to blocking oligonucleotides of structures (I), (II), (III), (IV), (V) or (VI) a may be an integer in the range of 0 to 3, for example in the range of 0 to 2, preferably a is an integer in the range of 0 to 1. In particular a may be 0.

In relation to blocking oligonucleotides of structures (I), (II), (III), (IV), (V) or (VI) b may be an integer in the range of 0 to 3, for example in the range of 0 to 2, preferably b may be 0 or b may be 1.

Set of Primers

The methods of the invention involve use of a set of primers and the kit-of-parts according to the invention comprise a set of primers.

The set of primers consists of primer 1 and primer 2, wherein the set of primers together are capable of priming amplification of a target nucleic acid sequence comprising a variant sequence. A pair of primer 1 and primer 2 is capable of priming amplification of said target nucleic acid sequence if said primers are used in a PCR reaction in the presence of said target nucleic acid sequence and FOR reagents.

One of the primers can be considered the forward primer, whereas the other primer can be considered the reverse primer when used in a PCR reaction.

In order to render the set of primers specific for the target nucleic acid sequence comprising the variant sequence, then primer 1 comprises a sequence, which is identical to a stretch of the target nucleic acid sequence comprising the variant sequence.

In order to provide distinction between the variant sequence and the reference NOI sequence, primer 1 in general comprise a sequence identical to the variant sequence. In particular the 3' end of primer 1 may comprise a sequence of at least 15 nucleotides, which is identical to a stretch of the target nucleic acid sequence comprising the variant sequence except for up to one mismatch.

The exact length of the sequence of primer 1 identical to a stretch of the target nucleic acid sequence may be adjusted in order to arrive at a primer having a melting temperature useful for PCR amplification. The melting temperature of a primer is dependent on several factors, but in particular on the GC content and the length. Because primer 1 should be identical to a stretch of the target nucleic acid sequence comprising the variant sequence (see more details below) there are restrictions to the specific sequence of the primer. Accordingly, the melting temperature may in particular be adjusted by adjusting the length of the primer. The skilled person is well capable of designing a primer with a suitable melting temperature and useful software to this end is publicly available.

Thus, the 3' end of primer 1 may comprise a sequence of at least 15 nucleotides, for example at least 20 nucleotides, such as at least 25 nucleotides, for example in the range of 15 to 50 nucleotides, such as in the range of 20 to 40 nucleotides, which is identical to the target nucleic acid sequence comprising the variant sequence except for up to one mismatch.

In one embodiment of the invention, primer 1 consists of a sequence of at least 15 nucleotides, for example at least 20 nucleotides, such as at least 25 nucleotides, for example in the range of 15 to 50 nucleotides, such as in the range of 20 to 40 nucleotides, which is identical to the target nucleic acid sequence comprising the variant sequence except for up to one mismatch.

As mentioned above the sequence of primer 1 comprises or consists of a sequence identical to the target nucleic acid sequence comprising the variant sequence except for up to one mismatch. In some embodiments, it is preferred that there is one mismatch, as this may even further improve the specificity of the assay. In particular said mismatch may be positioned at position 2, 3 or 4 from the 3' end of primer 1.

In order to provide the best distinction between the variant sequence and the reference target sequence, it is preferred that the most 3' nucleotide(s) of primer 1 are identical to the variant sequence. Thus, in such an embodiment the most 3' nucleotide(s) of primer 1 are different to the reference NOI sequence. In this way, even if the primer 1 should hybridise to the reference target sequence, then the very 3' end of primer 1 will not hybridise and thus the primer 1 will not serve as a good primer to PCR amplification of a sequence comprising the reference NOI sequence.

The sequence of primer 1 may be designed according to the nature of the variant sequence. In one preferred embodiment of the invention, the variant sequence is a single nucleotide variant. Thus, the difference between the target nucleic acid sequence comprising the variant sequence and the reference target sequence is only 1 nucleotide. For the sake of simplicity this nucleotide is referred to as single nucleotide variant in the following.

It is preferred that the primer 1 comprises a sequence identical to said single nucleotide variant and to the sequences positioned immediately 5' of said single nucleotide variant in the target nucleic acid sequence comprising the variant sequence except for up to one mismatch.

It is preferred that the primer 1 comprises a sequence identical to said single nucleotide variant and to the sequences positioned immediately 5' of said single nucleotide variant in the target nucleic acid sequence except for up to one mismatch. Thus, primer 1 may comprise or consist of a sequence of at least 15 nucleotides, for example at least 20 nucleotides, such as at least 25 nucleotides, for example in the range of 15 to 50 nucleotides, such as in the range of 20 to 40 nucleotides, which is identical to the single nucleotide variant and the target nucleic acid sequence positioned immediately 5' of the single nucleotide variant in the target nucleic acid sequence, except for up to one mismatch.

In one embodiment of the invention, the variant sequence consists of more than one consecutive variant nucleotides. Thus, the difference between the target nucleic acid sequence comprising the variant sequence and the reference target sequence is a stretch of more than one consecutive nucleotides.

In such embodiments, the most 3' nucleotides of primer 1 may be identical to the variant nucleotides.

In one embodiment of the invention, the variant sequence consists of an insertion of one or more nucleotides. Thus, the difference between the target nucleic acid sequence comprising the variant sequence and the reference target sequence is the target nucleic acid sequence comprising the variant sequence comprises a stretch of one or more nucleotides not present in the reference target sequence.

In such embodiments, the most 3' nucleotides of primer 1 may be identical to at least the nucleotide(s) positioned at 5' end of the insertion. If the insertion is only a few nucleotides, then the most 3' nucleotides of primer 1 may be identical to all the inserted nucleotides. This may for example be the case when the insertion is insertion of 5 or fewer nucleotides.

In one embodiment of the invention, the variant sequence consists of a deletion of one or more nucleotides. Thus, the difference between the target nucleic acid sequence comprising the variant sequence and the reference target sequence is that the reference target sequence comprises a stretch of one or more nucleotides not present in the target nucleic acid sequence comprising the variant sequence.

In such embodiments, the most 3' nucleotides of primer 1 may be identical to at least one nucleotide positioned immediately 3' of the deletion in the target nucleic acid sequence.

In addition, in order to provide good distinction between the target nucleic acid sequence comprising the reference NOI sequence or the variant sequence, then primer 1 may in preferred embodiments contain a consecutive sequence identical to a consecutive sequence of the blocking oligonucleotide. In that way primer 1 binding to the reference target sequence may be further inhibited, because the blocking oligonucleotide will occupy the part of the reference target sequence to which primer 1 potentially could bind. Thus, primer 1 may comprises a sequence which is identical to a consecutive sequence of the blocking sequence of at least 3 nucleotides, preferably of at least 6 nucleotides except for up to one mismatch.

The sequence of primer 1, which is identical to a consecutive sequence of the blocking sequence except for the up to one mismatch may be positioned at any useful position within primer 1, but typically it is positioned immediately 5' to the sequence identical to the variant sequence.

Primer 2 may be any primer, which together with primer 1 is capable of priming amplification of the target nucleic acid sequence comprising the variant sequence. Thus, there is more freedom for the skilled person to design primer 2. The skilled person will be well able to design primers with an adequate melting temperature, normally a melting temperature similar to the melting temperature of primer 1. Furthermore, primer 2 must comprise or even consist of a sequence of at least 15 nucleotides, which is complementary to a consecutive sequence of the target nucleic acid sequence. Primer 2 may for example comprise or even consist of a sequence of at least 20 nucleotides, such as at least 25 nucleotides, for example in the range of 15 to 50 nucleotides, such as in the range of 20 to 40 nucleotides, which is complementary to a consecutive sequence of the target nucleic acid sequence.

Figure 2:
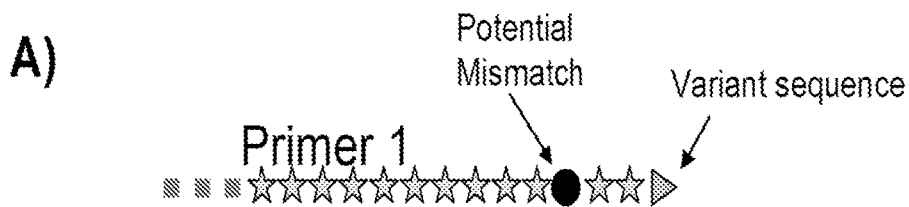
FIG. 2 illustrates an example of how primer 1 shown in A) and the blocking oligonucleotide shown in B) may be designed. In this example, there is a very large overlap between primer 1 and the blocking oligonucleotide.
Figure 2:
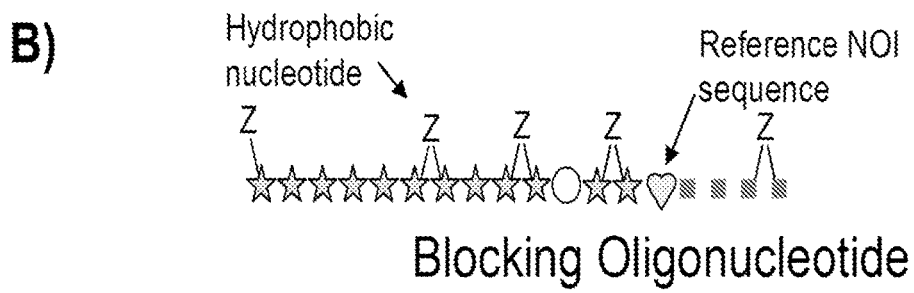
Figure 3:
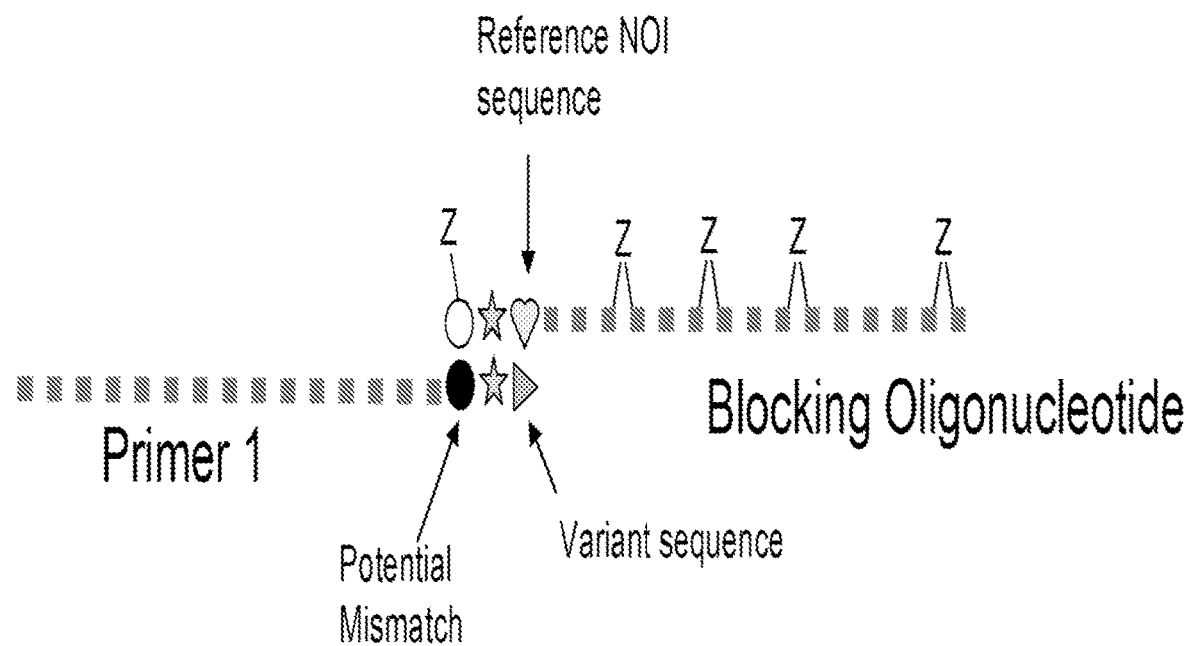
FIG. 3A illustrates an example of how primer 1 and the blocking oligonucleotide may be designed. In this example, there is a minimal overlap between primer 1 and the blocking oligonucleotide.
FIG. 3B shows sequence examples of primer 1 and blocking oligonucleotide combinations for testing the mutations in the target genes as indicated in the figure.

Specific examples of useful ways of designing the blocking oligonucleotide and primer 1 are described herein in Example 1 and illustrated in FIGS. 1-3.

Variant Sequence

The variant sequence may be any sequence, which differs between two sequences. Frequently, the variant sequence is a mutant sequence, e.g. a sequence which differs from the wild type sequence. The variant sequence can however also be a polymorphic sequence or any other sequence which differs from a reference NOI sequence.

The variant sequence may consist of at least one, such as 1, for example 2, such as 3, for example 4, such as 5, for example 6, such as 7, for example 8, such as 9, for example 10, such as from 10 to 20, for example from 20 to 50, such as more than 50 nucleotides.

In preferred embodiments of the invention, the variant sequence is a single nucleotide mutation or a single nucleotide polymorphism (SNP).

The variant sequence may be change of one or more nucleotides for one or more other nucleotides compared to the reference target sequence. Furthermore, the term variant sequence may be a deletion or insertion of nucleotides within a nucleic acid, for example deletion or insertion of nucleotides compared to the reference target sequence.

The target nucleic acid sequence may comprise a polymorphic site (see details herein below) and thus the reference target sequence may comprise one polymorphism, whereas the "variant sequence" may constitute another polymorphism.

In one embodiment, the reference target sequence is a wild type sequence, i.e. the most frequently naturally occurring sequence, whereas the variant sequence comprises one or more mutations compared to said wild type sequence. Accordingly, a variant sequence according to the present invention may in one embodiment be a polymorphism, such as a single nucleotide polymorphism (SNP). For example, the polymorphism may be indicative of a specific DNA profile. Knowledge of a specific DNA profile may for example be employed to identify an individual. For example, a specific DNA profile may be employed to identify a criminal or a potentially criminal or to identify a dead body or part of a dead body. Furthermore, a specific DNA profile may be employed to determine relationship between individuals, for example parents-child relationship or more distant relationships. Relationship may also be relationship between different species or different population of a given species.

In one embodiment, the mutation may be indicative of a clinical condition or the mutation may be indicative of increased risk of a clinical condition.

Said clinical condition may for example be selected from the group consisting of neoplastic diseases, neurodegenerative diseases, cardiovascular diseases and metabolic disorders including diabetes.

Furthermore, the mutation may be indicative of a specific response to a predetermined drug treatment. For example, the mutation may be indicative of whether an individual will respond positively to said drug treatment or whether an individual can not tolerate a specific drug treatment.

The variant sequence may be positioned in a particular gene, a gene segment, a micro satellite or any other DNA sequence. Furthermore the variant sequence may be positioned in a mRNA, miRNA or any other RNA sequence. Of particular interest is the detection of particular DNAs, which may be of eukaryotic, prokaryotic, Archae or viral origin. Importantly, the invention may assist in the diagnosis and/or genotyping of various infectious diseases by assaying for particular sequences known to be associated with a particular microorganism.

Detection

The methods of the invention involve detecting a product of a polymerase chain reaction (PCR). Many methods are available to detect the presence of a PCR product, and any available method may be used. Thus, the invention is not restricted to a particular method for detecting whether a PCR product is generated.

It may be preferred to use a method, which can detect generation of a PCR product in real time such as quantitative real-time PCR in which either non-specific fluorescent dyes that intercalate with double-stranded DNA or sequence-specific DNA detection probes are used to quantitate the amplified DNA.

Frequently said detection probe is labelled with a detectable label, e.g. with a fluorescent label.

In one embodiment, the detection probe is labelled with a signalling pair consisting of two members. Thus, the detection probe may be an oligonucleotide comprising a sequence which is identical to or complementary to a consecutive sequence of the target nucleic acid sequence, wherein said oligonucleotide comprises a signalling pair.

The signalling pair may in particular consist of two members providing different signals depending on the distance between the members. For example, the signalling pair may consist of a fluorophore and a quencher, capable of quenching fluorescence of said fluorophore. The signalling pair may also consist of two fluorophores capable of fluorescence resonance energy transfer (FRET).

Examples of useful detection probes include TaqMan probes and molecular beacons.

In one embodiment, the detection probe may comprise one or more hydrophobic nucleotides, such as any of the hydrophobic nucleotides described herein below in the section "Hydrophobic nucleotides". For example, the detection probe may be a double stranded oligonucleotide or an oligonucleotide comprising a double stranded part. Said double strand may comprise hydrophobic nucleotides, for example at least two hydrophobic nucleotides positioned essentially opposite of each other one on each strand of the double strand. In addition, said detection probe may comprise a signalling pair as described above. Thus, the detection probe may be a duplex of oligonucleotides capable of hybridising to each other, wherein one strand of said duplex is identical to a consecutive sequence of the target nucleic acid, and wherein each strand of said duplex contains a hydrophobic nucleotide and a member of a signalling pair, wherein said hydrophobic nucleotides are positioned opposite of each other, and said members of the signalling pair are positioned opposite of each other, when said oligonucleotides are hybridised to each other.

Thus, the detection probe may be any of the oligonucleotides or oligonucleotide analogues containing a signalling pair, e.g. any of the stemless beacons described in international patent application WO2007/104318, which is incorporated by reference herein.

Non-limiting examples of useful detection probes include HydrolEasy and EasyBeacons.

Other methods may be used with the present invention for the detection and/or evaluation of either single or multiple PCR-products. Those include, but are not limited to: Gel documentation of electrophoresis-separated PCR products including Southern blotting for detection of the target nucleic acid sequence(s) using specific hybridization probes; mutant-enriched PCR using selective restriction enzyme digestion enabling specifically amplification of the variant sequence(s); Next-Generation Sequencing and DNA microarray profiling in order to obtain extended sequence information from the PCR products generated.

Hydrophobic Nucleotide

The blocking oligonucleotide according to the invention comprises at least one hydrophobic nucleotide. A hydrophobic nucleotide according to the present invention has the following structure:

X—Y-Q wherein

X is a nucleotide or nucleotide analogue or a backbone monomer unit capable of being incorporated into the backbone of a nucleic acid, Q is an intercalator, which is not taking part in Watson-Crick hydrogen bonding; and Y is a linker moiety linking said nucleotide or nucleotide analogue or backbone monomer unit and said intercalator.

The backbone monomer unit X may be any of the backbone monomer units described herein below in the section "Backbone monomer unit.

The intercalator Q may be any of the intercalators described herein below in the section "Intercalator".

Intercalator

The term intercalator according to the present invention covers any molecular moiety comprising at least one essentially flat conjugated system, which is capable of co-stacking with nucleobases of a nucleic acid. Preferably an intercalator according to the present invention essentially consists of at least one essentially flat conjugated system, which is capable of co-stacking with nucleobases of a nucleic acid.

An intercalator comprises at least one π (phi) electron system, which according to the present invention can interact with other molecules comprising a π electron system. These interactions can contribute in a positive or negative manner to the hydrophobic interactions of said intercalators. Hunter and Sanders (1990) *J. Am Chem. Soc.* 112: 5525-5534, have proposed a range of different orientations and conditions where two π electron systems can interact positively with each other.

Preferably, the intercalator comprises a chemical group selected from the group consisting of polyaromates and heteropolyaromates an even more preferably the intercalator essentially consists of a polyaromate or a heteropolyaromate. Most preferably the intercalator is selected from the group consisting of polyaromates and heteropolyaromates.

Polyaromates or heteropolyaromates according to the present invention may consist of any suitable number of rings, such as 1, for example 2, such as 3, for example 4, such as 5, for example 6, such as 7, for example 8, such as more than 8. Furthermore polyaromates or heteropolyaromates may be substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl, carbonyl and amido.

Accordingly, an intercalator Q according to the present invention may for example be an intercalator selected from the group consisting of phenanthroline, phenazine, phenanthridine, anthraquinone, pyrene, anthracene, napthene, phenanthrene, picene, chrysene, naphtacene, acridones, benzanthracenes, stilbenes, oxalo-pyridocarbazoles, azidobenzenes, porphyrins, psoralens and any of the aforementioned intercalators substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl and/or amido.

Preferably, the intercalator is selected from the group consisting of phenanthroline, phenazine, phenanthridine, anthraquinone, pyrene, anthracene, napthene, phenanthrene, picene, chrysene, naphtacene, acridones, benzanthracenes, stilbenes, oxalo-pyridocarbazoles, azidobenzenes, porphyrins and psoralens.

In a preferred embodiment, the intercalator is selected from the group consisting of phenanthroline, phenazine, phenanthridine, anthraquinone, pyrene, anthracene, phenanthrene, chrysene, naphtacene, benzanthracenes, stilbenes and porphyrins In another preferred embodiment the intercalator comprises pyrene or pyrido[3',2':4,5]thieno[3,2-d]pyrimidin-4 (1H)-one or 7,9-dimethyl-pyrido[3',2',4,5]thieno[3,2-d]pyrimidin-4(3H)-one. The intercalator may also consist of pyrene or pyrido[3',2':4,5]thieno[3,2-d]pyrimidin-4(1H)-one, or 7,9-dimethyl-pyrido[3',2',4,5]thieno[3,2-d]pyrimidin-4(3H)-one.

More preferably, the intercalator may be selected from the group of intercalators comprising one of the structures as indicated herein below:

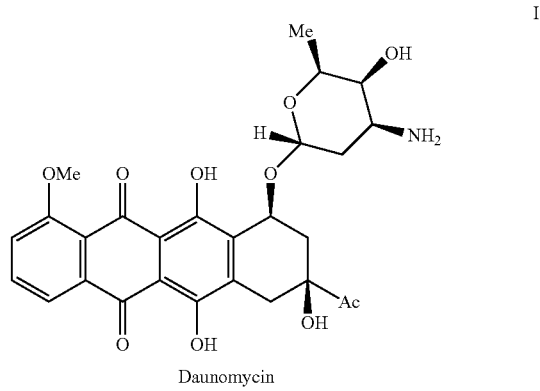

Daunomycin

-continued
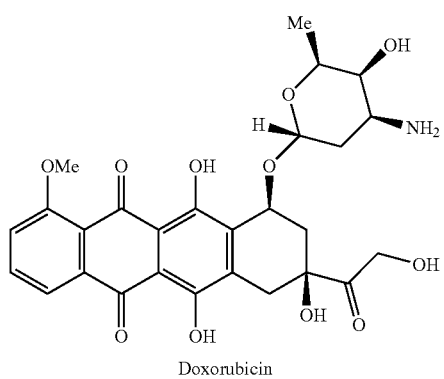
Doxorubicin
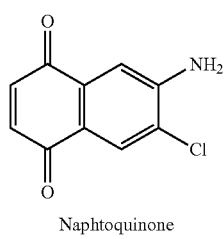
Naphtoquinone
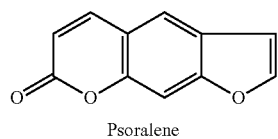
Psoralene
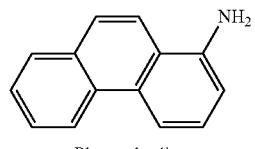
Phenanthroline
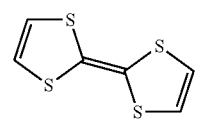
1,3-Dithiole,
2-(1,3-dithiol-2-ylidene)-
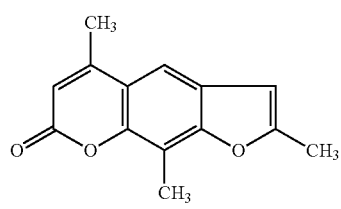
Trimethylpsoralene
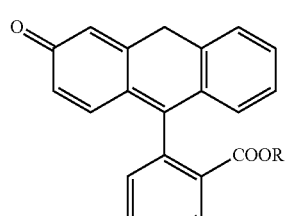
Fluorescein derivative
-continued
Acridine derivative
Acradine
Acradinium
Pyrene
Napthalene
Antracene
Phenanthrane
Triphenylene
6H-Indolo[2,3-b]quinoxaline

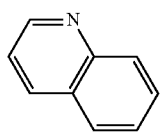
Quinoline
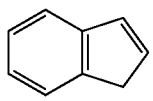
1H-Indene
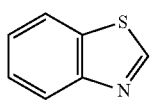
Benzothiazole
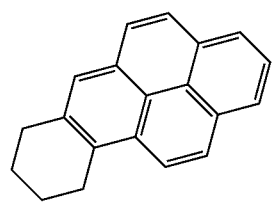
7,8,9,10-Tetrahydrobenzo[a]pyrene
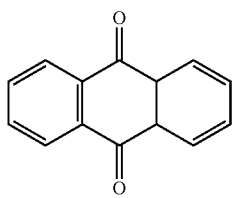
9,10-Anthracenedione
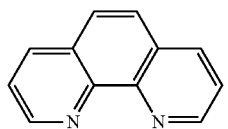
1,10-Phenanthroline
9bH-Phenalene
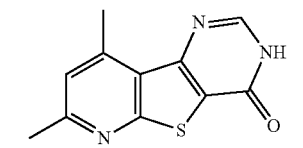
Pyrido[3′,2′:4,5]thieno[3,2-d]pyrimidin-4(1H)-one, 7,9-dimethyl-
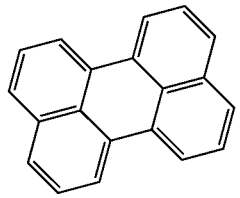
Perylene
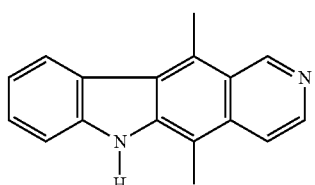
6H-Pyrido[4,3-b]carbazole, 5,11-dimethyl-
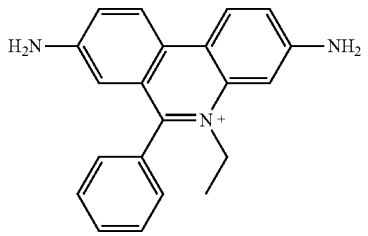
Phenanthridinium, 3,8-diamino-5-ethyl-6-phenyl-
1H-Benz[de]isoquinoline-1,3(2H)-dione
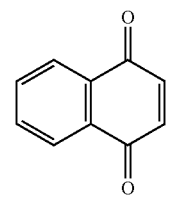
1,4-Naphthalenedione
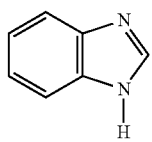
1H-Benzimidazole
1H-Indole -continued

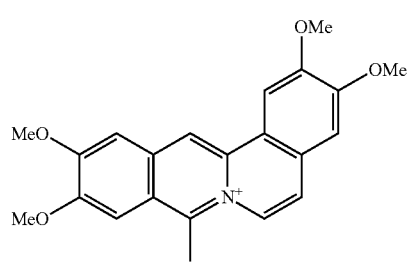

Dibenzo[a,g]quinolizinium,
2,3,10,11-tetramethoxy-8-methyl-

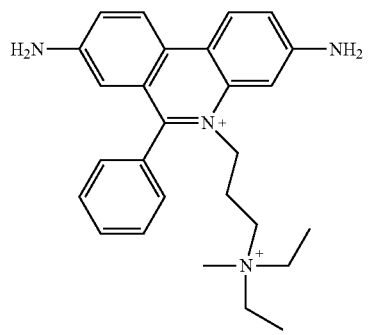

Phenanthridinium, 3,8-diamino-5-
[3-(diethylmethylammonio)propyl]-6-phenyl-

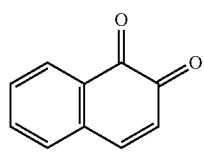

1,2-Naphthalenedione

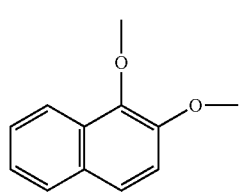

Naphthalene, 1,2-dimethoxy-

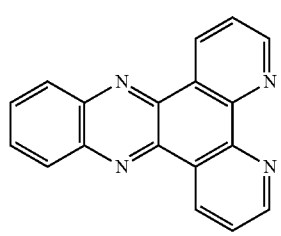

Dipyrido[3,2-a:2',3'-c]phenazine

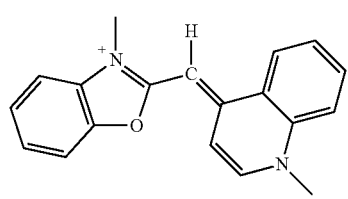

Quinolinium, 4-[(3-ethyl-2(3H)-
benzoxazolylidene)methyl]-1-methyl-

-continued

XXXIV

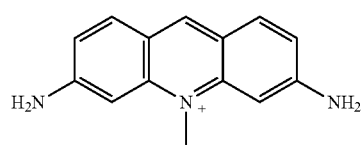

Acridine, 6-amino-3,10-
dihydro-3-imino-10-methyl-

XXXV

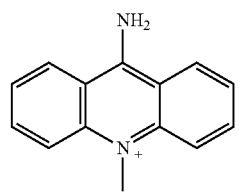

Acridinium,
9-amino-10-methyl-

XXX

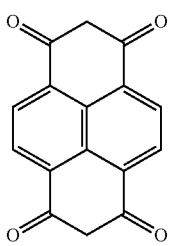

1,3,6,8(2H,7H)-Pyrenetetrone

XXXVII

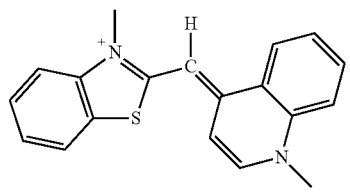

Quinolinium, 1-methyl-4-
[(3-methyl-2(3H)-benzothiazolylidene)methyl]-

XXXVIII

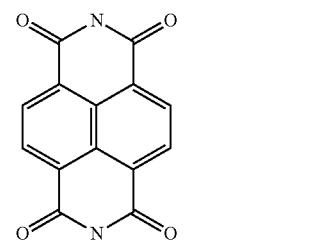

Benzo[lmn][3,8]phenanthroline-
1,3,6,8(2H,7H)-tetrone

XXXIX

2H-1-Benzopyran-2-one

XL

XLI

XLIII

XLII

XLIV

XLV

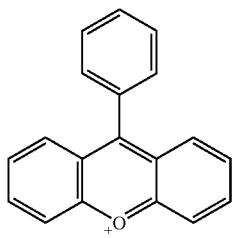

Xanthylium, 9-phenyl-

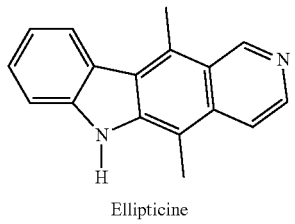

Ellipticine

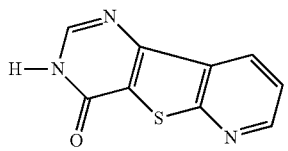

Pyrido[3',2':4,5]thieno
[3,2-d]pyrimidin-
4(1H)-one

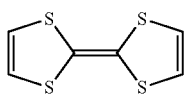

Fulvalene

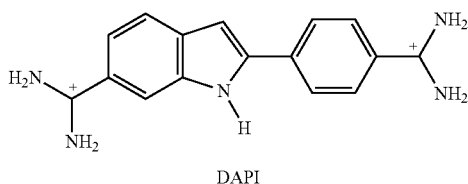

DAPI

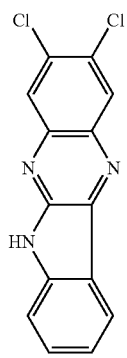

and optionally, but not so preferable derivatives thereof. Even more preferably the intercalator may be selected from the group of intercalators consisting of the intercalator structures above numbered V, XII, XIV, XV, XVII, XXIII, XXVI, XXVIII, XLVII, LI and LII as well as derivatives thereof, preferably from the group of intercalators consisting of the intercalator structures above numbered V, XII, XIV, XV, XVII, XXIII, XXVI, XXVIII, XLVII, LI and LII.

Most preferably, the intercalator is selected from the group of intercalator structures above numbered XII, XIV, XVII, XXIII, LI as well as derivatives thereof, preferably from the group of intercalator structures above numbered XII, XIV, XVII, XXIII and LI.

The above list of examples is not to be understood as limiting in any way, but only as to provide examples of possible structures of intercalators. In addition, the substitution of one or more chemical groups on each intercalator to obtain modified structures is also included in the present invention.

In one embodiment of the invention, the intercalator may be any of the intercalators described in international patent application WO03/052132 in the section "intercalator" on p. 46, l. 10-p. 54, l. 13.

In a preferred embodiment the intercalator is pyrene. In another preferred embodiment the intercalator is

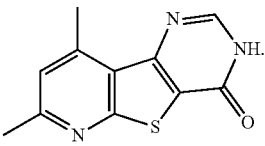 [SMILES: Cc1cc(C)c2c(n1)sc1c(=O)[nH]cnc12]

Backbone Monomer Unit

The backbone monomer unit of a nucleotide or a nucleotide analogue according to the present invention is the part of the nucleotide, which is involved in incorporation into the backbone of a nucleic acid or a nucleic acid analogue. The backbone monomer unit (X) is preferably covalently linked to a linker (Y), which is covalently linked to the intercalator. Any suitable backbone monomer unit may be employed for incorporating intercalator into the oligonucleotide analogues according to the present invention. Any sort of linker linking said backbone monomer unit and said intercalator could also be employed. In addition, the backbone monomer unit may comprise one or more leaving groups, protecting groups and/or reactive groups, which may be removed or changed in any way during synthesis or subsequent to synthesis of an oligonucleotide or oligonucleotide analogue comprising said backbone monomer unit.

The backbone monomer unit may be any suitable backbone monomer unit. In one embodiment of the present invention, the backbone monomer unit may for example be selected from the group consisting of the backbone monomer units of DNA, RNA, PNA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, α-L-RNA or α-D-RNA, β-D-RNA and mixtures thereof and hybrids thereof, as well as phosphorous atom modifications thereof, such as but not limited to phosphorothioates, methyl phospholates, phosphoramidates, phosphorodithiates, phosphoroselenoates, phosphotriesters and phosphoboranoates. In addition non-phosphorous containing compounds may be used for linking to nucleotides such as but not limited to methyliminomethyl, formacetate, thioformacetate and linking groups comprising amides.

Below is depicted a range of different backbone monomer units of nucleotides and nucleotide analogues useful with the present invention, and how they are connected to the nucleobases via linkers that are attached at one or two positions of the backbone monomer unit:

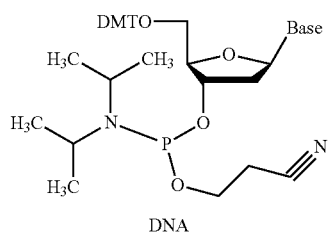
DNA

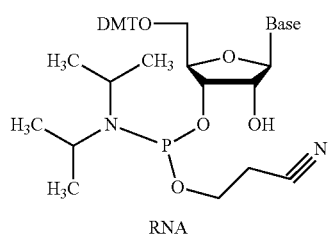
RNA

Examples of Oligomers of DNA, RNA & PNA:

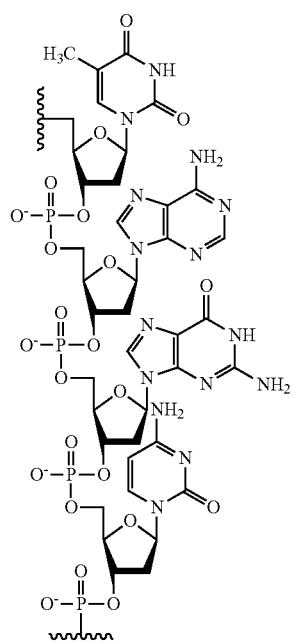

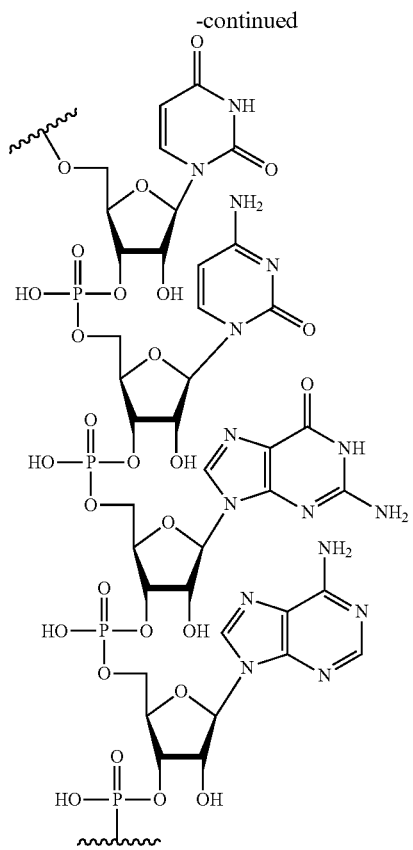

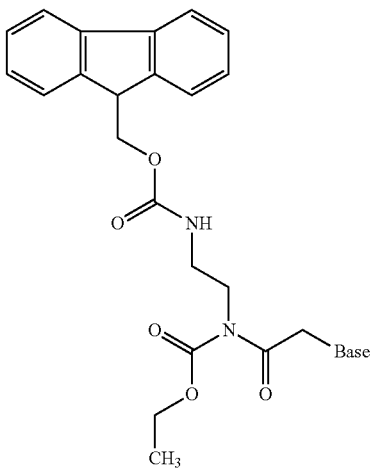

-continued
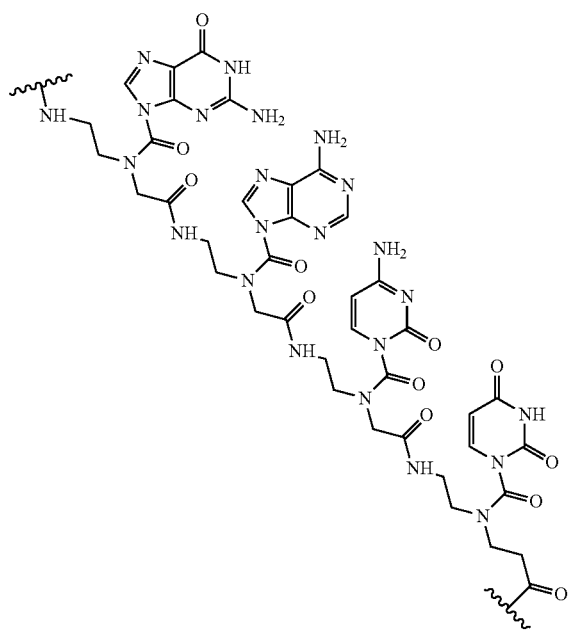
Examples of Oligomers of Some Analogues:
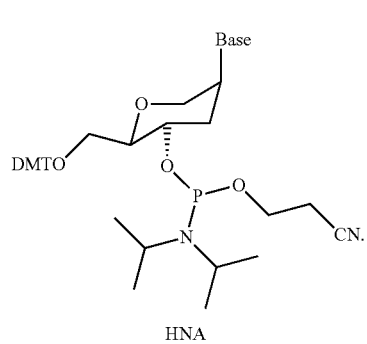
HNA
Ref. Van Aerschot, A. et al.
*Angew. Chem. Int. Ed., Engl.,* 1995,
34, 1338-1339
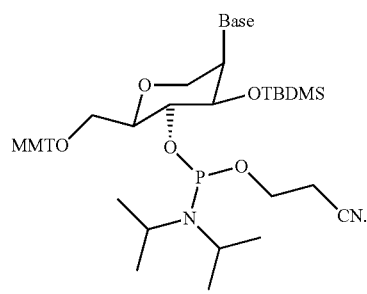
MNA
Ref. Hossain N. et al.
*J. Org. Chem.,* 1998, 63, 1574-1582
-continued
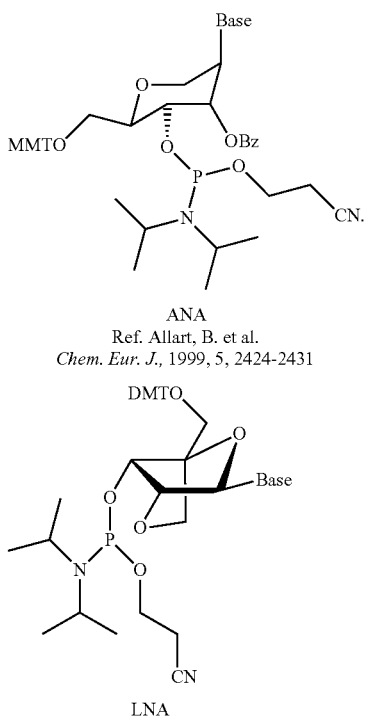
ANA
Ref. Allart, B. et al.
*Chem. Eur. J.,* 1999, 5, 2424-2431
LNA
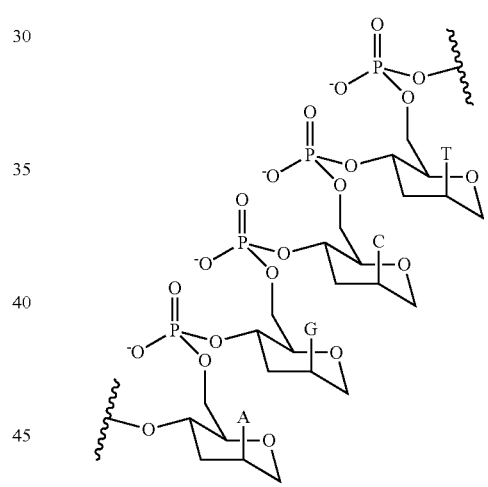
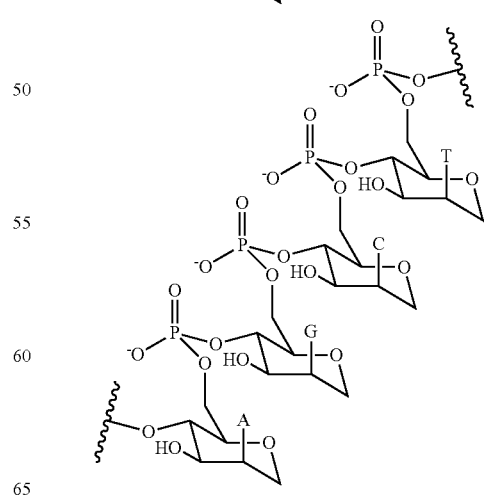

33
-continued
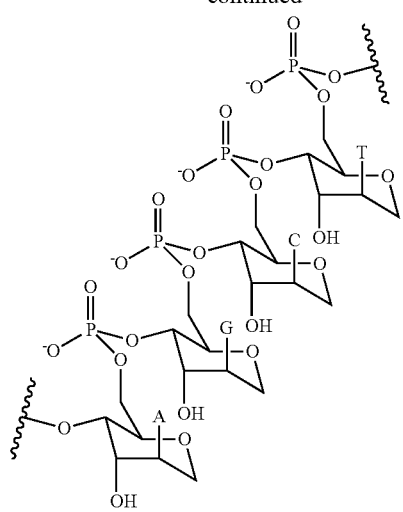
Koshkin, A. A. et al. *Tetrahedron*,
1998, 54, 3607-3630
Ref: Singh, S. K. et al. *Chem. Commun.*,
1998, 455-456
Obika. S. et al. *Tetrahedron lett.*,
1997, 38. 8735-8738
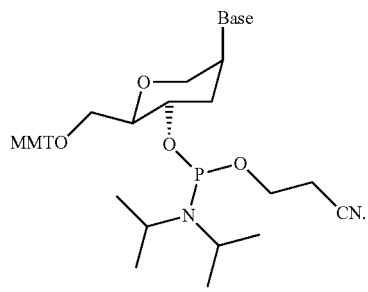
Cyclohexanyl-NA (CNA)
Ref: Maurinsh, Y.; et al.
*Chem. Eur. J.*, 1999, 2139-2150
34
-continued
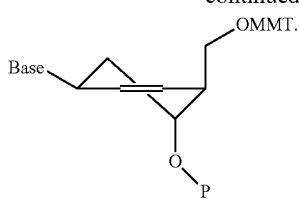
Cyclohexenyl-Na (CeNA)
Ref: Wang, J.; et al.
*J. Am. Chem. Soc*,
2000, 8595-8602
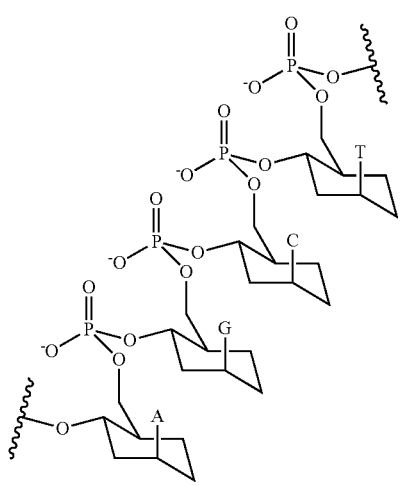
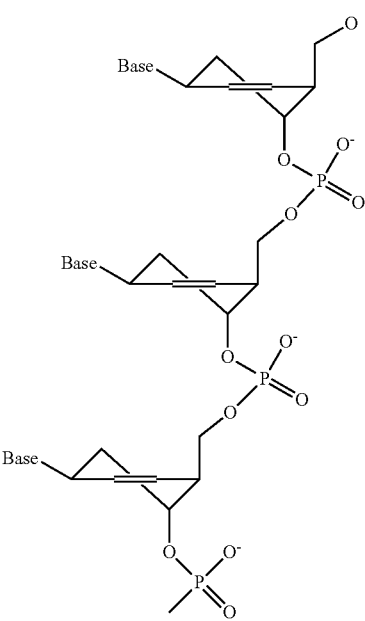

-continued
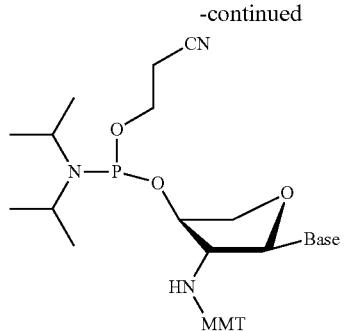
(2'-NH)-TNA
Ref.: Wu, X. et al., Org. Lett., 202, 4, 1279-1282
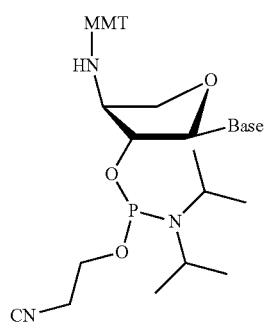
(3'-NH)-TNA
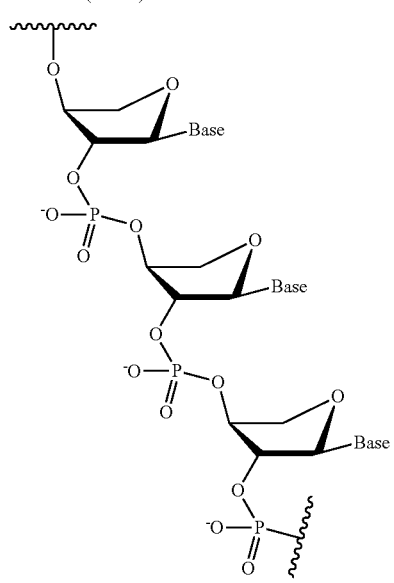
TNA
Ref.: Wu, X. et al., Org. Lett., 2002, 4, 1279-1282
Section of a Nucleic Acid of the Respective Analogues
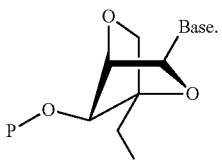
α-L-Ribo-LNA
Ref: Rajwanshi, V. K. et al.
Chem. Commun., 1999, 1395-1396
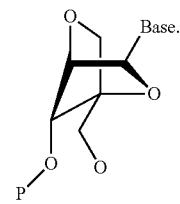
α-L-Xylo-LNA
Ref: Rajwanshi, V. K. et al.
Angew. Chem. Int. Ed., 2000, 1656-1659
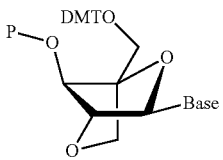
β-D-Xylo-LNA
Ref: Rajwanshi, V. K. et al.
Chem. Commun., 1999, 1395-1396
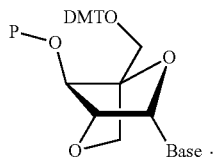
α-D-Ribo-LNA
Ref: Rajwanshi, V. K. et al.
Angew. Chem. Int. Ed., 2000, 1656-1659
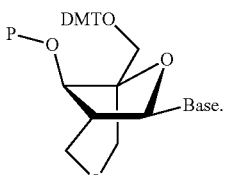
[3.2.1]-LNA
Ref: Wang, G.; et al.
Tetrahedron, 1999, 7707-2724
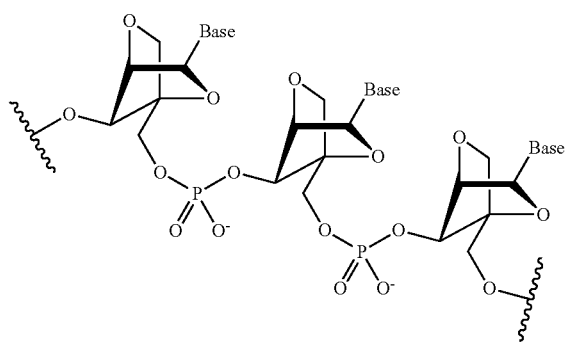
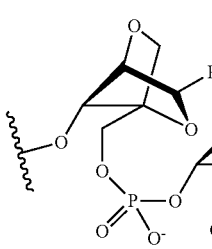
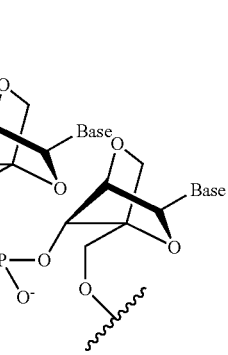

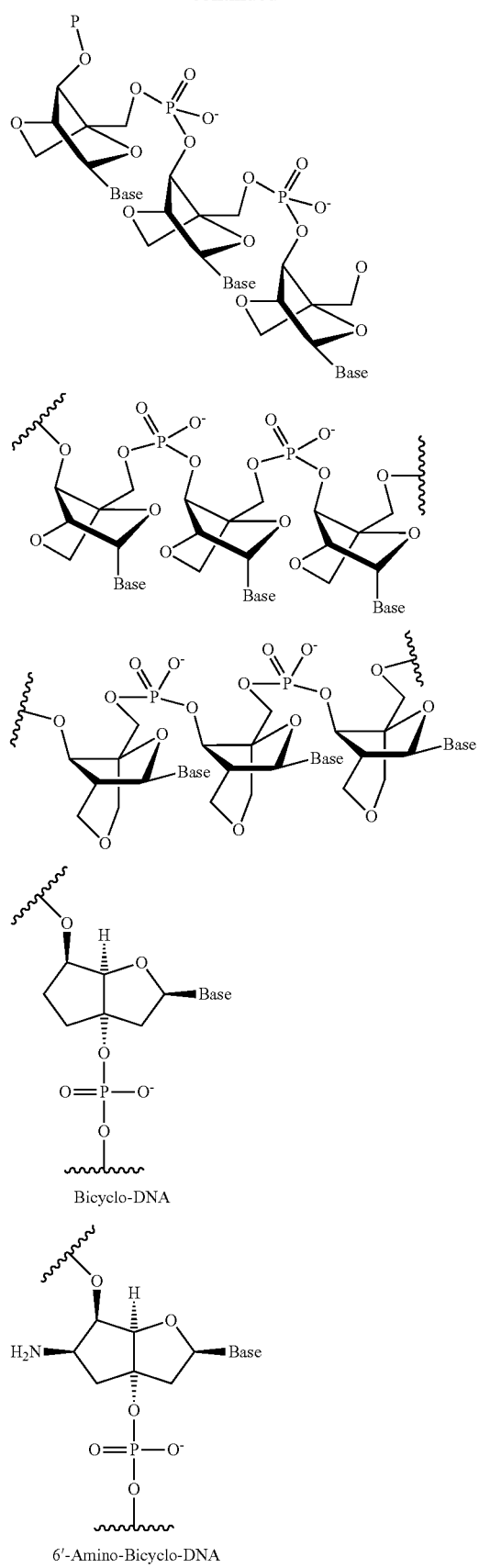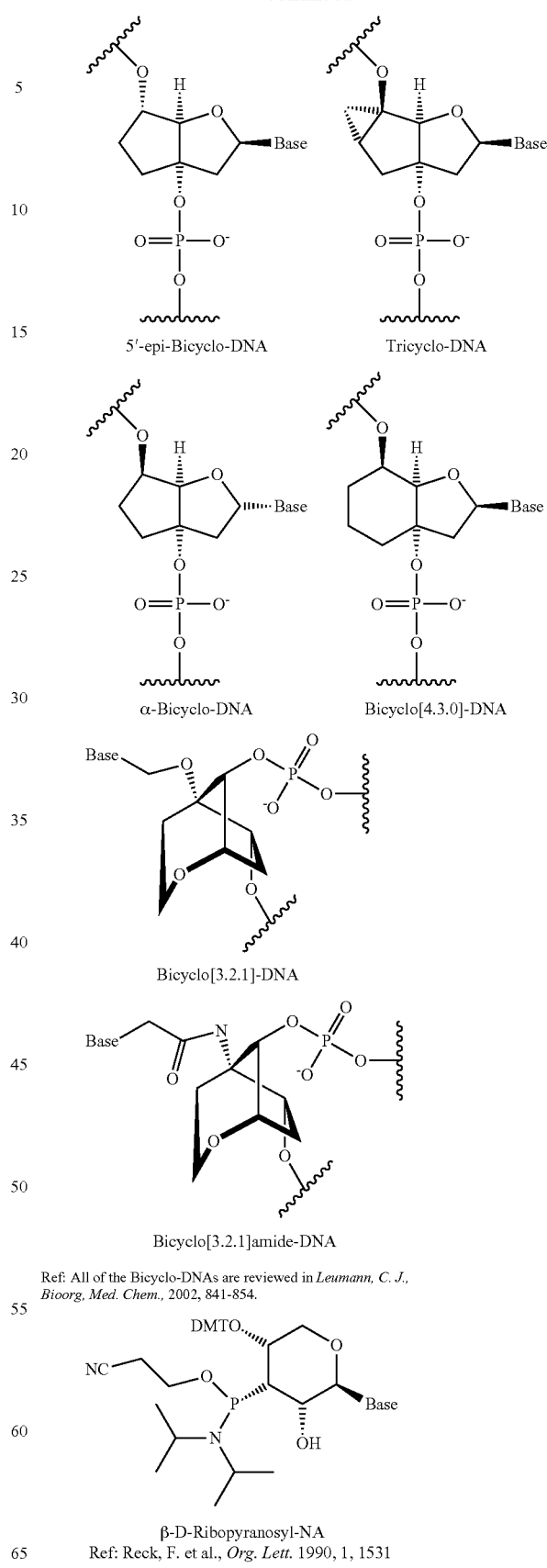
5′-epi-Bicyclo-DNA  Tricyclo-DNA
α-Bicyclo-DNA  Bicyclo[4.3.0]-DNA
Bicyclo[3.2.1]-DNA
Bicyclo-DNA
Bicyclo[3.2.1]amide-DNA
Ref: All of the Bicyclo-DNAs are reviewed in Leumann, C. J., Bioorg. Med. Chem., 2002, 841-854.
6′-Amino-Bicyclo-DNA
β-D-Ribopyranosyl-NA
Ref: Reck, F. et al., Org. Lett. 1990, 1, 1531

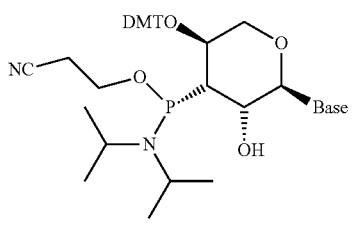
α-L-Lyxopyranosyl-NA
Ref: Reck, F. et al., *Org. Lett.* 1990, 1, 1531
General Structure of 2'-Modified Oligomers
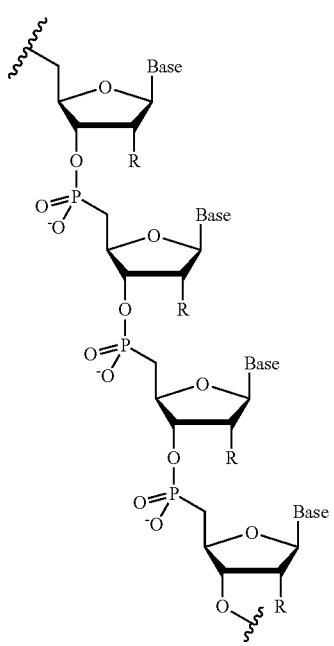
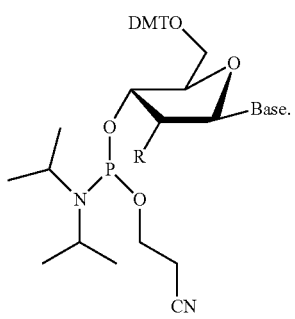
2'-R-RNA
Ref: Reviewed by Manoharan, M. Biochim. *BioPhys. Acta*, 1999, 117-130
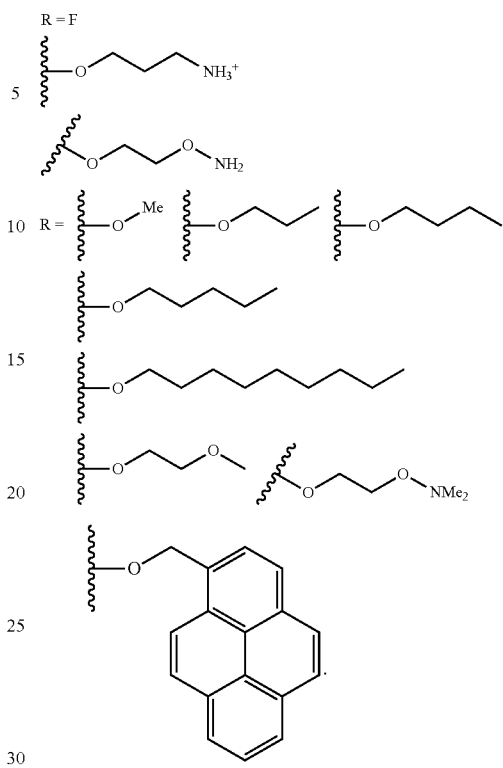
Ref: Yamana, K. et al.,
*Tetrahedron Lett.*,
1991, 6347-6350
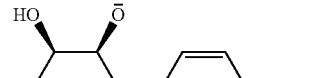
Ref: Sayer, J. et al.,
*J. Org. Chem.*,
1991, 56, 20-29
Examples of modifications that, to our knowledge, are not synthesised or published yet:
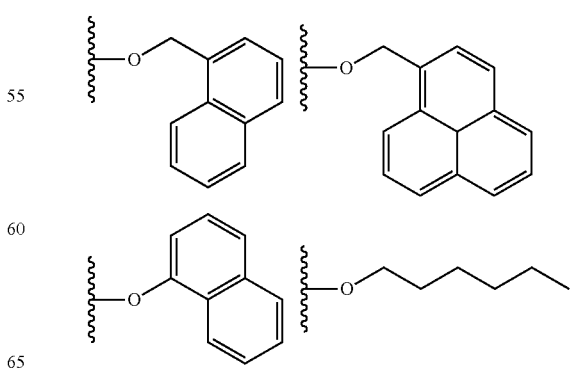

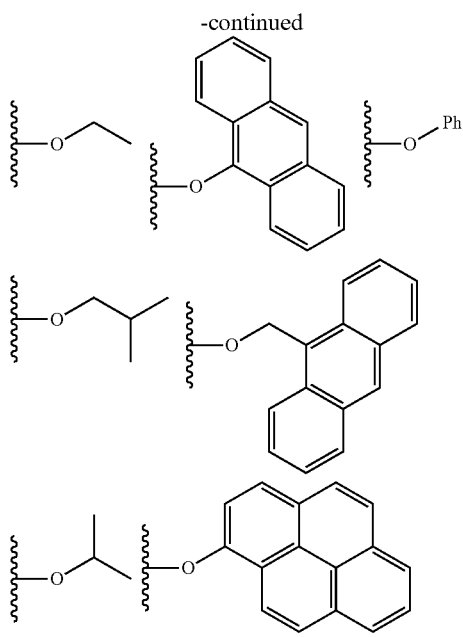

Some of the backbone monomer units shown above are already coupled to intercalators according to the present invention, while others can have intercalators linked to the nucleotides. The interacalators can be connected at any available atom, such as at an atom of the nucleobase, the backbone or the linker linking said nucleobase and backbone if present. The intercalators could also replace the nucleobases or be coupled to its own backbone monomer unit of any sort.

In a preferred embodiment, the backbone monomer unit does not comprise a nucleobase, such as a naturally occurring nucleobase. It is also preferred that the linker does not comprise a nucleobase, such as a naturally occurring nucleobase.

When the backbone monomer unit comprises a ribose group it is in one embodiment preferred that the intercalator is covalently linked to said ribose group via a linker. In this embodiment, the intercalators are thus preferably not covalently linked to a phosphate group of the backbone via a linker (Y).

The backbone monomer unit of LNA (locked nucleic acid) is a sterically restricted DNA backbone monomer unit, which comprises an intramolecular bridge that restricts the usual conformational freedom of a DNA backbone monomer unit, LNA may be any LNA molecule as described in WO 99/14226 (Exiqon), preferably, LNA is selected from the molecules depicted in the abstract of WO 99/14226. Preferred LNA according to the present invention comprises a methyl linker connecting the 2'-O position to the 4'-C position, however other LNA's such as LNA's wherein the 2' oxy atom is replaced by either nitrogen or sulphur are also comprised within the present invention.

The preferred backbone monomer units of nucleotides comprising intercalators according to the present invention are backbone monomer units that allow said intercalator to interact with its target nucleic acid.

In one preferred embodiment of the present invention, the backbone monomer unit is selected from the group consisting of acyclic backbone monomer units. Acyclic is meant to cover any backbone monomer unit, which does not comprise a ring structure, for example the backbone monomer unit preferably does not comprise a ribose or a deoxyribose group.

It is thus preferred, that the backbone monomer unit of an hydrophobic nucleotide according to the present invention may be selected from the group consisting of backbone monomer units comprising at least one chemical group selected from the group consisting of trivalent and pentavalent phosphorous atom such as a pentavalent phosphorous atom. More preferably, the phosphate atom of the backbone monomer unit according to the present invention may be selected from the group consisting of backbone monomer units comprising at least one chemical group selected from the group consisting of, phosphoester, phosphodiester, phosphoramidate and phosphoramidit groups.

In particular, it is preferred that the backbone monomer unit of a hydrophobic nucleotide according to the present invention is selected from the group consisting of acyclic backbone monomer units comprising at least one chemical group selected from the group consisting of phosphate, phosphoester, phosphodiester, phosphoramidate and phosphoramidit groups.

Preferably, the backbone monomer unit is capable of being incorporated into a phosphate backbone of a nucleic acid or nucleic acid analogue in a manner so that at the most 5, for example at the most 4 atoms are separating the phosphor atom of the backbone monomer unit and the nearest neighbouring phosphor atom, more preferably 5, such as at the most 4 atoms are separating the phosphor atom of the backbone monomer unit and the nearest neighbouring phosphor atom, in both cases not including the phosphor atoms themselves.

In a particularly preferred embodiment of the present invention, the hydrophobic nucleotide comprises a backbone monomer unit that comprises a phosphoramidit and more preferably the backbone monomer unit comprises a trivalent phosphoramidit or a pentavalent.

Suitable trivalent phosphoramidits are trivalent or pentavalent phosphoramidits that may be incorporated into the backbone of a nucleic acid and/or a nucleic acid analogue. Usually, the amidit group per se may not be incorporated into the backbone of a nucleic acid, but rather the amidit group or part of the amidit group may serve as a leaving group and/or protecting group. However, it is preferred that the backbone monomer unit comprises a phosphoramidit group, because such a group may facilitate the incorporation of the backbone monomer unit into a nucleic acid backbone.

In one embodiment of the present invention, the backbone monomer unit may be any of the backbone monomer units described in international patent application WO03/052132 in the section "Backbone monomer unit" on p. 24, l. 27-p. 43, l. 14.

Linker

The linker of an intercalator nucleotide according to the present invention is a moiety connecting the intercalator and the backbone monomer of said hydrophobic nucleotide, preferably covalently linking said intercalator and the backbone monomer unit. The linker may comprise one or more atom(s) or bond(s) between atoms.

By the definitions of backbone and intercalator defined herein above, the linker is the shortest path linking the backbone and the intercalators. If the intercalator is linked directly to the backbone, the linker is a bond.

The linker usually consists of a chain of atoms or a branched chain of atoms. Chains can be saturated as well as unsaturated. The linker may also be a ring structure with or without conjugated bonds.

For example the linker may comprise a chain of m atoms selected from the group consisting of C, O, S, N, P, Se, Si, Ge, Sn and Pb, preferably from the group consisting of C, O, S, N and P, even more preferably they are C, wherein one end of the chain is connected to the intercalator and the other end of the chain is connected to the backbone monomer unit, wherein m is an integer.

In some embodiments, the total length of the linker and the intercalators of the hydrophobic nucleotides according to the present invention preferably is between 8 and 13 Å (see herein below). Accordingly, m should be selected dependent on the size of the intercalators of the specific hydrophobic nucleotide.

I.e. m should be relatively large, when the intercalator is small and m should be relatively small when the intercalator is large. For most purposes however m will be an integer from 1 to 7, such as from 1-6, such as from 1-5, such as from 1-4. As described above the linker may be an unsaturated chain or another system involving conjugated bonds. For example, the linker may comprise cyclic conjugated structures. Preferably, m is from 1 to 4 when the linker is a saturated chain.

When the intercalator is pyrene, m is preferably an integer from 1 to 7, such as from 1-6, such as from 1-5, such as from 1-4, more preferably from 1 to 4, even more preferably from 1 to 3, most preferably m is 2 or 3.

When the intercalator has the structure

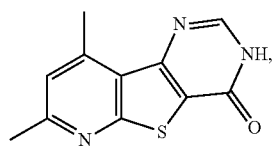

m is preferably from 2 to 6, more preferably 2.

In one embodiment, the linker is an azaalkyl, oxaalkyl, thiaalkyl or alkyl chain. For example the linker may be an alkyl chain substituted with one or more selected from the group consisting C, H, O, S, N, P, Se, Si, Ge, Sn and Pb, preferably selected from the group consisting of C, H, O, S, N and P. In a preferred embodiment the linker consists of an unbranched alkyl chain, wherein one end of the chain is connected to the intercalators and the other end of the chain is connected to the backbone monomer unit and wherein each C is substituted with 2H. More preferably, said unbranched alkyl chain is from 1 to 5 atoms long, such as from 1 to 4 atoms long, such as from 1 to 3 atoms long, such as from 2 to 3 atoms long.

In another embodiment, the linker consists of from 1-6 C atoms, from 0-3 of each of the following atoms O, S, N. More preferably the linker consists of from 1-6 C atoms and from 0-1 of each of the atoms O, S, N.

In a preferred embodiment, the linker consists of a chain of C, O, S and N atoms, optionally substituted. Preferably said chain should consist of at the most 3 atoms, thus comprising from 0 to 3 atoms selected individually from C, O, S, N, optionally substituted.

In a preferred embodiment, the linker consists of a chain of C, N, S and O atoms, wherein one end of the chain is connected to the intercalator and the other end of the chain is connected to the backbone monomer unit.

Preferably such a chain comprise one of the linkers shown below, most preferably the linker consist of one of the molecules shown below:

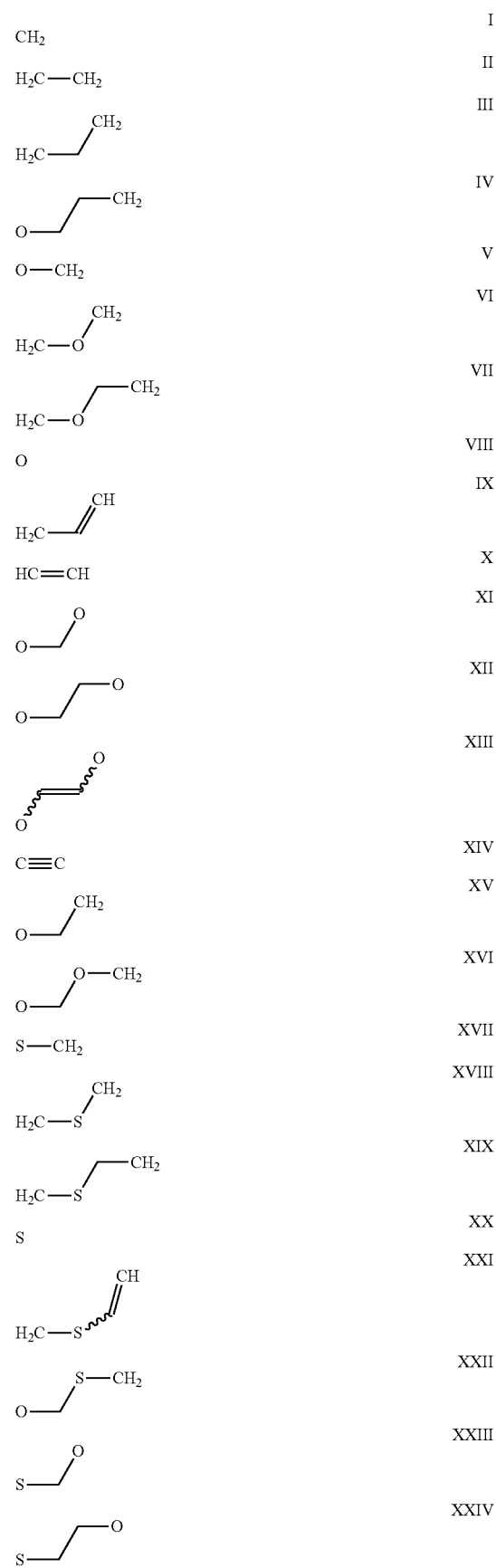

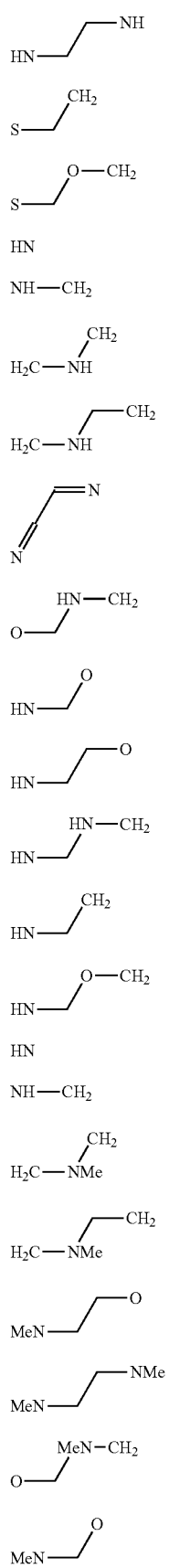
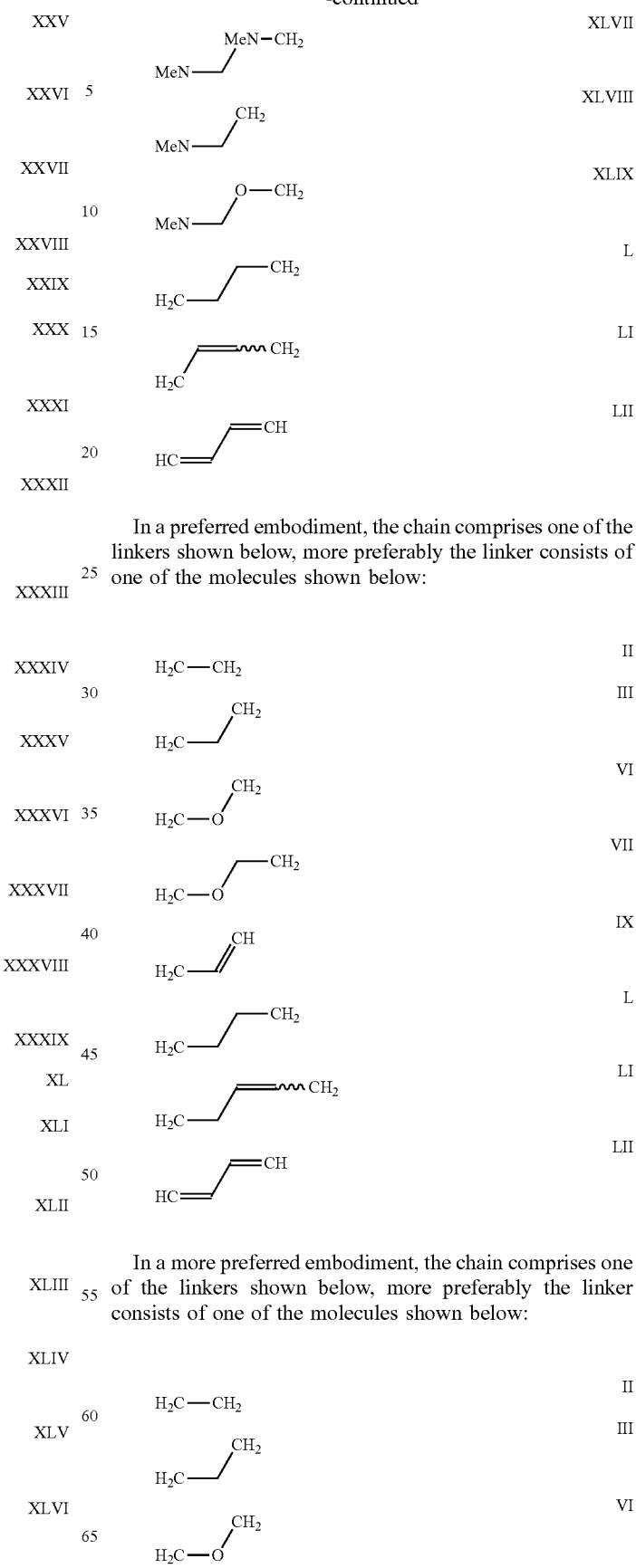
In a preferred embodiment, the chain comprises one of the linkers shown below, more preferably the linker consists of one of the molecules shown below:
In a more preferred embodiment, the chain comprises one of the linkers shown below, more preferably the linker consists of one of the molecules shown below:

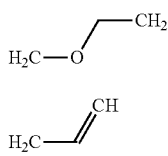

The linker constitutes Y in the formula for the hydrophobic nucleotide X—Y-Q, as defined above, and hence X and Q are not part of the linker.

In one embodiment of the invention the linker may be any of the linkers described in WO03/052132 in the section "Linker" on p. 54, l. 15 to p. 58, l. 7.

Sample

The present invention provides methods for detecting the presence of a variant sequence in a sample comprising nucleic acids.

The sample may comprise cells comprising said nucleic acids. The cells may for example be prokaryotic cells or eukaryotic cells, such as plant cells or mammalian cells.

The sample may for example be a synthetically prepared sample, which may or may not have been further processed in vitro, however most frequently, the sample is a sample obtained from an individual.

Thus, frequently, it is desirable to test the DNA or RNA of an individual, such as a mammal, for example a human being. In that case the sample is a sample derived from said individual. Thus, the sample may for example comprise nucleic acids selected from the group consisting of DNA, mRNA, miRNA or any other RNA sequence. The sample may be derived from a body fluid sample for example a blood sample, a biopsy, a sample of hair, nails or the like or any other suitable sample. In embodiments of the invention, wherein the individual is suffering from cancer, the sample may be a sample of a cancer tumour removed from the individual by surgery, or a biopsy of said tumour. However, in embodiments of the invention wherein the individual is suffering from cancer, the sample may also be a blood sample, which typically may contain CTCs and cfDNA.

The sample may be processed in vitro prior to detection of the presence of the variant sequence. For example the sample may be subjected to one or more purification steps that may purify nucleic acids from the sample completely or partially. Furthermore, the sample may have been subjected to reverse transcription.

The sample may comprise a complex biological mixture of nucleic acid (RNA and DNA) and non-nucleic acids, for example an intact cell or a crude cell extract.

If the target DNA is double stranded or otherwise have significant secondary and tertiary structure, it may need to be heated prior to performing the methods of the invention. It may also be desirable in some cases to extract the nucleic acids from the complex biological samples prior to performing the PCR by any methods known in the art.

The sample may comprise a wide range of eukaryotic and prokaryotic cells, including protoplasts; or other biological materials that may harbour target deoxyribonucleic acids. The methods are thus applicable to tissue culture animal cells, animal cells (e.g., blood, serum, plasma, reticulocytes, lymphocytes, urine, bone marrow tissue, cerebrospinal fluid or any product prepared from blood or lymph) or any type of tissue biopsy (e.g. a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a mammal biopsy, an uterus biopsy, a testicular biopsy, an eye biopsy or a brain biopsy, homogenized in lysis buffer), plant cells or other cells sensitive to osmotic shock and cells of bacteria, yeasts, viruses, mycoplasmas, protozoa, rickettsia, fungi and other small microbial cells and the like. The assay and isolation procedures of the present invention are useful, for instance, for detecting non-pathogenic or pathogenic micro organisms of interest. By detecting the presence of a variant sequence in a biological sample, the presence of the micro organisms may be established.

PCR Reagents

The methods of the invention in general comprise use of "PCR reagents". Also the kit-of-parts according to the invention may comprise PCR reagents.

Said PCR reagents may be any reagents, which are required for or may be beneficial for performing a PCR. The skilled person is well aware of how to perform a PCR and which reagents may be useful for performing a PCR. Useful methods and materials for PCR are for example described in Sambrook J et al. 2000. Molecular Cloning: A Laboratory Manual (Third Edition), Cold Spring Habor Laboratory Press.

In general the PCR reagents at least comprise a nucleic acid polymerase, and nucleotides.

Thus, the PCR reagents may comprise deoxynucleoside triphosphates (dNTPs), in particular all of the four naturally-occurring deoxynucleoside triphosphates (dNTPs).

The PCR reagents frequently comprise deoxyribonucleoside triphosphate molecules, including all of dATP, dCTP, dGTP, dTTP. In some cases dUTP is added.

The nucleic acid polymerase may be any useful polymerase. Said nucleic acid polymerase may be any nucleic acid polymerase, such as a DNA polymerase. The nucleic acid polymerase is in general thermostable, so that it can retain activity after having been subjected to high denaturing temperatures. Also the nucleic acid polymerase should have activity at the elongation temperature, which is typically chosen to be higher than the annealing temperature.

In some embodiments, the nucleic acid polymerase is a DNA polymerase with 5' to 3' exonuclease activity. This may in particular be the case in embodiments of the invention, wherein the detection probe is a hydrolysis probe (e.g. a Taqman probe). One advantage of the blocking oligonucleotides of the invention is that they are not broken down by 5' to 3' exonuclease activity to any significant extent, and thus can maintain blocking activity even if a DNA polymerase with 5' to 3' exonuclease activity is used.

Any DNA polymerase, e.g., a DNA polymerase with 5' to 3' exonuclease activity that catalyzes primer extension can be used. For example, a thermostable DNA polymerase can be used.

In one embodiment, the nucleic acid polymerase is a Taq polymerase.

The PCR reagents may also comprise compounds useful in assisting the activity of the nucleic acid polymerase. Thus, the PCR reagent may comprise a divalent cation, e.g., magnesium ions. Said magnesium ions may be added on the form of e.g. magnesium chloride or magnesium acetate ($MgCl_2$) or magnesium sulfate is used.

The PCR reagents may also comprise one or more of the following:
- non-specific blocking agents such as BSA or gelatin from bovine skin, betalactoglobulin, casein, dry milk, or other common blocking agents,
- non-specific background/blocking nucleic acids (e.g., salmon sperm DNA), biopreservatives (e.g. sodium azide),
PCR enhancers (e.g. Betaine, Trehalose, etc.),
inhibitors (e.g. RNAse inhibitors).

The PCR reagents may also contain other additives, e.g., dimethyl sulfoxide (DMSO), glycerol, betaine (mono)hydrate (N,N,N-trimethylglycine=[caroxy-methyl]trimethylammonium), trehalose, 7-Deaza-2'-deoxyguanosine triphosphate (dC7GTP or 7-deaza-2'-dGTP), formamide (methanamide), tettrmethylammonium chloride (TMAC), other tetraalkylammonium derivaties (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q.

The PCR reagents may comprise a buffering agent.

In some cases, a non-ionic Ethylene Oxide/Propylene Oxide block copolymer is added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. Pluronic F-68 can be present at a concentration of about 0.5% w/v.

In some cases, magnesium sulfate can be substituted for magnesium chloride, at similar concentrations. A wide range of common, commercial PCR buffers from varied vendors can be substituted for the buffered solution.

PCR usually comprises incubating the blocking oligonucleotide, the set of primers and the PCR reagents in cycles comprising incubation at different temperatures. Typically, each cycle comprises incubation at a denaturing temperature, an annealing temperature and an elongation temperature. The PCR may also comprise additional steps, e.g. a first step of incubation at a denaturation temperature for a long period of time and/or a last step of incubation at an elongation temperature for a long period of time. The skilled person is well aware of how to choose suitable denaturation temperatures, elongation temperatures and annealing temperatures, times and number of cycles. Typically the denaturation temperature is in the range of 90 to 100° C., the elongation temperature is in the range of 55 to 80° C. and the annealing temperature is close to the melting temperatures of the primers, e.g. in the range of 40 to 70° C. The time for incubation at each temperature is typically relatively short, e.g. in the range of 30 to 120 seconds. The number of cycles may for example be in the range of 15 to 60, for example in the range of 30 to 40. A typical PCR reaction can also be comprised of just two steps with a denaturation temperature typically in the range of 90 to 100° C. followed by an annealing/elongation temperature typically in the range of 55 to 80° C. Information on how to select parameters for PCR are readily available for example in Sambrook J et al. 2000. Molecular Cloning: A Laboratory Manual (Third Edition), Cold Spring Habor Laboratory Press.

Predicting Efficacy of Treatment of a Clinical Condition

It is an aspect of the invention to provide methods of predicting the efficacy of treatment of a clinical condition in an individual in need thereof with a predetermined drug, wherein the efficacy of treatment of said clinical condition with said drug is associated with the presence of a variant sequence.

Thus, some mutations may be indicative of whether or not a certain drug may be efficient for treatment of an individual. In particular, specific mutations may be indicative of a specific response to a predetermined drug treatment. For example, the mutation may be indicative of whether an individual will respond positively to said drug treatment, whether the disease of an individual is resistant toward the given drug or whether an individual cannot tolerate a specific drug treatment.

Methods for predicting the efficacy of treatment of a clinical condition in an individual may comprise the steps of a. providing a sample from said individual b. performing the method for detecting the presence of a variant sequence according to the invention to determine whether the sample comprises the variant sequence wherein the presence of said variant sequence is indicative of whether said drug is efficient in treating said clinical condition in said individual.

The clinical condition may for example be cancer. Many mutations have been identified, which are indicative of whether a given cancer drug or combination of drugs is effective in treating a particular cancer.

In one embodiment of the invention, the variant sequence is an activating mutation in KRAS or NRAS. Several activating mutations in KRAS and NRAS have been identified. Typically, individual suffering from cancer characterized by an activating mutation in KRAS or NRAS will not benefit from treatment targeting EGFR. Thus, in one embodiment the invention relates to a method of predicting the efficacy of a treatment targeting EGFR in an individual suffering from cancer, the method comprising the steps of a) providing a sample of said cancer from said individual b) detecting the presence or absence of an activating mutation in KRAS and/or NRAS in said sample using the methods for detecting a variant sequence according to the invention, wherein the presence of an activating mutation is indicative of that the individual will not benefit from treatments targeting EGFR.

The wild type amino acid sequences of human BRAF, EGFR, KRAS, NRAS and PIK3CA are provided herein as SEQ ID NO:1, SEQ ID NO:2, SEQ ID NO:3, SEQ ID NO:4 and SEQ ID NO:5, respectively. Said activating mutation may for example be selected from mutations in positions 12, 13, 59, 61, 117 and 146 of KRAS and mutations in positions 12, 13, 59, 61, 117, 148 of NRAS. For example the mutation may be selected from the group of mutations shown in Table 1. In particular, said mutation may be mutations in KRAS exon 2, codons 12 and/or 13.

TABLE 1

Non-limiting examples of mutations indicative of efficacy of treatment investigated by methods of the present invention.

| Gene | Mutations | | |
|---|---|---|---|
| BRAF | Val600Asp | | |
| | Val600Glu | | |
| | Val600Lys | | |
| | Val600Arg | | |
| EGFR | Glu709Ala | Gly719Ala | Exon19 Deletions |
| | Glu709Gly | Gly719Cys | Exon19 Insertions |
| | Glu709Lys | Gly719Asp | Ser768Ile |
| | | Gly719Ser | Thr790Met |
| | | | Leu858Arg |
| | | | Leu861Gln |
| KRAS | Gly12Ala | Gln61His$^{A>C}$ | Lys117Asn$^{A>C}$ |
| | Gly12Asp | Gln61His$^{A>T}$ | Lys117Asn$^{A>T}$ |
| | Gly12Arg | Gln61Glu | Ala146Pro |

TABLE 1-continued

Non-limiting examples of mutations indicative of efficacy of treatment investigated by methods of the present invention.

| Gene | Mutations | | | |
|------|-----------|---|---|---|
|  | Gly12Cys | Gln61Lys | Ala146Thr |  |
|  | Gly12Ser | Gln61Leu | Ala146Val |  |
|  | Gly12Val | Gln61Arg |  |  |
|  | Gly13Asp | Ala61Gly |  |  |
|  |  | Ala61Thr |  |  |
| NRAS | Gly12Ala | Gly12Ala | Gln61His$^{A>T}$ | Lys117Asn$^{G>C}$ |
|  | Gly12Cys | Gly13Cys | Gln61His$^{A>C}$ | Lys117Asn$^{G>T}$ |
|  | Gly12Asp | Gly13Asp | Gln61Lys | Ala146Pro |
|  | Gly12Arg | Gly13Arg | Gln61Leu | Ala146Thr |
|  | Gly12Ser | Gly13Ser | Gln61Arg | Ala146Val |
|  | Gly12Val | Gly13Val |  |  |
| PIK3CA | His1047Leu |  |  |  |
|  | His1047Arg |  |  |  |
|  | His1047Tyr |  |  |  |

Said treatment targeting EGFR may be any treatment aimed at reducing or even abolishing the activity of EGFR. Several such treatments are known in the art including treatment with antibodies to EGFR. Examples of antibodies to EGFR useful for treatment of cancer patients include Cetuximab or Panitumumab. Treatments targeting EGFR may also be combination treatments, for example involving a combination of treatment with antibodies to EGFR and chemotherapy, e.g. FOLFOX4 or FOLFIRI schemes.

Another example of a mutation indicative of efficacy of treatment is mutations in EGFR. Thus, specific mutations in EGFR are indicative of efficacy of treatment targeting EGFR and/or BRAF. Thus, in one embodiment the invention relates to a method of predicting the efficacy of a treatment targeting EGFR and/or BRAF in an individual suffering from cancer, the method comprising the steps of
 a) providing a sample of said cancer from said individual
 b) detecting the presence or absence of a mutation in EGFR in said sample using the methods for detecting a variant sequence according to the invention,
wherein the presence of a mutation is indicative of that the individual will not benefit from treatment targeting EGFR or BRAF.

Said EGFR mutation may for example be located in exon 20, and may in particular be the T790M mutation.

Predicting the Presence of a Clinical Condition

The methods of the invention are also useful for predicting or even diagnosing the presence of any clinical condition associated with a particular mutation in an individual.

Such methods may comprise the steps of
 a) Providing a sample from said individual
 b) detecting the presence of a mutation associated with the clinical condition in the sample by performing the methods for detecting a variant sequence according to the invention;
  wherein the presence of said variant sequence is indicative of said individual suffering from said clinical condition.

Numerous clinical conditions are known to be associated with particular mutations, and blocking oligonucleotides and sets of primers for detecting any such mutation may be designed.

In one embodiment, the clinical condition is cancer.

Multiplex

It is often advantageous to investigate a sample for the presence of several different variant sequences. Accordingly, the methods of the invention may be adapted, so that several variant sequences are detected simultaneously. Often it is sufficient just to determine if at least one of many variant sequences is present. For example, when determining the presence of an activating mutation in KRAS or NRAS, it may be sufficient to detect whether at least one activating mutation is present, and of less relevance to determine exactly which one. In such cases the methods of the invention may be for detecting the presence of at least one of a number of variant sequences in the same method.

It is also possible to include one or more controls in the PCR reactions of the invention. A control could for example be detection of the presence of one or more housekeeping genes. If the control is added to the same reaction container in the PCR it is ensured that (at least most of) the conditions of the control and the assay are the same, and therefore this is often advantageous over running parallel experiments.

When more than one experiment is included in an assay, it is said to be a multiplexing assay or a multiplex assay. When only one experiment is included in an assay, this may also be referred to as a simplex assay.

It is therefore an embodiment of the invention to provide one blocking oligonucleotide, one primer 2 and at least two different primer 1s, wherein each of the primer 1s comprise a sequence of at least 15 nucleotides, which is identical to the target nucleic acid sequence comprising the different variant sequences expect for up to one mismatch. When performing a PCR in the presence of the blocking oligonucleotide, primer 2 and the different primer 1s generation of a PCR product is indicative of the presence of at least one of the different variant sequences recognised by the different primer 1s. This kind of multiplexing is only useful if the different variant sequences are positioned sufficiently close to each other to allow design of the different primer 1s all having the required overlap with the blocking oligonucleotides. For example, such a multiplexing method may be useful for detecting different mutations at the same position in a gene, or for detecting different mutations in the same and/or neighbouring positions in a gene.

It is also an embodiment of the invention to provide two different blocking oligonucleotides and two different sets of primers useful for detecting two different variant sequences. Such methods may include running one PCR reaction in the presence of both blocking oligonucleotides and both sets of primers. It may be preferable in such embodiments that the sets of primers are designed to have similar melting temperatures. If several different sequences are known to be occurring at a specific NOI, then even more than two different blocking oligonucleotides may be used each blocking different reference NOI sequences.

Detection of a PCR product in a multiplex reaction may be performed by any useful method, e.g. by use of detection probe. It is possible to use only one detection probe capable of detecting the different PCR products. This may in particular be the case, when there is an overlap between the different target nucleic acid sequences. However, individual detection probes for the different target nucleic acid sequences may also be used. If different detection probes are used, they may be labelled in a similar manner, in which case the assay is useful for determined whether at least one of the variant sequences is present. The detection probes may also be differentially labelled, allowing for detection of different variant sequences in one reaction.

| Sequence listing | |
|---|---|
| SEQ ID NO: 1 | Amino acid sequence of BRAF |
| SEQ ID NO: 2 | Amino acid sequence of EGFR |
| SEQ ID NO: 3 | Amino acid sequence of KRAS |
| SEQ ID NO: 4 | Amino acid sequence of NRAS |
| SEQ ID NO: 5 | Amino acid sequence of PIK3CA |
| SEQ ID NO: 6 | NRAS A59D primer 1 sequence (FIG. 4) |
| SEQ ID NO: 7 | NRAS 59 primer 2 sequence (FIG. 4) |
| SEQ ID NO: 8 | NRAS 59 probe sequence (FIG. 4) |
| SEQ ID NO: 9 | NRAS 59 blocking oligonucleotide sequence (FIG. 4) |
| SEQ ID NO: 10 | KRAS 59/61 primer 2 sequence (FIG. 7) |
| SEQ ID NO: 11 | KRAS Q61K primer 1 sequence (FIG. 7) |
| SEQ ID NO: 12 | KRAS Q61L primer 1 sequence (FIG. 7) |
| SEQ ID NO: 13 | KRAS A59G primer 1 sequence (FIG. 7) |
| SEQ ID NO: 14 | KRAS 61 probe sequence (FIG. 7) |
| SEQ ID NO: 15 | KRAS 59/61 blocking oligonucleotide sequence (FIG. 7) |
| SEQ ID NO: 16 | Primer 1 sequence, assay 1 (FIG. 3B) |
| SEQ ID NO: 17 | Blocking oligonucleotide sequence, assay 1 (FIG. 3B) |
| SEQ ID NO: 18 | Primer 1 sequence, assay 2 (FIG. 3B) |
| SEQ ID NO: 19 | Blocking oligonucleotide sequence, assay 2 (FIG. 3B) |
| SEQ ID NO: 20 | Primer 1 sequence, assay 3 (FIG. 3B) |
| SEQ ID NO: 21 | Blocking oligonucleotide sequence, assay 3 (FIG. 3B) |
| SEQ ID NO: 22 | Primer 1 sequence, assay 4 (FIG. 3B) |
| SEQ ID NO: 23 | Blocking oligonucleotide sequence, assay 4 (FIG. 3B) |
| SEQ ID NO: 24 | Primer 1 sequence, assay 5 (FIG. 3B) |
| SEQ ID NO: 25 | Blocking oligonucleotide sequence, assay 5 (FIG. 3B) |
| SEQ ID NO: 26 | Primer 1 sequence, assay 6 (FIG. 3B) |
| SEQ ID NO: 27 | Blocking oligonucleotide sequence, assay 6 (FIG. 3B) |
| SEQ ID NO: 28 | Primer 2 sequence, assay 1 (FIG. 3B) |
| SEQ ID NO: 29 | Primer 2 sequence, assay 2 (FIG. 3B) |
| SEQ ID NO: 30 | Primer 2 sequence, assays 3, 4, 5 (FIG. 3B) |
| SEQ ID NO: 31 | Primer 2 sequence, assay 6 (FIG. 3B) |

SEQ ID NO: 1
MAALSGGGGGGAEPGQALFNGDMEPEAGAGAGAAASSAADPAIPEEVWNIKQMIKL
TQEHIEALLDKFGGEHNPPSIYLEAYEEYTSKLDALQQREQQLLESLGNGTDFSVSSS
ASMDTVTSSSSSSLSVLPSSLSVFQNPTDVARSNPKSPQKPIVRVFLPNKQRTVVPAR
CGVTVRDSLKKALMMRGLIPECCAVYRIQDGEKKPIGWDTDISWLTGEELHVEVLENV
PLTTHNFVRKTFFTLAFCDFCRKLLFQGFRCQTCGYKFFIQRCSTEVPLMCVNYDQLD
LLFVSKFFEHHPIPQEEASLAETALTSGSSPSAPASDSIGPQILTSPSPSKSIPIPQPFRP
ADEDHRNQFGQRDRSSSAPNVHINTIEPVNIDDLIRDQGFRGDGGSTTGLSATPPASL
PGSLTNVKALQKSPGPQRERKSSSSSEDRNRMKTLGRRDSSDDWEIPDGQITVGQRI
GSGSFGTVYKGKWHGDVAVKMLNVTAPTPQQLQAFKNEVGVLRKTRHVNILLFMGY
STKPQLAIVTQWCEGSSLYHHLHIIETKFEMIKLIDIARQTAQGMDYLHAKSIIHRDLKSN
NIFLHEDLTVKIGDFGLATVKSRWSGSFIQFEQLSGSILWMAPEVIRMQDKNPYSFQSD
VYAFGIVLYELMTGQLPYSNINNRDQIIFMVGRGYLSPDLSKVRSNCPKAMKRLMAEC
LKKKRDERPLFPQILASIELLARSLPKIHRSASEPSLNRAGFQTEDFSLYACASPKTPIQ
AGGYGAFPVH

-continued

Sequence listing

SEQ ID NO: 2
MRPSGTAGAALLALLAALCPASRALEEKKVCQGTSNKLTQLGTFEDHFLSLQRMFNN
CEVVLGNLEITYVQRNYDLSFLKTIQEVAGYVLIALNTVERIPLENLQIIRGNMYYENSY
ALAVLSNYDANKTGLKELPMRNLQEILHGAVRFSNNPALCNVESIQWRDIVSSDFLSN
MSMDFQNHLGSCQKCDPSCPNGSCWGAGEENCQKLTKIICAQQCSGRCRGKSPSD
CCHNQCAAGCTGPRESDCLVCRKFRDEATCKDTCPPLMLYNPTTYQMDVNPEGKYS
FGATCVKKCPRNYVVTDHGSCVRACGADSYEMEEDGVRKCKKCEGPCRKVCNGIGI
GEFKDSLSINATNIKHFKNCTSISGDLHILPVAFRGDSFTHTPPLDPQELDILKTVKEITG
FLLIQAWPENRTDLHAFENLEHRGRTKQHGQFSLAVVSLNITSLGLRSLKEISDGDVIIS
GNKNLCYANTINWKKLFGTSGQKTKIISNRGENSCKATGQVCHALCSPEGCWGPEPR
DCVSCRNVSRGRECVDKCNLLEGEPREFVENSECIQCHPECLPQAMNITCTGRGPD
NCIQCAHYIDGPHCVKTCPAGVMGENNTLVWKYADAGHVCHLCHPNCTYGCTGPGL
EGCPTNGPKIPSIATGMVGALLLLLVVALGIGLFMRRRHIVRKRTLRRLLQERELVEPLT
PSGEAPNQALLRILKETEFKKIKVLGSGAFGTVYKGLWIPEGEKVKIPVAIKELREATSP
KANKEILDEAYVMASVDNPHVCRLLGICLTSTVQLITQLMPFGCLLDYVREHKDNIGSQ
YLLNWCVQIAKGMNYLEDRRLVHRDLAARNVLVKTPQHVKITDFGLAKLLGAEEKEYH
AEGGKVPIKWMALESILHRIYTHQSDVWSYGVTVWELMTEGSKPYDGPASEISSILEK
GERLPQPPICTIDVYMIMVKCWMIDADSRPKFRELIIEFSKMARDPQRYLVIQGDERMH
LPSPTDSNFYRALMDEEDMDDVVDADEYLIPQQGFFSSPSTSRTPLLSSLSATSNNST
VACIDRNGLQSCPIKEDSFLQRYSSDPTGALTEDSIDDTFLPVPEYINQSVPKRPAGSV
QNPVYHNQPLNPAPSRDPHYQDPHSTAVGNPEYLNTVQPTCVNSTFDSPAHWAQK
GSHQISLDNPDYQQDFFPKEAKPNGIFKGSTAENAEYLRVAPQSSEFIGA

SEQ ID NO: 3
MTEYKLVVVGAGGVGKSALTIQLIQNHFVDEYDPTIEDSYRKQVVIDGETCLLDILDTA
GQEEYSAMRDQYMRTGEGFLCVFAINNSKSFADINLYREQIKRVKDSDDVPMVLVGN
KCDLPTRTVDTKQAHELAKSYGIPHETSAKTRQGVEDAFYTLVREIRQYRMKKLNSS
DDGTQGCMGLPCVVM

SEQ ID NO: 4
MTEYKLVVVGAGGVGKSALTIQLIQNHFVDEYDPTIEDSYRKQVVIDGETCLLDILDTA
GQEEYSAMRDQYMRTGEGFLCVFAINNTKSFEDIHHYREQIKRVKDSEDVPMVLVGN
KCDLPSRTVDTKQAQDLARSYGIPFIETSAKTRQRVEDAFYTLVREIRQYRLKKISKEE
KTPGCVKIKKCIIM

SEQ ID NO: 5
MPPRPSSGELWGIHLMPPRILVECLLPNGMIVTLECLREATLITIKHELFKEARKYPLHQ
LLQDESSYIFVSVTQEAEREEFFDETRRLCDLRLFQPFLKVIEPVGNREEKILNREIGFA
IGMPVCEFDMVKDPEVQDFRRNILNVCKEAVDLRDLNSPHSRAMYVYPPNVESSPEL
PKHIYNKLDKGQIIVVIWVIVSPNNDKQKYTLKINHDCVPEQVIAEAIRKKTRSMLLSSE
QLKLCVLEYQGKYILKVCGCDEYFLEKYPLSQYKYIRSCIMLGRMPNLMLMAKESLYS
QLPMDCFTMPSYSRRISTATPYMNGETSTKSLWVINSALRIKILCATYVNVNIRDIDKIY
VRTGIYHGGEPLCDNVNTQRVPCSNPRWNEWLNYDIYIPDLPRAARLCLSICSVKGRK
GAKEEHCPLAWGNINLFDYTDTLVSGKMALNLWPVPHGLEDLLNPIGVTGSNPNKET
PCLELEFDWFSSVVKFPDMSVIEEHANWSVSREAGFSYSHAGLSNRLARDNELREND
KEQLKAISTRDPLSEITEQEKDFLWSHRHYCVTIPEILPKLLLSVKWNSRDEVAQMYCL
VKDWPPIKPEQAMELLDCNYPDPMVRGFAVRCLEKYLTDDKLSQYLIQLVQVLKYEQ
YLDNLLVRFLLKKALTNQRIGHFFFWHLKSEMHNKTVSQRFGLLLESYCRACGMYLKH
LNRQVEAMEKLINLTDILKQEKKDETQKVQMKFLVEQMRRPDFMDALQGFLSPLNPA
HQLGNLRLEECRIMSSAKRPLWLNWENPDIMSELLFQNNEIIFKNGDDLRQDMLTLQII
RIMENIWQNQGLDLRMLPYGCLSIGDCVGLIEVVRNSHTIMQIQCKGGLKGALQFNSH
TLHQWLKDKNKGEIYDAAIDLFTRSCAGYCVATFILGIGDRHNSNIMVKDDGQLFHIDF
GHFLDHKKKKFGYKRERVPFVLTQDFLIVISKGAQECTKTREFERFQEMCYKAYLAIR
QHANLEINLFSMMLGSGMPELQSFDDIAYIRKTLALDKTEQEALEYFMKQMNDAHHG
GWTTKMDWIFHTIKQHALN items The invention may further be defined by the following items:
1. A method for detecting the presence of a variant sequence in a target nucleic acid sequence comprising nucleotide(s) of interest (NOI), wherein said NOI may consist of said variant sequence, of other variant sequences or of a reference NOI sequence, said method comprising the steps of
a) Providing a sample comprising nucleic acids
b) Providing a blocking oligonucleotide comprising a sequence of in the range of 10 to 50 nucleotides (referred to as "blocking sequence") into which in the range of 2 to 10 hydrophobic nucleotides have been inserted wherein
at least one hydrophobic nucleotide is positioned at the 5' end of said sequence or within 4 nucleotides from the 5' end; and
at least one hydrophobic nucleotide is positioned at the 3' end of said sequence or within 4 nucleotides from the 3' end; and
wherein the hydrophobic nucleotide has the structure

X—Y-Q wherein
X is a nucleotide or nucleotide analogue or a backbone monomer unit capable of being incorporated into the backbone of a nucleic acid or nucleic acid analogue, Q is a intercalator which is not taking part in Watson-Crick hydrogen bonding; and Y is a linker moiety linking said nucleotide or nucleotide analogue or backbone monomer unit and said intercalator; and wherein the blocking sequence is identical to a consecutive stretch of the target nucleic acid sequence comprising the reference NOI sequence, c) Providing a set of primers consisting of primer 1 and primer 2, wherein the set of primers together are capable of amplification of the target nucleic acid sequence comprising the variant sequence, and wherein primer 1 comprises a sequence of at least 15 nucleotides positioned at the 3' end of said primer, which is identical to a consecutive stretch of the target nucleic acid sequence comprising the variant sequence expect for up to one mismatch;

d) performing a polymerase chain reaction in the presence of said sample, said blocking oligonucleotide; said set of primers and PCR reagents;

e) detecting a product of said polymerase chain reaction, wherein the presence of a product of said polymerase chain reaction indicates the presence of a target nucleic acid sequence comprising the variant sequence in said sample.

2. The method according to item 1, wherein the step of detecting said product involves use of a detection probe.

3. The method according to any one of the preceding items, wherein the sample is a blood sample.

4. A kit-of-parts comprising a) a blocking oligonucleotide consisting of a sequence of in the range of 10 to 50 nucleotides (referred to as "blocking sequence") into which in the range of 2 to 10 hydrophobic nucleotides have been inserted, wherein at least one hydrophobic nucleotide is positioned at the 5' end of said sequence or within 4 nucleotides from the 5' end; and at least one hydrophobic nucleotide is positioned at the 3' end of said sequence or within 4 nucleotides from the 3' end; and Z is a hydrophobic nucleotide of the structure

X—Y-Q wherein

X is a backbone monomer unit capable of being incorporated into the backbone of a nucleic acid or nucleic acid analogue, Q is an intercalator, which is not taking part in Watson-Crick hydrogen bonding; and Y is a linker moiety linking said nucleotide or nucleotide analogue or backbone monomer unit and said intercalator; and wherein the blocking sequence is identical to a consecutive stretch of a target nucleic acid sequence comprising a reference NOI sequence; and b) a set of primers consisting of primer 1 and primer 2, wherein the set of primers together are capable of amplification of the target nucleic acid sequence comprising a variant sequence, and wherein primer 1 contains a sequence of at least 15 nucleotides positioned at the 3' end of said primer, which is identical to a consecutive stretch of the target nucleic acid sequence comprising the variant sequence expect for up to one mismatch.

5. The kit according to item 4, wherein the kit furthermore comprises a detection probe.

6. The kit according to any one of items 4 to 5, wherein the kit comprises at the most one kind of blocking oligonucleotide, one kind of primer 1 and one kind of primer 2.

7. The kit according to any one of items 4 to 5, wherein the kit comprises at least two different blocking oligonucleotides wherein at least one blocking oligonucleotide contains a blocking sequence identical to a consecutive stretch of a target nucleic acid sequence comprising a reference NOI sequence, and one or more blocking oligonucleotide(s) contain blocking sequence(s) identical to a consecutive stretch of a target nucleic acid sequence comprising other variant sequence(s), wherein said other variant sequences are different to the variant sequence identical to a stretch of primer 1.

8. The kit according to any one of items 4 to 5, wherein the kit comprises sets of primers comprising at least two different primer 1s and a primer 2, wherein a first primer 1 together with a primer 2 is capable of amplification of a target nucleic acid sequence comprising a first variant sequence, wherein said first primer 1 comprises a sequence of at least 15 nucleotides positioned at the 3' end of said primer, which is identical to a consecutive stretch of the target nucleic acid sequence comprising said first variant sequence expect for up to one mismatch, and a second primer 1 together with a primer 2 is capable of amplification of a target nucleic acid sequence comprising a second variant sequence, wherein said second primer 1 comprises a sequence of at least 15 nucleotides positioned at the 3' end of said primer, which is identical to a consecutive stretch of the target nucleic acid sequence comprising said second variant sequence expect for up to one mismatch; and wherein the sets of primers optionally comprise one or more further primer 1, which together with a primer 2 are capable of amplification of a target nucleic acid sequence comprising one or more further variant sequence(s), wherein said further primer 1(s) comprise a sequence of at least 15 nucleotides positioned at the 3' end of said primer, which is identical to a consecutive stretch of the target nucleic acid sequence comprising said further variant sequence(s) expect for up to one mismatch.

9. The kit according to any one of items 4 to 8, wherein the kit comprises at the most one kind of primer 2.

10. The method according to any one of items 1 to 3, wherein the method comprises use of a kit according to item 7.

11. The method according to item 10, wherein the method comprises the steps of a) Providing a sample comprising nucleic acids b) Providing at least two different blocking oligonucleotides as defined in item 1, wherein at least one blocking oligonucleotide contains a blocking sequence identical to a consecutive stretch of the target nucleic acid sequence comprising the reference NOI sequence, and one or more blocking oligonucleotide(s) contain blocking sequence(s) identical to a consecutive stretch of the target nucleic acid sequence comprising said other variant sequence(s), c) Providing a set of primers consisting of primer 1 and primer 2, wherein the set of primers together are capable of amplification of the target nucleic acid sequence comprising the variant sequence, and wherein primer 1 comprises a sequence of at least 15 nucleotides positioned at the 3' end of said primer, which is identical to a consecutive stretch of the target nucleic acid sequence comprising the variant sequence expect for up to one mismatch;

d) performing a polymerase chain reaction in the presence of said sample, said blocking oligonucleotides; said set of primers and PCR reagents;

e) detecting a product of said polymerase chain reaction, wherein the presence of a product of said polymerase chain reaction indicates the presence of a target nucleic acid sequence comprising the variant sequence in said sample.

12. The method according to any one of items 1 to 3, wherein the method comprises use of a kit according to any one of items 8 to 9.

13. The method according to item 12, wherein the method comprises the steps of
    a) Providing a sample comprising nucleic acids
    b) Providing a blocking oligonucleotide as defined herein, wherein said blocking oligonucleotide contains a blocking sequence identical to a consecutive stretch of the target nucleic acid sequence comprising the reference NOI sequence,
    c) Providing sets of primers comprising at least two different primer 1s and a primer 2, wherein a first primer 1 together with a primer 2 is capable of amplification of the target nucleic acid sequence comprising a first variant sequence, wherein said first primer 1 comprises a sequence of at least 15 nucleotides positioned at the 3' end of said primer, which is identical to a consecutive stretch of the target nucleic acid sequence comprising said first variant sequence expect for up to one mismatch, and a second primer 1 together with a primer 2 is capable of amplification of the target nucleic acid sequence comprising a second variant sequence, wherein said second primer 1 comprises a sequence of at least 15 nucleotides positioned at the 3' end of said primer, which is identical to a consecutive stretch of the target nucleic acid sequence comprising said second variant sequence expect for up to one mismatch; and optionally one or more further primer 1 together with a primer 2 are capable of amplification of the target nucleic acid sequence comprising one or more further variant sequence(s), wherein said further primer 1(s) comprise a sequence of at least 15 nucleotides positioned at the 3' end of said primer, which is identical to a consecutive stretch of the target nucleic acid sequence comprising said further variant sequence(s) expect for up to one mismatch;
    d) performing a polymerase chain reaction in the presence of said sample, said blocking oligonucleotide; said sets of primers and PCR reagents;
    e) detecting a product of said polymerase chain reaction, wherein the presence of a product of said polymerase chain reaction indicates the presence of a target nucleic acid sequence comprising the variant sequence in said sample.

14. The method or the kit according to any one of the preceding items, wherein a primer 1 comprises a sequence which is identical to a consecutive sequence of the blocking sequence of at least 3, preferably of at least 6 nucleotides except for up to one mismatch.

15. The method according to item 14, wherein the sequence of primer 1, which is identical to a consecutive sequence of the blocking sequence is positioned immediately 5' to the sequence identical to the variant sequence.

16. The method or the kit according to any one of the preceding items, wherein the most 3' nucleotide(s) of a primer 1 are identical to the variant sequence.

17. The method or the kit according to any one of the preceding items, wherein the variant sequence is a single nucleotide variant.

18. The method or the kit according to item 17, wherein the most 3' nucleotide of primer 1 is identical to the single nucleotide variant.

19. The method or the kit according to any one of items 1 to 16, wherein the variant sequence consists of more than one consecutive variant nucleotides.

20. The method or the kit according to item 11, wherein the most 3' nucleotides of primer 1 are identical to the variant nucleotides.

21. The method or the kit according to any one of items 1 to 16, wherein the variant sequence consists of insertion of one or more nucleotides.

22. The method or the kit according to item 21, wherein the most 3' nucleotide(s) of primer 1 are identical to at least the most 5' nucleotide(s) of the insertion.

23. The method or the kit according to item 21, wherein the most 3' nucleotides of primer 1 are identical to all of the inserted nucleotides.

24. The method or the kit according to any one of items 1 to 16, wherein the variant sequence consists of deletion of one or more nucleotides.

25. The method or the kit according to item 24, wherein the most 3' nucleotides of primer 1 are identical to the nucleotides positioned immediately 3' of the deletion.

26. The method or the kit according to any one of the preceding items, wherein primer 1 contains a sequence of in the range of 15 to 50 nucleotides, such as in the range of 15 to 20 nucleotides, which is identical to the target nucleic acid sequence comprising the variant sequence expect for up to one mismatch.

27. The method or the kit according to any one of the preceding items, wherein said sequence of at least 15 nucleotides, which is identical to the target nucleic acid sequence comprising the variant sequence expect for up to one mismatch is positioned at the 3' end of primer 1.

28. The method or the kit according to item 27, wherein said mismatch is positioned at position 2, 3 or 4 from the 3' end.

29. The method or the kit according to any one of the preceding items, wherein primer 2 comprises a sequence of at least 15 nucleotides, which is complementary to a consecutive sequence of the target nucleic acid sequence.

30. The methods or kit according to any one of the preceding items, wherein more than one blocking oligonucleotide is provided.

31. The methods or kit according to any one of the preceding items, wherein more than one primer 1 is provided, wherein each of said primer 1s contain a sequence identical to a consecutive stretch of the target nucleic acid sequence comprising a different variant sequence expect for up to one mismatch.

32. The method or the kit according to any one of the preceding items, wherein the blocking sequence is in the range of 10 to 30 nucleotides, such as in the range of 15 to 25 nucleotides.

33. The method or the kit according to any one of the preceding items, wherein the blocking oligonucleotide has the following general structure 5'-(N)$_a$—Z-SEQ$_1$-Z—(N)$_b$-3' wherein
N is any nucleotide or nucleotide analogue; and
Z is a hydrophobic nucleotide as defined in item 1; and
SEQ$_1$ is a sequence of 4 to 20 nucleotides or nucleotide analogues into which up to 4 hydrophobic nucleotides (Z) may be inserted; and
a and b individually are an integer in the range of 0 to 4; and
the total number of nucleotides is at least 10; and
(N)$_a$-SEQ$_1$-(N)$_b$ is identical to a stretch of the target nucleic acid sequence comprising the reference NOI sequence.

34. The method or the kit according to item 33, wherein SEQ1 is a sequence identical to a stretch of the target nucleic acid sequence comprising the reference NOI sequence.

35. The method or the kit according to any one of the preceding items, wherein the blocking oligonucleotide has the following general structure 5'-(N$_a$—Z—(N)$_c$—Z—(N)$_b$-3' wherein
N is any nucleotide or nucleotide analogue; and
Z is a hydrophobic nucleotide as defined in item 1; and
a and b individually are integers in the range of 0 to 4; and
c is an integer in the range of 4 to 20; and
a+b+c is at least 10; and
(N)$_a$—(N)$_c$—(N)$_b$ is identical to a stretch of the target nucleic acid sequence comprising the reference NOI sequence.

36. The method or the kit according to item 35, wherein N, is a sequence identical to a stretch of the target nucleic acid sequence comprising the reference NOI sequence.

37. The method or the kit according to any one of the preceding items, wherein the blocking oligonucleotide has the following general structure 5'-(N)$_a$—Z—(N)$_d$—Z—(N)$_e$—Z—(N)$_b$-3' wherein
N is any nucleotide or nucleotide analogue; and
Z is a hydrophobic nucleotide as defined in item 1; and
the total number of nucleotides or nucleotide analogues is at least 10; and
a and b individually are integers in the range of 0 to 4; and
d and e individually are integers in the range of 1 to 19; and
a+b+d+e at least 10; and
(N)$_a$—(N)$_d$—(N)$_e$—(N)$_b$ is identical to the reference target sequence.

38. A blocking oligonucleotide having the following general structure

5'-(N)$_a$—Z—(N)$_f$—Z—(N)$_g$—Z—(N)$_h$—Z—(N)$_b$-3' wherein
N is any nucleotide or nucleotide analogue; and
Z is a hydrophobic nucleotide as defined in item 1; and
a and b individually are integers in the range of 0 to 4; and
f, g and h individually are integers in the range of 1 to 18; and
a+b+f+g+h is at least 10 and at the most 50; and
(N)$_a$—(N)$_f$—(N)$_g$—(N)$_h$—(N)$_b$ is identical to a stretch of the target nucleic acid sequence comprising the reference NOI sequence.

39. A blocking oligonucleotide having the following general structure

5'-(N)$_a$—Z—(N)$_i$—Z—(N)$_j$—Z—(N)$_k$—Z—(N)$_l$—Z—(N)$_b$-3' wherein
N is any nucleotide or nucleotide analogue; and
Z is a hydrophobic nucleotide as defined in item 1; and
a and b individually are integers in the range from 0 to 4; and
j, k and l individually are integers in the range from 1 to 17; and
a+b+i+j+k+l is at least 10 and at the most 50; and
(N)$_a$—(N)$_i$—(N)$_j$—(N)$_k$—(N)$_l$—(N)$_b$ is identical to a stretch of the target nucleic acid sequence comprising the reference NOI sequence.

40. A blocking oligonucleotide having the following general structure

5'-(N)$_a$—Z—(N)$_m$—Z—(N)$_n$—Z—(N)$_o$—Z—(N)$_p$—(N)$_q$—Z—(N)$_b$-3' wherein
N is any nucleotide or nucleotide analogue; and
Z is a hydrophobic nucleotide as defined in item 1; and
a and b individually are integers in the range of 0 to 4; and
m, n, o, p and q individually are integers in the range of 1 to 16; and
a+b+m+n+o+p+q is at least 10 and at the most 50; and
(N)$_a$—(N)$_m$—(N)$_n$—(N)$_o$—(N)$_p$—Z—(N)$_q$—(N)$_b$ is identical to a stretch of the target nucleic acid sequence comprising the reference NOI sequence.

41. The method or the kit according to any one of items 1 to 32, wherein the blocking oligonucleotide is the blocking oligonucleotide according to any one of items 37 to 39.

42. The method, the kit or the blocking oligonucleotide according to any one of the preceding items, wherein a is an integer in the range of 0 to 1, for example a is 0.

43. The method, the kit or the blocking oligonucleotide according to any one of the preceding items, wherein b is an integer in the range of 0 to 3, for example b may be 0 or b may be 1.

44. The method, the kit or the blocking oligonucleotide according to any one of the preceding items, wherein at least one intercalator is a flat conjugated system.

45. The method, the kit or the blocking oligonucleotide according to any one of the preceding items, wherein at least one intercalator, Q, is selected from the group consisting of polyaromates and heteropolyaromates optionally substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl and amido.

46. The method, the kit or the blocking oligonucleotide according to item 45, wherein the intercalator is selected from the group consisting of benzene, pentalene, indene, naphthalene, azulene, as-indacene, s-indacene, biphenylene, acenaphthylene, Phenalene, heptalene, phenanthrene, fluoranthene, phenanthroline, phenazine, phenanthridine, anthraquinone, pyrene, anthracene, napthene, phenanthrene, flurene, picene, chrysene, naphtacene, acridones, benzanthracenes, stilbenes, oxalo-pyridocarbazoles, azidobenzenes, porphyrins and psoralens and derivatives thereof thereof.

47. The method, the kit or the blocking oligonucleotide according to any one of the preceding items, wherein at least one intercalator, Q, is selected from the group consisting of:

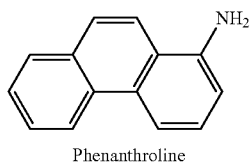

Phenanthroline

V

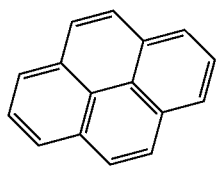

Pyrene

XII

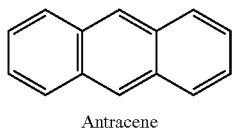

Antracene

XIV

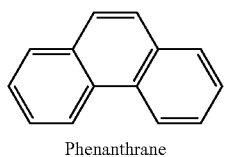

Phenanthrane

XV

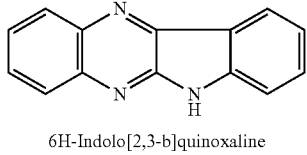

6H-Indolo[2,3-b]quinoxaline

XVII

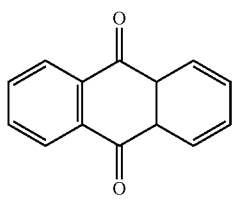

9,10-Anthracenedione

XXIII

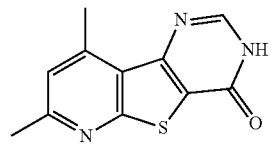

Pyrido[3',2':4,5]thieno[3,2-d]pyrimidin-4(1H)-one, 7,9-dimethyl-

XXVI

-continued

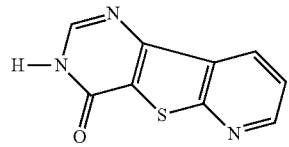

Pyrido[3',2':4,5]thieno[3,2-d]pyrimidin-4(1H)-one

XLVIII

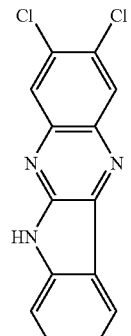

and

LI

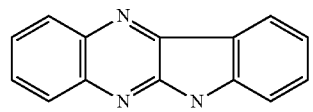

LII

48. The method, the kit or the blocking oligonucleotide according to any one of the preceding items, wherein at least one hydrophobic group is comprising pyrene or pyrido[3',2':4,5]thieno[3,2-d]pyrimidin-4(1H)-one or 7,9-dimethyl-pyrido[3',2':4,5]thieno[3,2-d]pyrimidin-4(3H)-one.

49. The method, the kit or the blocking oligonucleotide according to any one of the preceding items, wherein all intercalators, Q, are the same.

50. The method, the kit or the blocking oligonucleotide according to any one of the preceding items, wherein at least one backbone monomer unit X is selected from the group consisting of phosphoramidites.

51. The method, the kit or the blocking oligonucleotide according to any one of the preceding items, wherein at least one linker, Y, comprises a chain of x atoms selected from the group consisting of C, O, S, N and P.

52. The method, the kit or the blocking oligonucleotide according to item 51, wherein the chain is substituted with one or more selected from the group consisting of C, H, O, S, N and P.

53. A method of predicting the efficacy of treatment of a clinical condition in an individual in need thereof with a predetermined drug, wherein the efficacy of treatment of said clinical condition with said drug is associated with the presence of a variant sequence, said method comprising the steps of
   a. providing a sample from said individual
   b. performing the method according to any one of items 1, 2, 3, 10 to 37 and 41 to 52 to determine the presence of said variant sequence;
   wherein the presence of said variant sequence is indicative of whether said drug is efficient in treating said clinical condition in said individual.

54. The method according to item 53, wherein the clinical condition is cancer and the variant sequence is an activating mutation in KRAS or NRAS.

55. The method according to item 53, wherein the presence of an activating mutation in KRAS or NRAS is indicative of antibodies to EGFR not being effective for treatment of cancer in said individual.
56. A method of predicting the presence of a clinical condition in an individual in need thereof, wherein said clinical condition is associated with a target nucleic acid sequence comprising a variant sequence, said method comprising the steps of
   a. providing a sample from said individual
   b. performing the method according to any one of items 1, 2, 3, 10 to 37 and 41 to 52 to determine the presence of said variant sequence;
      wherein the presence of said variant sequence is indicative of said individual suffering from said clinical condition.
57. The method according to item 56, wherein the clinical condition is cancer.
58. The method according to any one of items 53 to 57, wherein the variant sequence is a single nucleotide variant.
59. The method according to item 58, wherein the single nucleotide variant is selected from mutations in positions 12, 13, 59, 61, 117 and 146 of KRAS and mutation in positions 12, 13, 61, 117, 148 of NRAS.
60. The method according to any one of items 52 to 58, wherein the mutation is selected from the group of mutations shown in Table 1.

EXAMPLES

The invention is further illustrated by the following examples, which should however not be construed as being limiting for the invention.

As described above, the methods of the invention comprise a step of performing a PCR. Said PCR may be performed in any useful manner e.g. by qPCR. In the following examples, qPCR was performed in 25 µl reactions in KAPA Probe Fast qPCR 2× Master Mix (KAPA Biosystems KM4711) on a Corbett Rotor-Gene 6000 real-time PCR system using 50 ng wild type DNA (Promega G304A) in the absence and presence of approximately 1000 copies of plasmid DNA containing the indicated mutations. The thermocycling conditions used were: 2 min of initial activation of the hotstart taq-polymerase at 95° C., followed by 45 cycles of a 2-step PCR with a 15 sec denaturation step at 94° C. and 60 sec extension step at 60° C.

Example 1

The present invention is based on the use of a blocking oligonucleotide comprising at least two hydrophobic nucleotides as defined in claim 1 and where at least part of the sequence of said blocking oligonucleotide is fully identical to a target nucleic acid sequence comprising a reference NOI sequence. The blocking oligonucleotide may suppress the signal (here measured as the threshold cycle, $C_T$), wherein suppressing by the blocking oligonucleotide is observed as $C_T$ being delayed/higher. In addition, in some embodiments it is preferred that the sequence of said blocking oligonucleotide analogue is partly but not fully identical to at least the last 3 nucleotides of the 3' end of at least one of the primers used together with said blocking oligonucleotide (herein referred to as Primer 1). Three examples of useful design of the blocking oligonucleotide are described below. The first example illustrated in FIG. 1 is with a medium overlap of primer 1 and the blocking oligonucleotide, the second example illustrated in FIG. 2 is showing a larger overlap between primer 1 and the blocking oligonucleotide and the last example illustrated in FIG. 3A is showing a minimum overlap between primer 1 and the blocking oligonucleotide according to the present invention. These illustrations only serve as examples and should not limit the design or variation between primer 1 and the blocking nucleotide to any further extent than what is described in the claims of the present application.

FIG. 1 illustrates an example of how primer 1 according to the present invention shown in A) can overlap partly with the blocking oligonucleotide shown in B). The stars in primer 1 and the blocking oligonucleotide indicate a sequence of nucleotides that in the present example are identical to each other in said primer and blocking oligonucleotide. The black circle indicates a mismatch where the nucleotide is not identical to the nucleotide of the similar position in the blocking oligonucleotide (marked by a white circle), nor identical to the target nucleic acid sequence. The triangle at the tip of the primer (the 3' end of primer 1) indicates a nucleotide that is identical to the variant sequence. The blocking oligonucleotide has a different nucleotide in the corresponding position (marked by a heart). This nucleotide is identical to the reference NOI sequence. The grey squares illustrate nucleotides where primer 1 and the blocking oligonucleotide do not overlap. "Z" exemplifies positioning of hydrophobic nucleotides according to the present invention.

Said Blocking oligonucleotide can also be partly but not fully identical to a larger portion of said primer 1. Thus, in one embodiment of the invention the 5' end of primer 1 is identical to a consecutive stretch of the target nucleic acid sequence of for example in the range of 10 to 25 nucleotides, typically 10 to 20 nucleotides and the middle part is in addition also identical to a consecutive stretch of the blocking sequence. This part may for example consist of in the range of 3 to 8 nucleotides. The 3' end may consist of a mismatch followed by a few nucleotides (e.g. 1 to 3 nucleotides) identical to a stretch of the target nucleic acid sequence. The very 3' nucleotide(s) of primer 1 may be identical to the variant sequence.

FIG. 2 illustrates a larger overlap of identical sequence between primer 1 and the blocking oligonucleotide. Similar notation as used in FIG. 1 above. Thus, in one embodiment of the invention the 5' end of primer 1 is identical to a consecutive stretch of the target nucleic acid sequence of for example in the range of 10 to 25 nucleotides, typically in the range of 10 to 20 nucleotides and the middle part is in addition also identical to a consecutive stretch of the blocking sequence. This part may for example consist of in the range of 8 to 15 nucleotides. The 3' end may consist of a mismatch followed by a few nucleotides (e.g. 1 to 3 nucleotides) identical to a stretch of the target nucleic acid sequence. The very 3' nucleotide(s) of primer 1 may be identical to the variant sequence. It is also possible that primer 1 may consist of a sequence, which is identical to a consecutive stretch of the blocking sequence except for one mismatch and the variant sequence specific nucleotide. In particular, the entire 5' end of Primer 1 may be identical to a consecutive stretch of the blocking sequence of in the range of 10 to 15 nucleotides.

However, the overlap between primer 1 and the blocking oligonucleotide can also be less. This is illustrated in FIG. 3. In the example shown here below, we illustrate the smallest overlap possible according to the present invention between primer 1 and the blocking oligonucleotide.

FIG. 3A illustrates a minimum overlap between primer 1 and the blocking oligonucleotide. Similar notation as used in FIG. 1 above. The overlap only shares one identical nucleotide. Next to said nucleotide the variant sequence-specific nucleotide is positioned in the primer 1 and the reference NOI sequence-specific nucleotide in the blocking oligonucleotide. Furthermore, there is potentially a mismatch in primer 1 that is not found in the blocking oligonucleotide nor is identical to the target nucleic acid sequence. This means that as little as down to one nucleotide in the overlap is identical between primer 1 and the blocking oligonucleotide. Similar notation as used in FIG. 1 above. Thus, in one embodiment of the invention the 5' end of primer 1 is identical to a consecutive stretch of the target nucleic acid sequence of for example in the range of 10 to 25 nucleotides, typically in the range of 10 to 20 nucleotides. The 3' end may consist of a mismatch followed by a few nucleotides (e.g. 1 to 3 nucleotides) identical to a stretch of the target nucleic acid sequence. The very 3' nucleotide(s) of primer 1 may be identical to the variant sequence.

Example 2

Blocking Oligonucleotide Increases Specificity in Simplex Reactions

In this example, we illustrate how the addition of a blocking oligonucleotide according to the present invention can increase the specificity, $\Delta C_T$, of a PCR (measured as the $C_T$ from a target nucleic acid sequence comprising the variant sequence minus the $C_T$ when there is only reference target sequence present, background signal).

Figure 4:
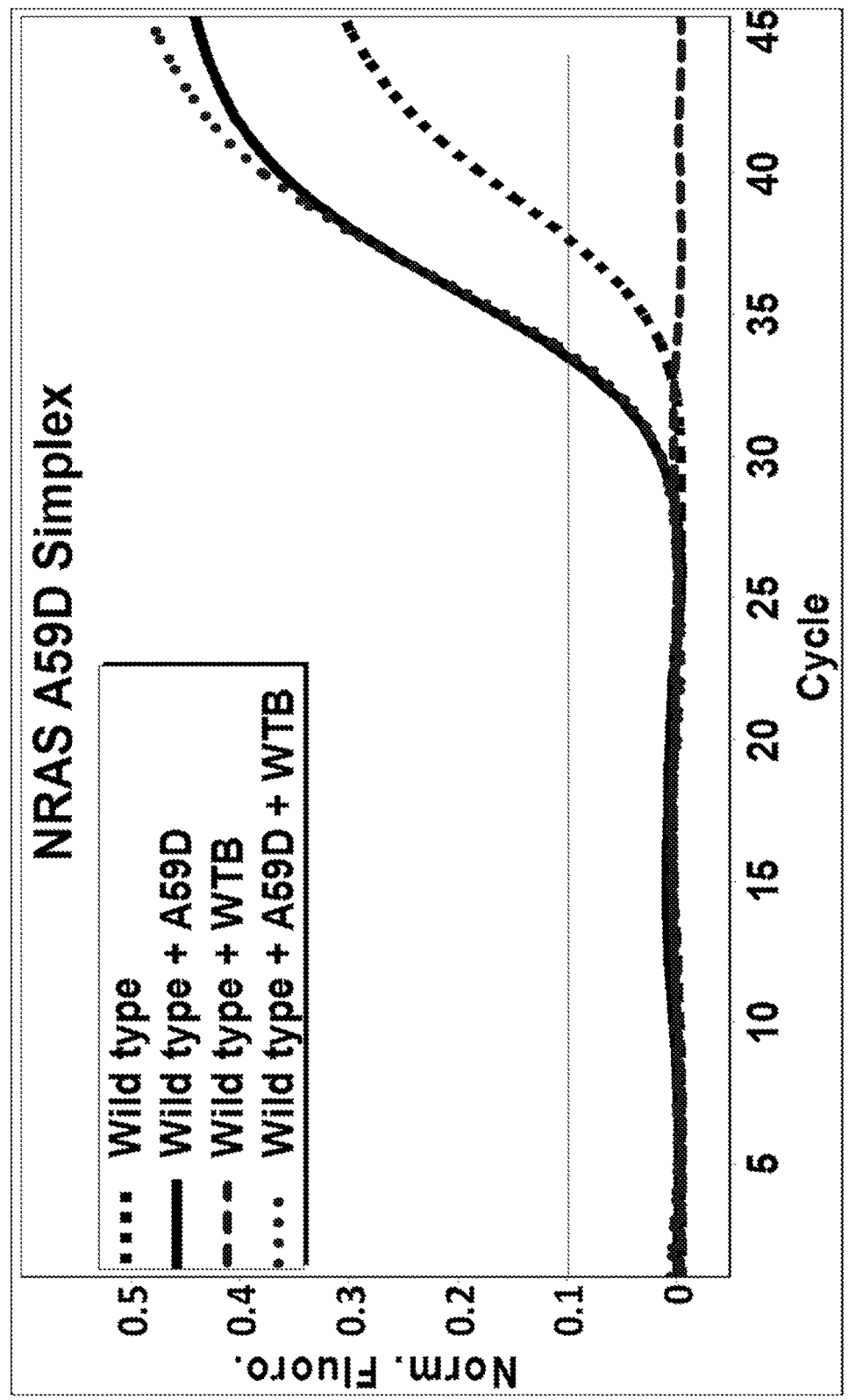
FIG. 4 shows the result of a PCR using either a wild type NRAS template or a mixture of wild type and A59D mutant NRAS template. Primer 1 is designated "NRAS A59D forward", primer 2 is designated "NRAS 59 reverse", and the blocking oligonucleotide is designated "NRAS 59 BaseBlocker". Z indicates a hydrophobic nucleotide. WTB indicates the presence of blocking oligonucleotide. A) The graph shows the PCR signal (fluorescence signal from the NRAS59 probe) in relation to the PCR cycle number. B) Shows primers, probes and blocking oligonucleotide sequences used. The horizontal line represents a signal of 0.1.

The present example is illustrating how addition of a blocking oligonucleotide according to the present application identical to the reference sequence comprising the wild type (WT) version of codon 59 of NRAS (Ala59) can remove the signal ($C_{T, WT}$) from a WT template, while at the same time only have minimal effect on the signal (measured as $C_{T, NRASA59D}$) from the variant sequence comprising a NRAS Ala59Asp (A59D) mutation (see FIG. 4).

FIG. 4 shows that blocking oligonucleotides described in the present invention are highly specific. Addition of a blocking oligonucleotide identical to the Wild Type (WTB) part of a sequence of NRAS exon 3 codon 59 (Ala59) completely blocks amplification of wild type DNA without blocking allele-specific amplification of NRAS Ala59Asp (A59D) mutated DNA.

In the sequence of the blocking oligonucleotide (NRAS 59 BaseBlocker), Z indicates a hydrophobic nucleotide. The hydrophobic nucleotide has a phosphoramidit backbone connected to pyrene via a linker.

Similar experiments were made using a variety of different primers and blocking oligonucleotides for detecting the mutations indicated in FIG. 3B in various target genes. The sequences of Primer 1, Primer 2 and the Blocking oligonucleotides used in assays no. 1 to 6 are shown in FIG. 3B. PCR amplifications were made essentially as described above and similar results were obtained using the primers of FIG. 3B, showing that different combinations of primers and blocking oligonucleotides can be designed and used with the present methods.

Figure 5:
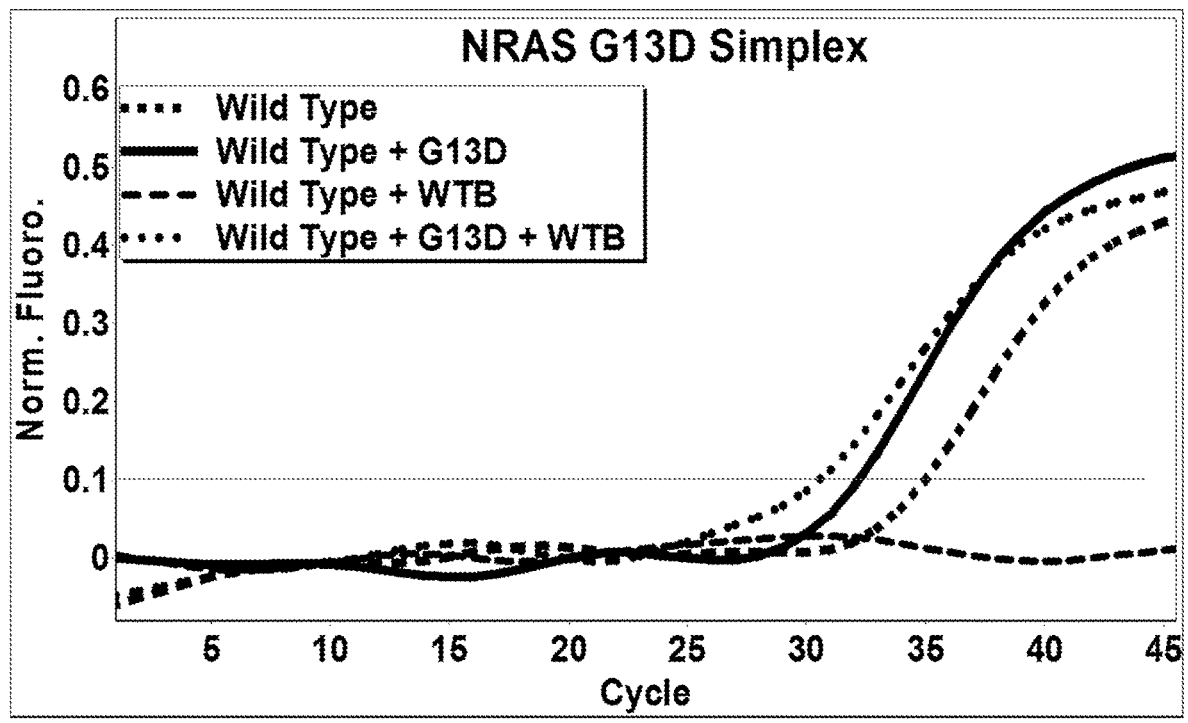
FIG. 5 shows the results of a PCR using either a wild type NRAS template or a mixture of wild type and G13D mutant NRAS template. Primer 1 is specific for the NRAS G13D mutation, whereas the blocking oligonucleotide is specific for wild type NRAS. The graph shows the PCR signal (fluorescence signal from a probe) in relation to the PCR cycle number. WTB indicates the presence of blocking oligonucleotide. The horizontal line represents a signal of 0.1.

In a similar example, we illustrate how addition of a blocking oligonucleotide according to the present invention identical to the WT sequence comprising codon 13 of NRAS (Gly13) can suppress amplification from a WT template as seen as delayed or absent signal at the threshold ($C_{T, WT}$), with minimal effect on the amplification ($C_{T, NRASG13D}$) from the template comprising a NRAS Gly13Asp (G13D) mutation (see FIG. 5).

FIG. 5 shows that a blocking oligonucleotide designed as described in the present invention is highly specific. Addition of a Blocking oligonucleotide identical to the Wild Type (WTB) part of a sequence of NRAS exon 2 codon 13 (Gly13) completely blocks amplification of wild type DNA without blocking allele-specific amplification of NRAS Gly13Asp (G13D) mutated DNA.

It s not always possible to design a Blocking oligonucleotide that will totally remove the signal from one template while leaving a template with as little as one base pair change unaffected. However, a well designed Blocking oligonucleotide according to the present invention, should be able to significantly inhibit the amplification of the reference NOI sequence over the variant sequence under given conditions.

Example 3

Blocking Oligonucleotide Increases Specificity Towards a Certain Variant Sequence in a Simplex Reaction A Blocking oligonucleotide as described in the present invention may also be used to increase specificity of a PCR reaction towards a particular variant sequence. Thus, in the example illustrated in FIG. 6, we show how addition of a Blocking oligonucleotide according to the present invention identical to the KRAS Gly12Arg (G12R) allele comprising variant sequence 1 suppresses amplification from the KRAS Gly12Arg template as seen as a delayed signal at the threshold ($C_{T, KRAsGly12Arg}$), with minimal effect on the amplification of the KRAS Gly12Val (G12V) template comprising variant sequence 2 (Ct, $_{KRASGly12Val}$).

Figure 6:
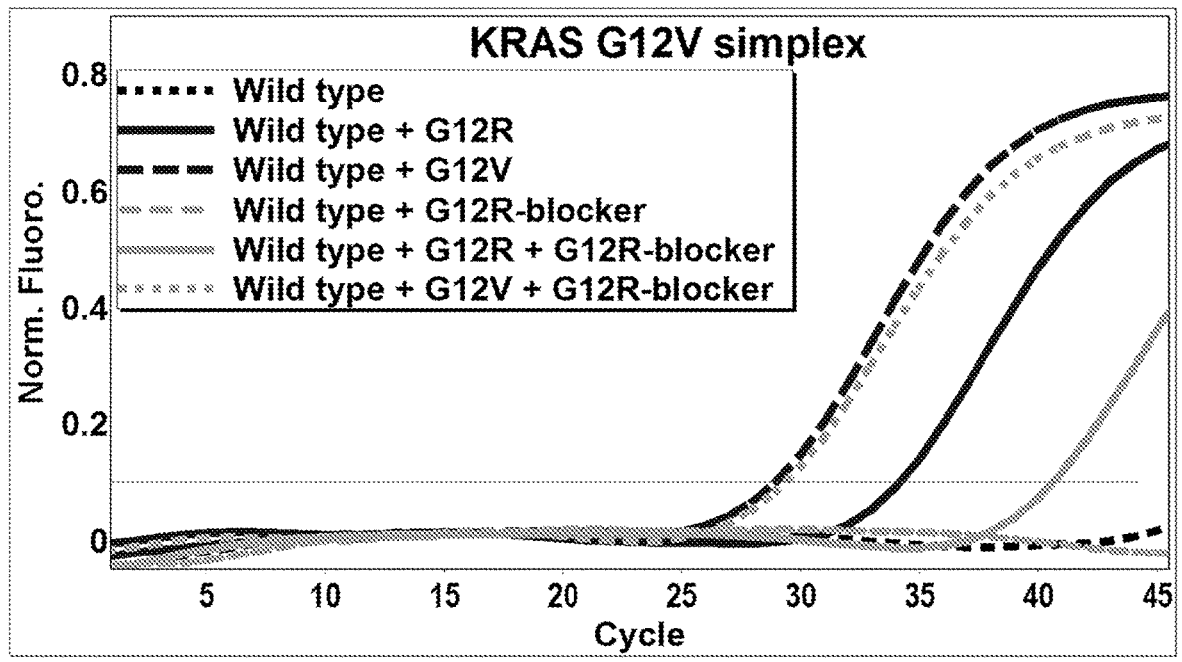
FIG. 6 shows the results of a PCR using different mixtures of KRAS templates (wild type KRAS, G12R KRAS and/or G12V KRAS template). Primer 1 is specific for the KRAS G12V mutation. A blocking oligonucleotide specific for wild type KRAS was added to all mixtures. Furthermore, a blocking oligonucleotide identical to a stretch of the KRAS Gly12Arg (G12R) allele containing the mutation was added (designated G12R-blocker). The graph shows the PCR signal (fluorescence signal from a probe) in relation to the PCR cycle number. The horizontal line represents a signal of 0.1.

FIG. 6 shows that a. blocking oligonucleotide designed as described in the present invention also can be highly specific towards a non-WT reference NOI sequence preferentially inhibiting this over a variant sequence. An assay for the detection KRAS Gly12Val (G12V) containing a wild type blocker was supplemented with a Blocking oligonucleotide identical to the KRAS Gly12Arg (G12R) allele. The allele-specific blocking oligonucleotide significantly impairs amplification of the G12R allele with negligible effect on amplification of the KRAS Gly12Val (G12V) allele.

Example 4

Blocking Oligonucleotide Increases Specificity of a Multiplex Reaction

In this example, we illustrate how the addition of a Blocking oligonucleotide according to the present invention can increase the specificity, $\Delta C_T$, (measured as the $C_T$ from a target in question minus the $C_T$ when said target is absent, background signal) in multiplex reactions.

Figure 7:
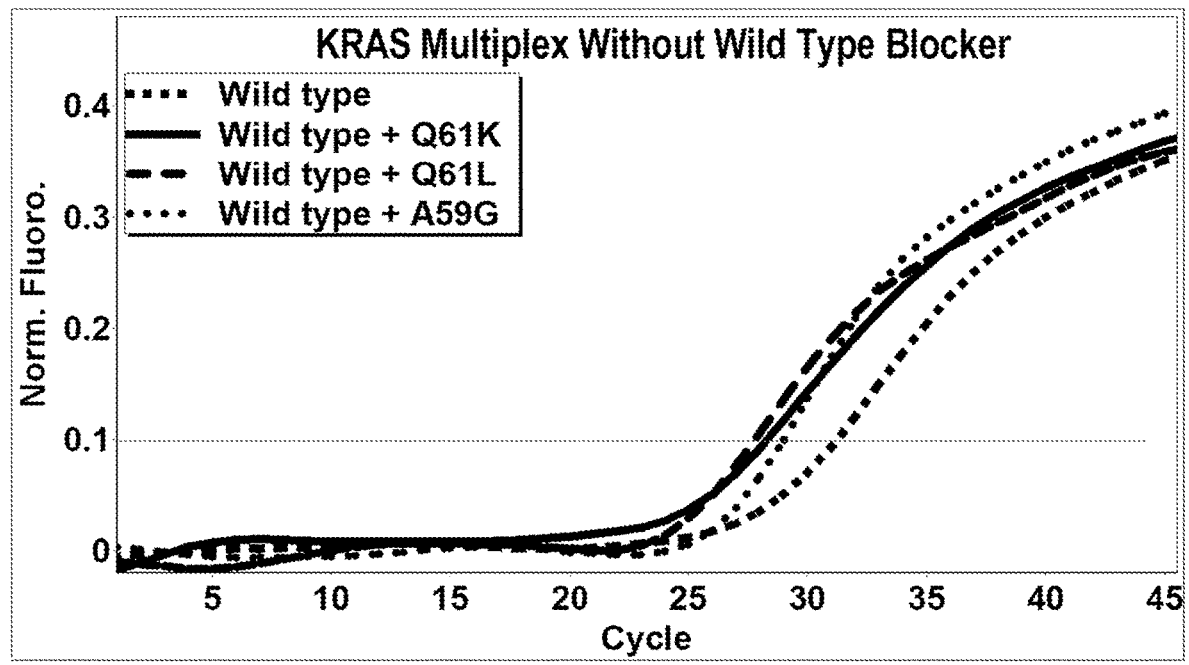
FIG. 7 shows the results of a PCR using either a wild type KRAS template or a mixture of wild type and mutant KRAS template as indicated. Panel A shows the results without addition of a blocking oligonucleotide, whereas panel B shows the results in the presence of a blocking oligonucleotide. The horizontal line represents a signal of 0.1. Three different Primer is are used designated "KRAS Q61K Reverse", "KRAS Q61L Reverse" and "KRAS A59G Reverse", respectively. Primer 2 is designated "KRAS 59/61 forward", and the blocking oligonucleotide is designated "KRAS 59/61 BaseBlocker". Z indicates a hydrophobic nucleotide. The graphs in the upper and middle panels show the PCR signal (fluorescence signal from the KRAS61 probe) in relation to the PCR cycle number.
Figure 7:
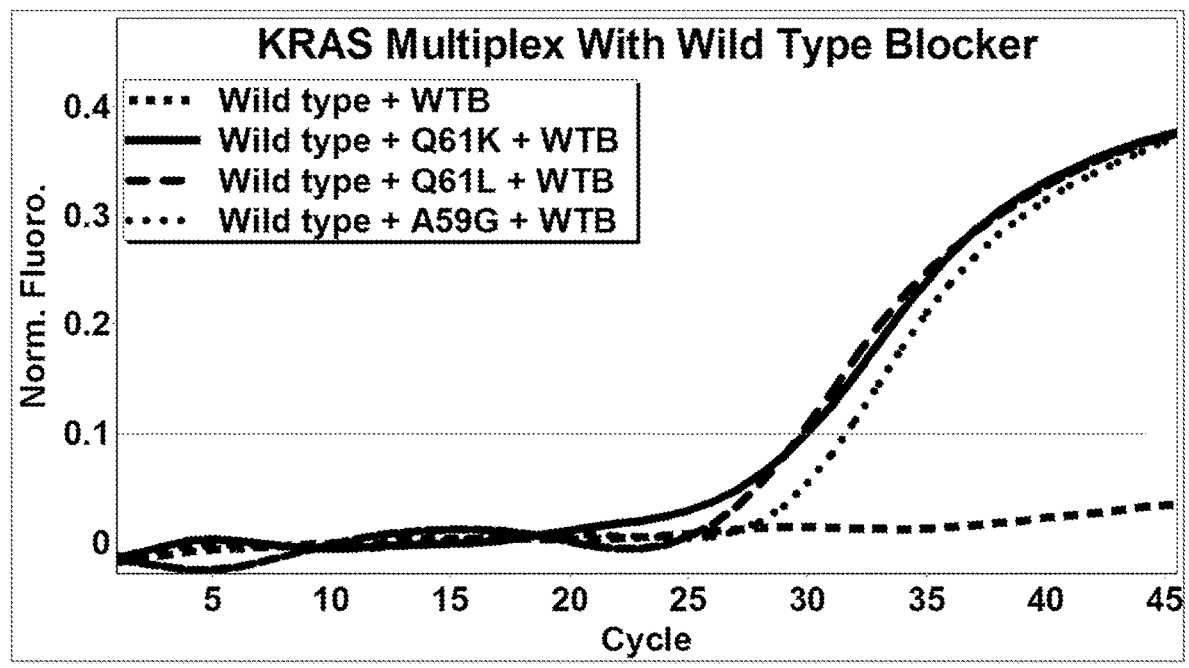

The present example is illustrating how addition of a Blocking oligonucleotide identical to the WT sequence comprising codon 59 (Ala59) and codon 61 (Gln61) of KRAS can reduce the signal ($C_{T, WT}$) from a WT template significantly while only having a minimal effect on the $C_{T, KRAS\ A59G}$, $C_{T, KRAS\ Q61K}$ and $C_{T, KRAS\ Q61L}$ from target nucleic acid sequences comprising KRAS Ala59Gly (A59G), Gln61Lys (Q61K) and Gln61Leu (Q61L) mutations respectively (FIG. 7).

FIG. 7 shows that Blocking oligonucleotides described in the present invention are highly specific. Addition of a blocking oligonucleotide identical to the Wild Type (WTB) sequence of KRAS exon 3 codon 59 (ala59) and codon 61 (Gln61) completely blocks amplification of wild type DNA without blocking allele-specific amplification of KRAS Ala59Gly (A59G), Gln61Lys (Q61K) and Gln61Leu (Q61L) mutated DNA in a multiplex reaction.

Figure 8:
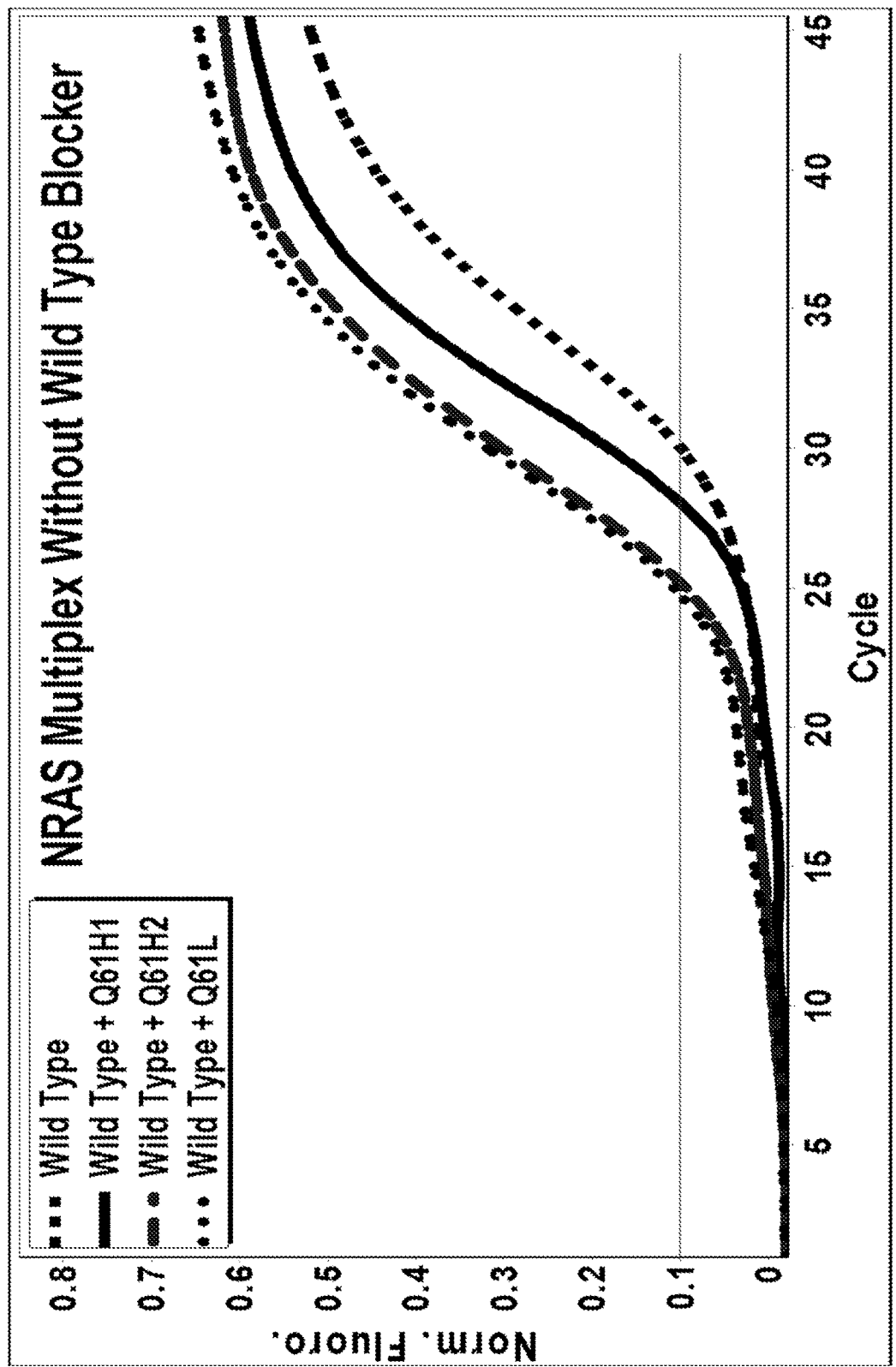
FIG. 8 shows the results of a PCR using either a wild type NRAS template or a mixture of wild type and mutant NRAS template as indicated. Panel A shows the results without addition of a blocking oligonucleotide, whereas panel B shows the results in the presence of a blocking oligonucleotide. Three different Primer 1s specific for NRAS Q61H1, NRAS Q61H2 and NRAS Q61L), respectively were used. The graphs show the PCR signal (fluorescence signal from a probe) in relation to the PCR cycle number. The horizontal line represents a signal of 0.1.
Figure 8:
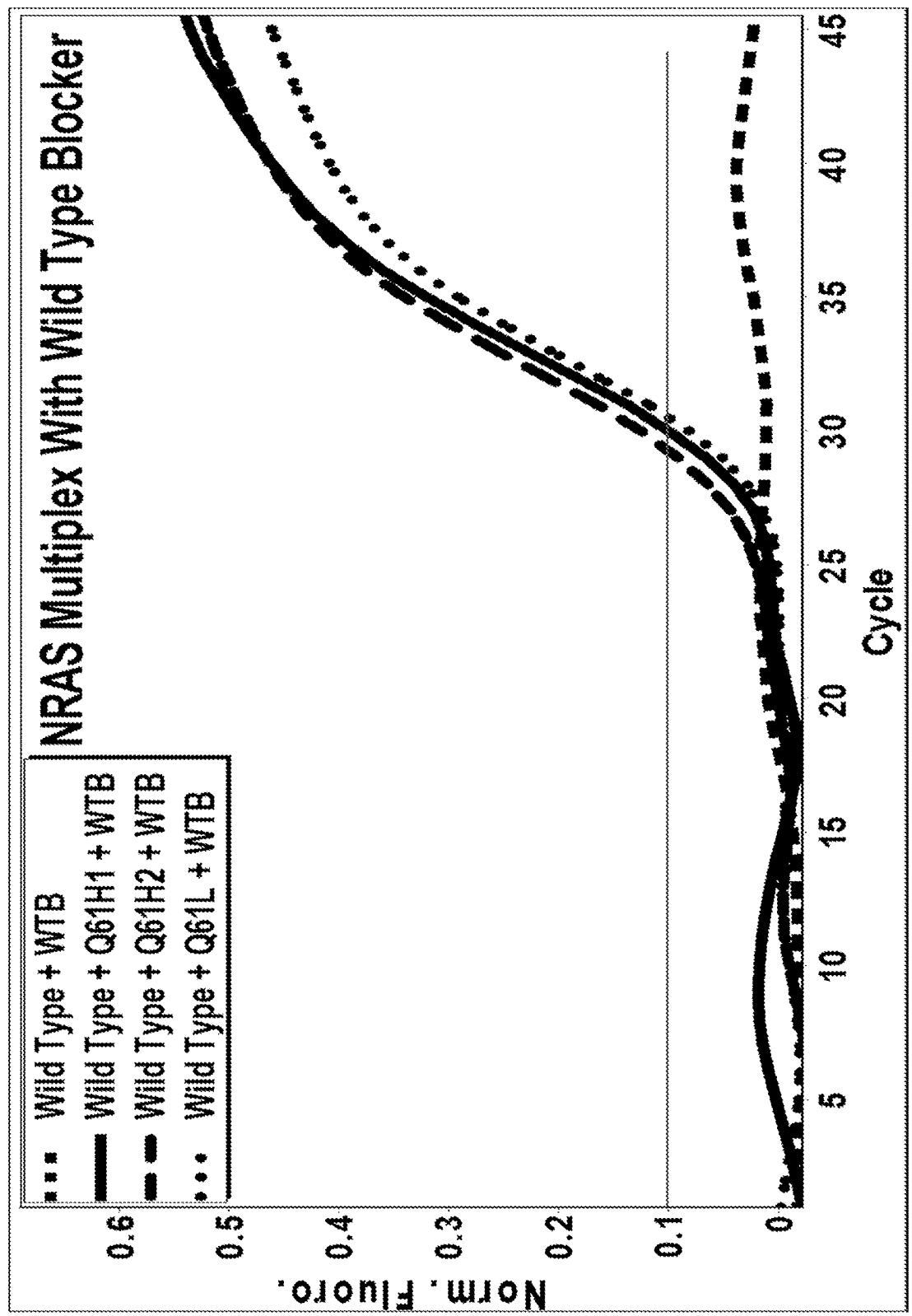

In a similar example, we illustrate how addition of a Blocking oligonucleotide identical to the WT sequence comprising codon 61 of NRAS (Gln61) can remove the signal ($C_{T, WT}$) from a WT template with minimal effect on the $C_{T, NRAS\ Q61H1}$, $C_{T, NRAS\ Q61H2}$ and $C_{T, NRAS\ Q61L}$ from the template comprising a NRAS Gln61His$^{A>C}$ (Q61H1), Gln61His$^{A>T}$ (Q61H2) and Gln61Leu (Q61L) mutations in a multiplex reaction respectively (FIG. 8).

FIG. 8 shows that Blocking oligonucleotides described in the present invention are highly specific. Addition of a blocking oligonucleotide comprising a sequence that is identical to the Wild Type (WTB) part of a sequence of NRAS exon 3 codon 61 (Gln61) completely blocks amplification of wild type DNA and at the same time only have a minor inhibition effect on the allele-specific amplification of NRAS Gln61His$^{A>C}$ (Q61H1), Gln61His$^{A>T}$ (Q61H2) and Gln61Leu (Q61L) mutations in a multiplex reaction.

Example 5

Assays Designed in Accordance to the Present Invention Show Extremely High Sensitivity Assays were designed in accordance to present invention and evaluated with respect to sensitivity towards the mutant template containing the variant sequence in a background of wild type template DNA. Each assay consists of an allele-specific primer set, a HydrolEasy™ hydrolysis probe and a blocking oligonucleotide according to the present invention. The primer set consists of a wild type primer (Primer 2) and an allele-specific primer comprising one mismatch (Primer 1). The Blocking oligonucleotide overlaps with the allele-specific primer and blocks amplification of wild type DNA.

Figure 9:
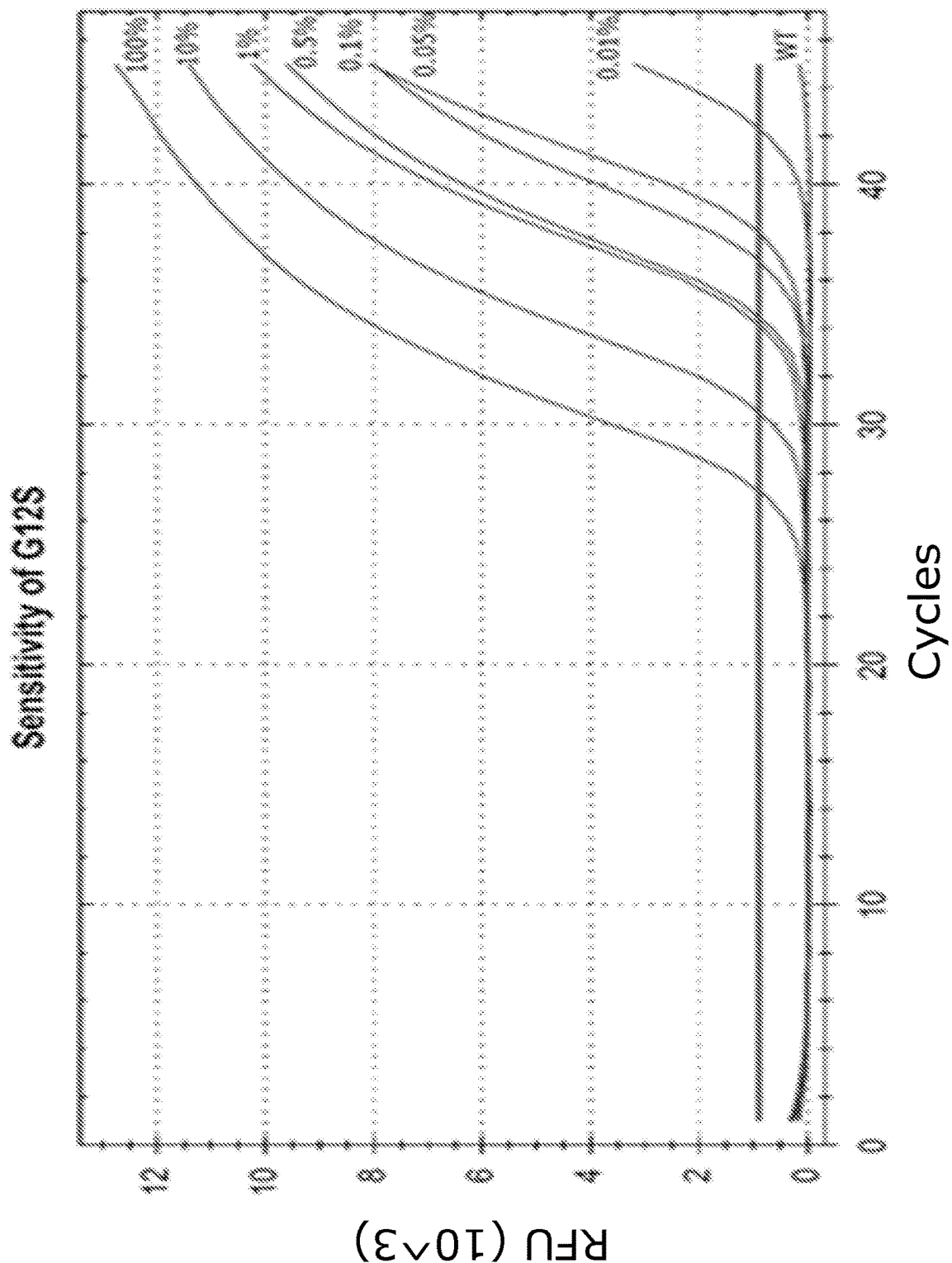
FIG. 9 shows two examples of sensitivity studies, where the assays according to present invention are detecting dilution series of the variant sequence in a background of wildtype DNA.
Figure 9:
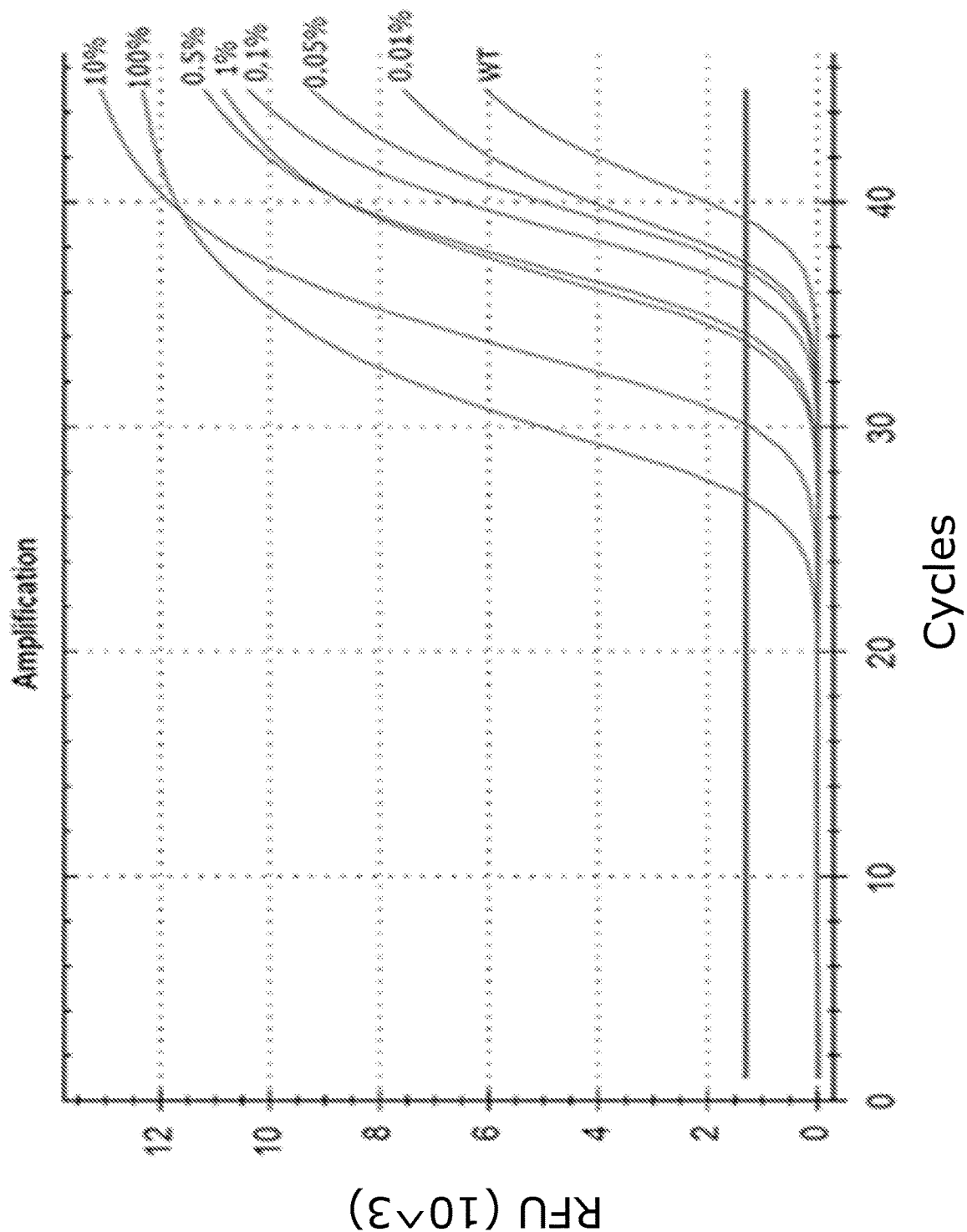

FIG. 9 shows that assays designed in accordance to present invention can exhibit an extremely high sensitivity. Sensitivity was assessed using 50 nG of human cell-line gDNA in each reaction. The percentage corresponds to how much of the DNA added is from the cell line CCL-185 comprising the G12S mutation (A) or the SW403 cell line comprising the G12V mutation (B). The remaining DNA was extracted from the DIFI cell line (WT with respect to KRAS exon 2 codons 12 and 13). Using an assay according to present invention, it is possible to get a distinction between having 0.01% of mutated template in a background of WT template or having no mutated template in both simplex (A) and multiplex reactions (B).

| Well | Fluorophore | Target | Content | Sample | Cq |
|---|---|---|---|---|---|
| C01 | FAM | M2 | Unkn | 100 V | 26, 37 |
| C02 | FAM | M2 | Unkn | 10 V | 29, 63 |
| C03 | FAM | M2 | Unkn | 1 V | 33, 27 |
| C04 | FAM | M2 | Unkn | 0.5 V | 33, 66 |
| C05 | FAM | M2 | Unkn | 0.1 V | 35, 58 |
| C06 | FAM | M2 | Unkn | 0.05 V | 36, 50 |
| C07 | FAM | M2 | Unkn | 0.01 V | 36, 89 |
| C08 | FAM | M2 | Unkn | 0 | 38, 79 |

Table 2. Quantification cycle (Cq) values for G12V detection in a multiplex qPCR reaction when setting the threshold to RFU=1,000. It can be seen that the more diluted the mutated sample is, the higher the Cq value gets. Furthermore, it is obvious from above results that it is possible to detect a very low amount (0.01%) of DNA comprising a single point mutation in 50 nG total DNA input, with a signal that is significantly different from when no mutation is present (100% wild type).

Example 6

Comparison with Other Tests

Three different clinical studies were performed to compare the performance of the present method, termed SensiScreen®, to 4 common methods for detection of KRAS exon 2 mutation testing. Formalin-fixed paraffin-embedded DNA from three different patient populations with histologically confirmed colorectal cancer was analysed for the presence of 7 clinically relevant mutations in KRAS exon 2 codons 12 and 13.

Cobas®

The cobas® KRAS Mutation Test, (Roche Molecular Diagnostics), for use with the cobas® 4800 System, is a real-time PCR test intended for the identification of mutations in codons 12, 13 and 61 of the KRAS gene in DNA derived from formalin-fixed, paraffin-embedded human colorectal cancer (CRC) tissue. In formalin-fixed, paraffin-embedded tissue (FFPET), the cobas® KRAS Mutation Test can detect <5% mutant sequence copies in a background of wild-type DNA.

Direct Sequencing

Direct sequencing, also known as Sanger sequencing, is considered the gold-standard DNA sequencing method. Direct sequencing is based on the selective incorporation of chain-terminating dideoxynucleotides by DNA polymerase during in vitro DNA replication. In the dye-terminator method variant, each of the four chain terminating dideoxy-nucleotides is labelled with a specific fluorescent dye which emits light at distinct wavelengths. The mutational analyses of KRAS exon 2 by direct sequencing were performed using an ABI3130 Genetic Analyzer (Applied Biosystems) and evaluated with Sequencing Navigator Software (Applied Biosystems).

Therascreen

The therascreen KRAS test (Qiagen) is an FDA-approved test for KRAS mutation detection, therascreen is a real-time PCR test that performs allele-specific amplification using the amplification-refractory mutation system (ARMS) principle of allele-specific PCR scorpion primers that are covalently linked to a probe. The therascreen provides 8 separate PCR amplification reactions: 7 mutation-specific reactions in codons 12 and 13 of exon 2 of the KRAS oncogene, and a wild-type control in exon 4.

Mutant-Enriched PCR

Mutant-enriched PCR combines PCR amplification with restriction enzyme digestion to enrich for mutant alleles, while wt alleles are eliminated by digestion. Analyses of KRAS exon 2 mutations by mutant-enriched PCR were performed by introducing a restriction site, BstNI or BglI for codon 12 or 13, respectively, during the first PCR step, localized in the immediate vicinity of the K-ras codon to distinguish between wild-type and mutant sequences. Wild-type amplicons were then digested by BstNI or BglI restriction enzyme, whereas mutant products were enriched for a second round of amplifications. ME-PCR products were subsequently subjected to automated sequencing on an ABI PRISM 3130 Genetic Analyzer (Applied Biosystems).

The results of the comparative studies can be seen in FIG. 10. The figure shows that SensiScreen® identifies 4(5%), 19(41%), 1(5%), and 2(5%) additional mutation positive cases compared to cobas®, direct sequencing, therascreen and mutant-enriched PCR, respectively. SensiScreen® thus displays improved performance compared to the tested methods of the prior art.

The invention claimed is:

1. A method for detecting the presence of a more than one of a number of variant sequences in a target nucleic acid sequence comprising nucleotide(s) of interest (NOI), wherein said NOI may consist of said variant sequences, of other variant sequences or of a reference NOI sequence, said method comprising the steps of
   a) providing a sample comprising nucleic acids
   b) providing one blocking oligonucleotide comprising a sequence of in the range of 10 to 50 nucleotides (referred to as "blocking sequence") into which in the range of 2 to 10 hydrophobic nucleotides have been inserted wherein
   at least one hydrophobic nucleotide is positioned at the 5' end of said sequence or within 4 nucleotides from the 5' end; and
   at least one hydrophobic nucleotide is positioned at the 3' end of said sequence or within 4 nucleotides from the 3' end; and wherein the hydrophobic nucleotide has the structure

X—Y-Q wherein
X is a nucleotide or nucleotide analogue or a backbone monomer unit,
Q is a intercalator which is not taking part in Watson-Crick hydrogen bonding; and
Y is a linker moiety linking said nucleotide or nucleotide analogue or backbone monomer unit and said intercalator; and
wherein the blocking sequence is identical to a consecutive stretch of the target nucleic acid sequence comprising the reference NOI sequence,
c) providing sets of primers comprising at least two different primers including a first primer 1 and a primer 2, wherein the first primer 1 together with the primer 2 is capable of amplification of the target nucleic acid sequence comprising a first variant sequence, and wherein first primer 1 comprises a sequence of at least 15 nucleotides positioned at the 3' end of said primer, which is identical to a consecutive stretch of the target nucleic acid sequence comprising said first variant sequence except for up to one mismatch, and a second primer 1 together with the primer 2 is capable of amplification of a target nucleic acid sequence comprising a second variant sequence, wherein said second primer 1 comprises a sequence of at least 15 nucleotides positioned at the 3' end of said primer, which is identical to a consecutive stretch of the target nucleic acid sequence comprising said second variant sequence except for up to one mismatch; and wherein the sets of primers optionally comprise one or more further primer 1, which together with the primer 2 are capable of amplification of a target nucleic acid sequence comprising one or more further variant sequence(s), wherein said further primer 1(s) comprise a sequence of at least 15 nucleotides positioned at the 3' end of said primer, which is identical to a consecutive stretch of the target nucleic acid sequence comprising said further variant sequence(s) except for up to one mismatch;
d) performing a polymerase chain reaction in the presence of said sample, said blocking oligonucleotide; and said set of primers;
e) detecting a product of said polymerase chain reaction, wherein the presence of a product of said polymerase chain reaction indicates the presence of a target nucleic acid sequence comprising the variant sequence in said sample.

2. The method according to claim 1, wherein the step of detecting said product comprises use of a detection probe.

3. The method according to claim 1, wherein the method comprises a kit comprising
a) one blocking oligonucleotide consisting of a sequence of in the range of 10 to 50 nucleotides (referred to as "blocking sequence") into which in the range of 2 to 10 hydrophobic nucleotides have been inserted,
wherein
at least one hydrophobic nucleotide is positioned at the 5' end of said sequence or within 4 nucleotides from the 5' end; and
at least one hydrophobic nucleotide is positioned at the 3' end of said sequence or within 4 nucleotides from the 3' end; and
Z is a hydrophobic nucleotide of the structure

X—Y-Q wherein
X is a backbone monomer unit,
Q is an intercalator, which is not taking part in Watson-Crick hydrogen bonding; and
Y is a linker moiety linking said nucleotide or nucleotide analogue or backbone monomer unit and said intercalator; and
wherein the blocking sequence is identical to a consecutive stretch of a target nucleic acid sequence comprising a reference NOI sequence; and
sets of primers comprising at least two different primer 1 together with a primer 2, wherein a first primer 1 together with the primer 2 is capable of amplification of a target nucleic acid sequence comprising a first variant sequence, wherein said first primer 1 comprises a sequence of at least 15 nucleotides positioned at the 3' end of said primer, which is identical to a consecutive stretch of the target nucleic acid sequence comprising said first variant sequence except for up to one mismatch, and a second primer 1 together with the primer 2 is capable of amplification of a target nucleic acid sequence comprising a second variant sequence, wherein said second primer 1 comprises a sequence of at least 15 nucleotides positioned at the 3' end of said primer, which is identical to a consecutive stretch of the target nucleic acid sequence comprising said second variant sequence except for up to one mismatch; and wherein the sets of primers optionally comprise one or more further primer 1, which together with the primer 2 are capable of amplification of a target nucleic acid sequence comprising one or more further variant sequence(s), wherein said further primer 1 comprise a sequence of at least 15 nucleotides positioned at the 3' end of said primer, which is identical to a consecutive stretch of the target nucleic acid sequence comprising said further variant sequence(s) except for up to one mismatch.

4. The method according to claim 1, wherein the primer 1 comprises a sequence which is identical to a consecutive sequence of the blocking sequence of at least 3 nucleotides except for up to one mismatch.

5. The method according to claim 4, wherein the sequence of the primer 1, which is identical to a consecutive sequence of the blocking sequence, is positioned immediately 5' to the sequence identical to the variant sequence.

6. The method of claim 4, wherein the consecutive sequence of the blocking sequence is of at least 6 nucleotides except for up to one mismatch.

7. The method according to claim 1, wherein the 3' nucleotide of primer 1 is identical to the variant sequence.

8. The method according to claim 1, wherein the variant sequence is a single nucleotide variant.

9. The method according to claim 1, wherein said mismatch is positioned at position 2, 3 or 4 from the 3' end of primer 1.

10. The method according to claim 1, wherein primer 2 comprises a sequence of at least 15 nucleotides, which is complementary to a consecutive sequence of the target nucleic acid sequence.

11. The method according to claim 1, wherein the blocking oligonucleotide has the following structure $$5'\text{-}(N)_a\text{—}Z\text{—}(N)_i\text{—}Z\text{—}(N)_j\text{—}Z\text{—}(N)_k\text{—}Z\text{—}(N)_l\text{—}Z\text{—}(N)_b\text{-}3'$$

wherein
N is any nucleotide or nucleotide analogue; and

Z is a hydrophobic nucleotide having the structure X—Y-Q wherein X is a nucleotide or nucleotide analogue or a backbone monomer unit, Q is a intercalator which is not taking part in Watson-Crick hydrogen bonding, and Y is a linker moiety linking said nucleotide or nucleotide analogue or backbone monomer unit and said intercalator; and a and b individually are integers in the range from 0 to 4; and j, k and l individually are integers in the range from 1 to 17; and a+b+i+j+k+l is at least 10 and at the most 50; and $(N)_a$—$(N)_i$—$(N)_j$—$(N)_k$—$(N)_l(N)_b$ is identical to a stretch of the target nucleic acid sequence comprising a reference NOI sequence; or having the following structure 5'-$(N)_a$—Z—$(N)_m$—Z—$(N)_n$—Z—$(N)_o$—Z—$(N)_p$—Z—$(N)_q$—Z—$(N)_b$-3' wherein

N is any nucleotide or nucleotide analogue; and

Z is a hydrophobic nucleotide having the structure X—Y-Q wherein X is a nucleotide or nucleotide analogue or a backbone monomer unit, Q is a intercalator which is not taking part in Watson-Crick hydrogen bonding, and Y is a linker moiety linking said nucleotide or nucleotide analogue or backbone monomer unit and said intercalator; and a and b individually are integers in the range of 0 to 4; and m, n, o, p and q individually are integers in the range of 1 to 16; and a+b+m+n+o+p+q is at least 10 and at the most 50; and $(N)_a$—$(N)_m$—$(N)_n$—$(N)_o$—$(N)_p$—Z—$(N)_q$—$(N)_b$ is identical to a stretch of the target nucleic acid sequence comprising a reference NOI sequence.

12. The method according to claim 1, wherein at least one hydrophobic nucleotide comprises an intercalator which is pyrene or pyrido[3',2':4,5]thieno[3,2-d]pyrimidin-4(1H)-one or 7,9-dimethyl-pyrido[3',2',4,5]thieno[3,2-d]pyrimidin-4(3H)-one.

13. The method according to claim 1, wherein at least one backbone monomer unit X is selected from the group consisting of phosphoramidites.

14. A method of predicting the presence of a clinical condition in an individual in need thereof, wherein said clinical condition is associated with a target nucleic acid sequence comprising a variant sequence, said method comprising the steps of c. providing a sample from said individual d. performing the method according to claim 1 to determine the presence of said variant sequence;

wherein the presence of said variant sequence is indicative of said individual suffering from said clinical condition.

15. The method according to claim 14, wherein the clinical condition is cancer.

16. A kit-of-parts comprising a) one blocking oligonucleotide consisting of a sequence of in the range of 10 to 50 nucleotides (referred to as "blocking sequence") into which in the range of 2 to 10 hydrophobic nucleotides have been inserted, wherein at least one hydrophobic nucleotide is positioned at the 5' end of said sequence or within 4 nucleotides from the 5' end; and at least one hydrophobic nucleotide is positioned at the 3' end of said sequence or within 4 nucleotides from the 3' end; and Z is a hydrophobic nucleotide of the structure

X—Y-Q wherein

X is a backbone monomer unit,

Q is an intercalator, which is not taking part in Watson-Crick hydrogen bonding; and Y is a linker moiety linking said nucleotide or nucleotide analogue or backbone monomer unit and said intercalator; and wherein the blocking sequence is identical to a consecutive stretch of a target nucleic acid sequence comprising a reference nucleotide(s) of interest (NOI) sequence; and b) sets of primers comprising at least two different primer 1 together with a primer 2, wherein a first primer 1 together with the primer 2 is capable of amplification of a target nucleic acid sequence comprising a first variant sequence, wherein said first primer 1 comprises a sequence of at least 15 nucleotides positioned at the 3' end of said primer, which is identical to a consecutive stretch of the target nucleic acid sequence comprising said first variant sequence except for up to one mismatch, and a second primer 1 together with the primer 2 is capable of amplification of a target nucleic acid sequence comprising a second variant sequence, wherein said second primer 1 comprises a sequence of at least 15 nucleotides positioned at the 3' end of said primer, which is identical to a consecutive stretch of the target nucleic acid sequence comprising said second variant sequence except for up to one mismatch; and wherein the sets of primers optionally comprise one or more further primer 1, which together with the primer 2 are capable of amplification of a target nucleic acid sequence comprising one or more further variant sequence(s), wherein said further primer 1 comprise a sequence of at least 15 nucleotides positioned at the 3' end of said primer, which is identical to a consecutive stretch of the target nucleic acid sequence comprising said further variant sequence(s) except for up to one mismatch.

17. The kit according to claim 16, wherein the kit furthermore comprises a detection probe.

18. The kit according to claim 16, wherein the kit comprises at least two different blocking oligonucleotides wherein at least one blocking oligonucleotide contains a blocking sequence identical to a consecutive stretch of a target nucleic acid sequence comprising a reference NOI sequence, and one or more blocking oligonucleotide(s) contain blocking sequence(s) identical to a consecutive stretch of a target nucleic acid sequence comprising other variant sequence(s), wherein said other variant sequences are different from the variant sequence identical to a stretch of primer 1.

19. A blocking oligonucleotide having the following structure

5'-$(N)_a$—Z—$(N)_i$—Z—$(N)_j$—Z—$(N)_l$—Z—$(N)_l$—Z—$(N)_b$-3' wherein

N is any nucleotide or nucleotide analogue; and

Z is a hydrophobic nucleotide having the structure X—Y-Q wherein X is a nucleotide or nucleotide analogue or a backbone monomer unit, Q is a intercalator which is not taking part in Watson-Crick hydrogen bonding, and Y is a linker moiety linking said nucleotide or nucleotide analogue or backbone monomer unit and said intercalator; and a and b individually are integers in the range from 0 to 4; and j, k and l individually are integers in the range from 1 to 17; and a+b+i+j+k+l is at least 10 and at the most 50; and $(N)_a$—$(N)_i$—$(N)_j$—$(N)_k$—$(N)_l$—$(N)_b$ is identical to a stretch of the target nucleic acid sequence comprising a reference nucleotide(s) of interest NOI sequence; or having the following structure

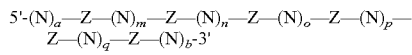

wherein

N is any nucleotide or nucleotide analogue; and

Z is a hydrophobic nucleotide having the structure X—Y-Q wherein X is a nucleotide or nucleotide analogue or a backbone monomer unit, Q is a intercalator which is not taking part in Watson-Crick hydrogen bonding, and Y is a linker moiety linking said nucleotide or nucleotide analogue or backbone monomer unit and said intercalator; and a and b individually are integers in the range of 0 to 4; and m, n, o, p and q individually are integers in the range of 1 to 16; and a+b+m+n+o+p+q is at least 10 and at the most 50; and $(N)_a$—$(N)_m$—$(N)_n$—$(N)_o$—$(N)_p$—Z—$(N)_q$—$(N)_b$ is identical to a stretch of the target nucleic acid sequence comprising a reference NOI sequence.

20. A method of predicting the efficacy of treatment of a clinical condition in an individual in need thereof with a predetermined drug, wherein the efficacy of treatment of said clinical condition with said drug is associated with the presence of a variant sequence, said method comprising the steps of a. providing a sample from said individual b. performing the method according to claim 1 to determine the presence of said variant sequence;

wherein the presence of said variant sequence is indicative of whether said drug is efficient in treating said clinical condition in said individual.

* * * * *